US012624083B2

(12) United States Patent
Yang et al.

(10) Patent No.: US 12,624,083 B2
(45) Date of Patent: May 12, 2026

(54) CHIMERIC ANTIGEN RECEPTORS AGAINST HUMAN CYTOMEGALOVIRUS

(71) Applicants: The Regents of the University of California, Oakland, CA (US); City of Hope, Duarte, CA (US)

(72) Inventors: Otto O. Yang, Los Angeles, CA (US); Ayub Ali, Porter Ranch, CA (US); Don J. Diamond, Glendora, CA (US); Flavia Chiuppesi, Monrovia, CA (US); Felix Wussow, Monrovia, CA (US)

(73) Assignees: The Regents of the University of California, Oakland, CA (US); City of Hope, Duarte, CA (US)

( * ) Notice: Subject to any disclaimer, the term of this patent is extended or adjusted under 35 U.S.C. 154(b) by 1072 days.

(21) Appl. No.: 17/766,989

(22) PCT Filed: Oct. 12, 2020

(86) PCT No.: PCT/US2020/055194
§ 371 (c)(1),
(2) Date: Apr. 6, 2022

(87) PCT Pub. No.: WO2021/072353
PCT Pub. Date: Apr. 15, 2021

(65) Prior Publication Data
US 2024/0082403 A1     Mar. 14, 2024

Related U.S. Application Data

(60) Provisional application No. 62/914,408, filed on Oct. 11, 2019.

(51) Int. Cl.
*A61K 39/00*     (2006.01)
*A61K 40/11*     (2025.01)
(Continued)

(52) U.S. Cl.
CPC .......... *C07K 14/7051* (2013.01); *A61K 40/11* (2025.01); *A61K 40/31* (2025.01);
(Continued)

(58) Field of Classification Search
None
See application file for complete search history.

(56) References Cited

U.S. PATENT DOCUMENTS

2015/0038684 A1    2/2015   Jensen
2017/0275374 A1    9/2017   Schiffer-Mannioui
(Continued)

FOREIGN PATENT DOCUMENTS

WO    WO-2016154628 A1 *   9/2016   ......... C07K 16/2803
WO       2017044895        3/2017
(Continued)

OTHER PUBLICATIONS

SEQ 11 alignment with Geneseq db access No. BDR51843 in WO2017044895 by Diamond et al. Mar. 2017.*
(Continued)

*Primary Examiner* — Shanon A. Foley
(74) *Attorney, Agent, or Firm* — Suzannah K. Sundby, Esq.; Canady + Lortz LLP

(57)          ABSTRACT

Disclosed herein are CMV-specific CARs. In some embodiments. the present invention is directed to a method of treating, reducing, or inhibiting an infection by a cytomegalovirus in a subject, which comprises administering to the subject (a) an expression vector that encodes a CMV-specific CAR as described herein, or (b) one or more cells that are transduced with the expression vector.

17 Claims, 14 Drawing Sheets

Specification includes a Sequence Listing.

(51) Int. Cl.

| | | |
|---|---|---|
| *A61K 40/31* | (2025.01) | |
| *A61K 40/46* | (2025.01) | |
| *A61P 31/22* | (2006.01) | |
| *C07K 14/725* | (2006.01) | |
| *C07K 16/08* | (2006.01) | |
| *C07K 16/085* | (2026.01) | |

(52) U.S. Cl.

CPC .............. *A61K 40/46* (2025.01); *A61P 31/22* (2018.01); *C07K 16/089* (2023.08); *C07K 2317/622* (2013.01)

(56) References Cited

U.S. PATENT DOCUMENTS

| 2018/0214527 A1 | 8/2018 | Wang et al. |
|---|---|---|
| 2019/0247500 A1 | 8/2019 | Diamond |

FOREIGN PATENT DOCUMENTS

| WO | WO-2017044895 A2 * | 3/2017 | ....... G01N 33/56994 |
|---|---|---|---|
| WO | 2018075813 | 4/2018 | |
| WO | 2018231759 | 12/2018 | |

OTHER PUBLICATIONS

SEQ 12 alignment with Geneseq db access No. BDR51844 in WO2017044895 by Diamond et al. Mar. 2017.*

Paul, Fundamental Immunology, 3 rd Edition, 1993, pp. 292-295, under the heading "Fv Structure and Diversity in Three Dimensions".*

Rudikoff et al (Proc. Natl. Acad. Sci. USA, 79:1979-1983, Mar. 1982).*

Colman P. M. (Research in Immunology, 145:33-36, 1994).*

Klenerman et al. (Nature Reviews Immunology. Jun. 2016: 367-377).*

Ali et al. (The Journal of Infectious Diseases. Sep. 2020; 222: 853-862) describe CMV-targeted CARs.*

Saren et al. (Nature Communications. 2023; 14: 4732).*

Ali et al., Chimeric Antigen Receptors Targeting Human Cytomegalovirus, Aug. 4, 2020, pp. 853-862, vol. 222, No. 5, Publisher: J Infect Dis.

Supplementary European Search Report received in EP 20875365.7 mailed Dec. 19, 2023.

Full et al., T cells engineered with a cytomegalovirus-specific chimeric immunoreceptor, Apr. 1, 2010, pp. 4083-4088, vol. 84, No. 8, Publisher: J Virol.

Proff et al., Turning the tables on cytomegalovirus: targeting viral Fc receptors by CARs containing mutated CH2-CH3 IgG spacer domains, Feb. 8, 2018, p. 26, vol. 16, No. 1, Publisher: J Transl Med.

Proff et al., Cytomegalovirus-Infected Cells Resist T Cell Mediated Killing in an HLA-Recognition Independent Manner, Jun. 9, 2016, p. 844, vol. 7, Publisher: Front Microbiol.

Schuessler et al., Cytomegalovirus as a novel target for immunotherapy of glioblastoma multiforme, Oct. 7, 2014, p. 275, vol. 4, Publisher: Front Oncol.

International Search Report received in PCT/US2020/055194, mailed Mar. 19, 2021.

Written Opinion received in PCT/US2020/055194, mailed Mar. 19, 2021.

Office Action received in JP2022521224 mailed Aug. 29, 2024.

\* cited by examiner

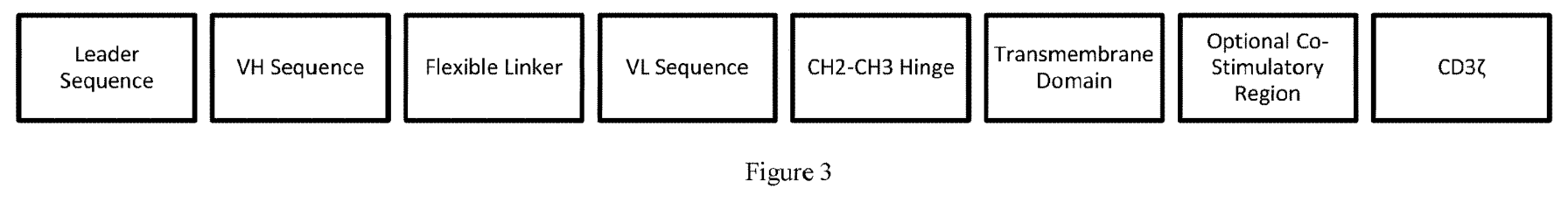

| Leader Sequence | VH Sequence | Flexible Linker | VL Sequence | CH2-CH3 Hinge | Transmembrane Domain | Optional Co-Stimulatory Region | CD3ζ |

Figure 3

1. 18F10 CAR
2. 12E2 CAR
3. 2-80 CAR
4. 21F6 CAR
5. 1B2 CAR
6. 13B5 CAR
7. 54E11 CAR
8. 62-11 CAR
9. 21E9 CAR
C. Untransduced Surface Antibody

SEQUENCE LISTING

<160> NUMBER OF SEQ ID NOS: 91

<210> SEQ ID NO 1
<211> LENGTH: 118
<212> TYPE: PRT
<213> ORGANISM: Artificial Sequence
<220> FEATURE:
<223> OTHER INFORMATION: 1B2 VH

<400> SEQUENCE: 1

Glu Val Gln Leu Val Glu Ser Gly Gly Val Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Asp Gly Asn Tyr Thr Asn Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Gly Trp Leu Leu Pro Val Phe Ala Tyr Trp Gly Gln Gly Thr
            100                 105                 110

Leu Val Thr Val Ser Ala
        115

<210> SEQ ID NO 2
<211> LENGTH: 107
<212> TYPE: PRT
<213> ORGANISM: Artificial Sequence
<220> FEATURE:
<223> OTHER INFORMATION: 1B2 VL

<400> SEQUENCE: 2

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Thr Ser Gln Ser Ile Ser Gly Ile Pro Ser Arg Phe Ser Gly
    50                  55                  60

Ser Gly Ser Gly Thr Asp Phe Thr Leu Asn Ile Asn Ser Val Glu Thr
65                  70                  75                  80

Glu Asp Phe Gly Val Tyr Phe Cys Gln Gln Ser Asn Arg Trp Pro Trp
                85                  90                  95

Thr Phe Gly Gly Gly Thr Lys Leu Glu Ile Lys
            100                 105

<210> SEQ ID NO 3
<211> LENGTH: 121
<212> TYPE: PRT
<213> ORGANISM: Artificial Sequence
<220> FEATURE:
<223> OTHER INFORMATION: 21F6/54E11 VH

<400> SEQUENCE: 3

Gln Ile Gln Leu Val Gln Ser Gly Pro Glu Leu Lys Lys Pro Gly Glu
1               5                   10                  15

-continued

```
Thr Val Lys Ile Ser Cys Lys Ala Ser Gly Tyr Thr Phe Thr Ser Tyr
            20                  25                  30

Gly Met Asn Trp Val Lys Gln Ala Pro Gly Lys Gly Leu Lys Trp Met
            35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Glu His Tyr Tyr Gly Ile Asn Pro Leu Leu Gly Cys Trp Gly
            100                 105                 110

Gln Gly Thr Thr Leu Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: 21F6/54E11 VL

<400> SEQUENCE: 4

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Asp Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: 12E2 VH

<400> SEQUENCE: 5

```
Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Phe Trp Val Arg Gln Thr Pro Glu Lys Lys Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Ser Arg Asp Asn Asp Lys Asn Thr Leu Tyr
65                  70                  75                  80

Leu Gln Met Ser Arg Leu Lys Ser Asp Asp Thr Ala Leu Tyr Tyr Cys
```

-continued

```
                    85                  90                  95

Val Arg Pro Lys Arg Asp Phe Gln Tyr Leu Tyr Ala Met Asp Tyr Trp
            100                 105                 110

Gly Gln Gly Thr Ser Val Thr Val Ser Ser
        115                 120

<210> SEQ ID NO 6
<211> LENGTH: 111
<212> TYPE: PRT
<213> ORGANISM: Artificial Sequence
<220> FEATURE:
<223> OTHER INFORMATION: 12E2 VL

<400> SEQUENCE: 6

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Ser Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Asp Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys
            100                 105                 110

<210> SEQ ID NO 7
<211> LENGTH: 123
<212> TYPE: PRT
<213> ORGANISM: Artificial Sequence
<220> FEATURE:
<223> OTHER INFORMATION: 13B5 VH

<400> SEQUENCE: 7

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Thr Thr Ser
            20                  25                  30

Gly Leu Gly Val Gly Trp Ile Arg Gln Pro Ser Gly Lys Gly Leu Glu
        35                  40                  45

Trp Leu Ala His Ile Trp Trp Asp Asp Asp Lys Tyr Phe Asn Pro Ser
    50                  55                  60

Leu Arg Asn Gln Leu Thr Ile Ser Lys Asp Thr Ser Arg Asn Gln Val
65                  70                  75                  80

Phe Leu Glu Ile Thr Ser Val Thr Thr Ala Asp Thr Ala Thr Tyr Tyr
                85                  90                  95

Cys Val Arg Ser Leu Tyr Asp Tyr Asp Glu Gly Tyr Tyr Phe Asp Ser
            100                 105                 110

Trp Gly Gln Gly Thr Thr Leu Thr Val Ser Ser
        115                 120

<210> SEQ ID NO 8
<211> LENGTH: 107
<212> TYPE: PRT
<213> ORGANISM: Artificial Sequence
<220> FEATURE:
```

<223> OTHER INFORMATION: 13B5 VL

<400> SEQUENCE: 8

```
Glu Ile Val Met Ile Gln Ser Pro Ala Thr Leu Ser Val Asn Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Thr Phe Pro Pro
                85                  90                  95

Thr Phe Gly Gly Gly Thr Lys Leu Glu Ile Lys
            100                 105
```

<210> SEQ ID NO 9
<211> LENGTH: 116
<212> TYPE: PRT
<213> ORGANISM: Artificial Sequence
<220> FEATURE:
<223> OTHER INFORMATION: 18F10 VH

<400> SEQUENCE: 9

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Ile Gly Trp Ile Arg Gln Pro Ser Gly Lys Gly Leu Glu
        35                  40                  45

Trp Leu Ala His Ile Trp Trp Asn Asp Asn Lys Asn Tyr Asn Thr Ala
    50                  55                  60

Leu Lys Ser Arg Leu Thr Ile Ser Lys Asp Pro Ser Asn Asn Gln Val
65                  70                  75                  80

Phe Leu Lys Ile Ala Ser Val Asp Thr Ala Asp Thr Ala Thr Tyr Phe
                85                  90                  95

Cys Ala Arg Thr Gly Tyr Phe Asp Val Trp Gly Ala Gly Thr Thr Val
            100                 105                 110

Thr Val Ser Ser
        115
```

<210> SEQ ID NO 10
<211> LENGTH: 112
<212> TYPE: PRT
<213> ORGANISM: Artificial Sequence
<220> FEATURE:
<223> OTHER INFORMATION: 18F10 VL

<400> SEQUENCE: 10

```
Asp Val Val Leu Thr Gln Thr Pro Leu Ser Leu Pro Val Ser Leu Gly
1               5                   10                  15

Asp Gln Val Ser Ile Ser Cys Ser Ser Ser Gln Ser Leu Val His Ser
            20                  25                  30

Asn Gly Asn Thr Tyr Ile His Trp Tyr Leu Gln Lys Pro Gly Gln Ser
        35                  40                  45

Pro Lys Leu Leu Ile Tyr Thr Val Ser Asn Arg Phe Ser Gly Val Pro
```

```
        50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Leu Tyr Phe Cys Ser Gln Ser
                85              90              95

Thr His Val Pro Tyr Thr Phe Gly Gly Gly Thr Lys Leu Glu Ile Lys
            100             105             110

<210> SEQ ID NO 11
<211> LENGTH: 121
<212> TYPE: PRT
<213> ORGANISM: Artificial Sequence
<220> FEATURE:
<223> OTHER INFORMATION: 21E9 VH

<400> SEQUENCE: 11

Gln Ile Gln Leu Val Gln Ser Gly Pro Glu Leu Lys Lys Pro Gly Glu
1               5               10              15

Thr Val Lys Ile Ser Cys Lys Ala Ser Gly Tyr Thr Phe Thr Ile Tyr
                20              25              30

Gly Met Asn Trp Val Lys Gln Ala Pro Gly Lys Gly Leu Lys Trp Met
            35              40              45

Gly Trp Ile Asn Thr Tyr Thr Gly Glu Pro Thr Tyr Ala Asp Asp Phe
        50              55              60

Arg Gly Arg Phe Ala Phe Ser Leu Glu Thr Ser Ala Ser Thr Ala Tyr
65              70              75              80

Leu Gln Ile Asn Asn Leu Lys Asn Glu Asp Thr Ala Thr Tyr Phe Cys
                85              90              95

Ala Arg Lys Gly Tyr Tyr Gly Ser Ser Gly Tyr Phe Asp Tyr Trp Gly
            100             105             110

Gln Gly Thr Thr Leu Thr Val Ser Ser
            115             120

<210> SEQ ID NO 12
<211> LENGTH: 107
<212> TYPE: PRT
<213> ORGANISM: Artificial Sequence
<220> FEATURE:
<223> OTHER INFORMATION: 21E9 VL

<400> SEQUENCE: 12

Ser Ile Val Met Thr Gln Thr Pro Lys Phe Leu Leu Val Ser Ala Gly
1               5               10              15

Asp Arg Val Thr Ile Thr Cys Lys Ala Ser Gln Ser Val Ser Asn Asp
                20              25              30

Val Ser Trp Tyr Gln Gln Lys Pro Gly Gln Ser Pro Lys Leu Leu Ile
            35              40              45

Tyr Tyr Ala Ser Asn Arg Tyr Thr Gly Val Pro Asp Arg Phe Thr Gly
        50              55              60

Ser Gly Tyr Gly Thr Asp Phe Thr Phe Thr Ile Ser Thr Val Gln Ala
65              70              75              80

Glu Asp Leu Ala Val Tyr Phe Cys Gln Gln Asp Tyr Ser Ser Pro Trp
                85              90              95

Thr Phe Gly Gly Gly Thr Lys Leu Glu Ile Lys
            100             105

<210> SEQ ID NO 13
<211> LENGTH: 116
```

-continued

```
<212> TYPE: PRT
<213> ORGANISM: Artificial Sequence
<220> FEATURE:
<223> OTHER INFORMATION: 62-11 VH

<400> SEQUENCE: 13

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Asn Gly Tyr Ser Ser Phe Ala Tyr Trp Gly Gln Gly Thr Leu Val
            100                 105                 110

Thr Val Ser Val
        115

<210> SEQ ID NO 14
<211> LENGTH: 107
<212> TYPE: PRT
<213> ORGANISM: Artificial Sequence
<220> FEATURE:
<223> OTHER INFORMATION: 62-11 VL
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa is V or I

<400> SEQUENCE: 14

Asp Xaa Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Asp Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105

<210> SEQ ID NO 15
<211> LENGTH: 119
<212> TYPE: PRT
<213> ORGANISM: Artificial Sequence
<220> FEATURE:
<223> OTHER INFORMATION: 2-80 VH

<400> SEQUENCE: 15
```

-continued

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Phe
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Ser
65                  70                  75                  80

Leu Gln Ile Asn Asn Leu Lys Asn Glu Asp Thr Ala Thr Tyr Phe Cys
                85                  90                  95

Ala Arg Arg Gly Asp Gly Leu Tyr Ser Met Asp Tyr Trp Gly Gln Gly
            100                 105                 110

Thr Ser Val Thr Val Ser Ser
            115

<210> SEQ ID NO 16
<211> LENGTH: 111
<212> TYPE: PRT
<213> ORGANISM: Artificial Sequence
<220> FEATURE:
<223> OTHER INFORMATION: 2-80 VL

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile Asp Ser Tyr
            20                  25                  30

Gly Asn Ser Phe Met Tyr Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Leu Thr Phe Gly Ala Gly Thr Lys Leu Glu Leu Lys
            100                 105                 110

<210> SEQ ID NO 17
<211> LENGTH: 115
<212> TYPE: PRT
<213> ORGANISM: Artificial Sequence
<220> FEATURE:
<223> OTHER INFORMATION: 4A3 VH

<400> SEQUENCE: 17

Gln Val Gln Leu Gln Gln Pro Gly Pro Glu Leu Val Arg Pro Gly Ala
1               5                   10                  15

Ser Val Lys Leu Ser Cys Lys Ala Ser Gly Tyr Thr Phe Thr Ile Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Ser Thr Ala Tyr

```
65                   70                  75                  80

Met Gln Leu Ser Ser Leu Thr Ser Glu Asp Ser Ala Val Tyr Tyr Cys
                85                  90                  95

Ala Ser Ser Gly Thr Gly Ala Tyr Trp Gly Gln Gly Thr Leu Leu Thr
            100                 105                 110

Val Ser Ala
        115

<210> SEQ ID NO 18
<211> LENGTH: 112
<212> TYPE: PRT
<213> ORGANISM: Artificial Sequence
<220> FEATURE:
<223> OTHER INFORMATION: 4A3 VL

<400> SEQUENCE: 18

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Leu Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 19
<211> LENGTH: 116
<212> TYPE: PRT
<213> ORGANISM: Artificial Sequence
<220> FEATURE:
<223> OTHER INFORMATION: 62-100 VH

<400> SEQUENCE: 19

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile Asp Pro Ser Asp Ser Glu Thr His Tyr Asn Gln Met Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Asn Gly Tyr Ser Ser Phe Ala Tyr Trp Gly Gln Gly Thr Leu Val
            100                 105                 110

Thr Val Ser Val
        115

<210> SEQ ID NO 20
<211> LENGTH: 107
```

```
<212> TYPE: PRT
<213> ORGANISM: Artificial Sequence
<220> FEATURE:
<223> OTHER INFORMATION: 62-100 VL

<400> SEQUENCE: 20

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Lys Tyr Val Cys Gln Gln Ser Asn Ser Trp Pro Leu
                85                  90                  95

Thr Phe Gly Ser Gly Thr Lys Leu Glu Ile Lys
            100                 105

<210> SEQ ID NO 21
<211> LENGTH: 10
<212> TYPE: PRT
<213> ORGANISM: Artificial Sequence
<220> FEATURE:
<223> OTHER INFORMATION: Formula H1
<220> FEATURE:
<221> NAME/KEY: misc_feature
<222> LOCATION: (2)..(2)
<223> OTHER INFORMATION: Xaa is F or Y
<220> FEATURE:
<221> NAME/KEY: misc_feature
<222> LOCATION: (3)..(3)
<223> OTHER INFORMATION: Xaa is S or T
<220> FEATURE:
<221> NAME/KEY: misc_feature
<222> LOCATION: (4)..(4)
<223> OTHER INFORMATION: Xaa is L or F
<220> FEATURE:
<221> NAME/KEY: misc_feature
<222> LOCATION: (5)..(5)
<223> OTHER INFORMATION: Xaa is S or T
<220> FEATURE:
<221> NAME/KEY: misc_feature
<222> LOCATION: (6)..(6)
<223> OTHER INFORMATION: Xaa is D, I, N, S, or T
<220> FEATURE:
<221> NAME/KEY: misc_feature
<222> LOCATION: (7)..(7)
<223> OTHER INFORMATION: Xaa is F, Y, or S
<220> FEATURE:
<221> NAME/KEY: misc_feature
<222> LOCATION: (8)..(8)
<223> OTHER INFORMATION: Xaa is G, Y, or W
<220> FEATURE:
<221> NAME/KEY: misc_feature
<222> LOCATION: (9)..(9)
<223> OTHER INFORMATION: Xaa is present or absent and if present Xaa is
      L or I
<220> FEATURE:
<221> NAME/KEY: misc_feature
<222> LOCATION: (10)..(10)
<223> OTHER INFORMATION: Xaa is present or absent and if present Xaa is
      G

<400> SEQUENCE: 21

Gly Xaa Xaa Xaa Xaa Xaa Xaa Xaa Xaa Xaa
1               5                   10
```

```
<210> SEQ ID NO 22
<211> LENGTH: 8
<212> TYPE: PRT
<213> ORGANISM: Artificial Sequence
<220> FEATURE:
<223> OTHER INFORMATION: Formula H2
<220> FEATURE:
<221> NAME/KEY: misc_feature
<222> LOCATION: (2)..(2)
<223> OTHER INFORMATION: Xaa is D, N, S, or W
<220> FEATURE:
<221> NAME/KEY: misc_feature
<222> LOCATION: (3)..(3)
<223> OTHER INFORMATION: Xaa is D, N, P, T, or W
<220> FEATURE:
<221> NAME/KEY: misc_feature
<222> LOCATION: (4)..(4)
<223> OTHER INFORMATION: Xaa is D, G, N, Y, or S
<220> FEATURE:
<221> NAME/KEY: misc_feature
<222> LOCATION: (5)..(5)
<223> OTHER INFORMATION: Xaa is D, G, or T
<220> FEATURE:
<221> NAME/KEY: misc_feature
<222> LOCATION: (6)..(6)
<223> OTHER INFORMATION: Xaa is D, G, N, or S
<220> FEATURE:
<221> NAME/KEY: misc_feature
<222> LOCATION: (7)..(7)
<223> OTHER INFORMATION: Xaa is E, K, S, or Y
<220> FEATURE:
<221> NAME/KEY: misc_feature
<222> LOCATION: (8)..(8)
<223> OTHER INFORMATION: Xaa is present or absent and if present Xaa is
      P or T

<400> SEQUENCE: 22

Ile Xaa Xaa Xaa Xaa Xaa Xaa Xaa
1               5

<210> SEQ ID NO 23
<211> LENGTH: 15
<212> TYPE: PRT
<213> ORGANISM: Artificial Sequence
<220> FEATURE:
<223> OTHER INFORMATION: Formula H3
<220> FEATURE:
<221> NAME/KEY: misc_feature
<222> LOCATION: (1)..(1)
<223> OTHER INFORMATION: Xaa is A, S, or V
<220> FEATURE:
<221> NAME/KEY: misc_feature
<222> LOCATION: (2)..(2)
<223> OTHER INFORMATION: Xaa is R, N, or S
<220> FEATURE:
<221> NAME/KEY: misc_feature
<222> LOCATION: (3)..(3)
<223> OTHER INFORMATION: Xaa is E, G, K, P, R, or S
<220> FEATURE:
<221> NAME/KEY: misc_feature
<222> LOCATION: (4)..(4)
<223> OTHER INFORMATION: Xaa is G, H, K, L, Y, or W
<220> FEATURE:
<221> NAME/KEY: misc_feature
<222> LOCATION: (5)..(5)
<223> OTHER INFORMATION: Xaa is D, L, R, S, or Y
<220> FEATURE:
<221> NAME/KEY: misc_feature
<222> LOCATION: (6)..(6)
<223> OTHER INFORMATION: Xaa is D, F, G, L, S, or Y
<220> FEATURE:
<221> NAME/KEY: misc_feature
<222> LOCATION: (7)..(7)
<223> OTHER INFORMATION: Xaa is A, D, F, G, L, P, or Y
<220> FEATURE:
<221> NAME/KEY: misc_feature
```

-continued

```
<222> LOCATION: (8)..(8)
<223> OTHER INFORMATION: Xaa is A, D, I, Q, S, V, or Y
<220> FEATURE:
<221> NAME/KEY: misc_feature
<222> LOCATION: (9)..(9)
<223> OTHER INFORMATION: Xaa is present or absent and if present Xaa is
      E, F, N, S, or Y
<220> FEATURE:
<221> NAME/KEY: misc_feature
<222> LOCATION: (10)..(10)
<223> OTHER INFORMATION: Xaa is present or absent and if present Xaa is
      A, G, M, L, or P
<220> FEATURE:
<221> NAME/KEY: misc_feature
<222> LOCATION: (11)..(11)
<223> OTHER INFORMATION: Xaa is present or absent and if present Xaa is
      D, L, or Y
<220> FEATURE:
<221> NAME/KEY: misc_feature
<222> LOCATION: (12)..(12)
<223> OTHER INFORMATION: Xaa is present or absent and if present Xaa is
      A, F, L, or Y
<220> FEATURE:
<221> NAME/KEY: misc_feature
<222> LOCATION: (13)..(13)
<223> OTHER INFORMATION: Xaa is present or absent and if present Xaa is
      D, F, G, or M
<220> FEATURE:
<221> NAME/KEY: misc_feature
<222> LOCATION: (14)..(14)
<223> OTHER INFORMATION: Xaa is present or absent and if present Xaa is
      C, D, or Y
<220> FEATURE:
<221> NAME/KEY: misc_feature
<222> LOCATION: (15)..(15)
<223> OTHER INFORMATION: Xaa is present or absent and if present Xaa is
      S or Y

<400> SEQUENCE: 23

Xaa Xaa Xaa Xaa Xaa Xaa Xaa Xaa Xaa Xaa Xaa Xaa Xaa Xaa Xaa
1               5                   10                  15

<210> SEQ ID NO 24
<211> LENGTH: 11
<212> TYPE: PRT
<213> ORGANISM: Artificial Sequence
<220> FEATURE:
<223> OTHER INFORMATION: Formula L1
<220> FEATURE:
<221> NAME/KEY: misc_feature
<222> LOCATION: (1)..(1)
<223> OTHER INFORMATION: Xaa is E, K, or Q
<220> FEATURE:
<221> NAME/KEY: misc_feature
<222> LOCATION: (2)..(2)
<223> OTHER INFORMATION: Xaa is G or S
<220> FEATURE:
<221> NAME/KEY: misc_feature
<222> LOCATION: (3)..(3)
<223> OTHER INFORMATION: Xaa is I, L, or V
<220> FEATURE:
<221> NAME/KEY: misc_feature
<222> LOCATION: (4)..(4)
<223> OTHER INFORMATION: Xaa is D, G, S, or V
<220> FEATURE:
<221> NAME/KEY: misc_feature
<222> LOCATION: (5)..(5)
<223> OTHER INFORMATION: Xaa is D, H, N, S, or T
<220> FEATURE:
<221> NAME/KEY: misc_feature
<222> LOCATION: (6)..(6)
<223> OTHER INFORMATION: Xaa is D, N, S, or Y
<220> FEATURE:
<221> NAME/KEY: misc_feature
<222> LOCATION: (7)..(7)
<223> OTHER INFORMATION: Xaa is present or absent and if present Xaa is
      D, G, or N
```

-continued

```
<220> FEATURE:
<221> NAME/KEY: misc_feature
<222> LOCATION: (8)..(8)
<223> OTHER INFORMATION: Xaa is present or absent and if present Xaa is
      G, N, or Y
<220> FEATURE:
<221> NAME/KEY: misc_feature
<222> LOCATION: (9)..(9)
<223> OTHER INFORMATION: Xaa is present or absent and if present Xaa is
      K, N, or S
<220> FEATURE:
<221> NAME/KEY: misc_feature
<222> LOCATION: (10)..(10)
<223> OTHER INFORMATION: Xaa is present or absent and if present Xaa is,
      F, Y, or T
<220> FEATURE:
<221> NAME/KEY: misc_feature
<222> LOCATION: (11)..(11)
<223> OTHER INFORMATION: Xaa is present or absent and if present Xaa is
      Y

<400> SEQUENCE: 24

Xaa Xaa Xaa Xaa Xaa Xaa Xaa Xaa Xaa Xaa Xaa
1               5                   10

<210> SEQ ID NO 25
<211> LENGTH: 3
<212> TYPE: PRT
<213> ORGANISM: Artificial Sequence
<220> FEATURE:
<223> OTHER INFORMATION: Formula L2
<220> FEATURE:
<221> NAME/KEY: misc_feature
<222> LOCATION: (1)..(1)
<223> OTHER INFORMATION: Xaa is D, L, R, T, or Y
<220> FEATURE:
<221> NAME/KEY: misc_feature
<222> LOCATION: (2)..(2)
<223> OTHER INFORMATION: Xaa is A, T, or V

<400> SEQUENCE: 25

Xaa Xaa Ser
1

<210> SEQ ID NO 26
<211> LENGTH: 9
<212> TYPE: PRT
<213> ORGANISM: Artificial Sequence
<220> FEATURE:
<223> OTHER INFORMATION: Formula L3
<220> FEATURE:
<221> NAME/KEY: misc_feature
<222> LOCATION: (1)..(1)
<223> OTHER INFORMATION: Xaa is S, Q, or W
<220> FEATURE:
<221> NAME/KEY: misc_feature
<222> LOCATION: (2)..(2)
<223> OTHER INFORMATION: Xaa is H, N, or Q
<220> FEATURE:
<221> NAME/KEY: misc_feature
<222> LOCATION: (3)..(3)
<223> OTHER INFORMATION: Xaa is D, G, S, or Y
<220> FEATURE:
<221> NAME/KEY: misc_feature
<222> LOCATION: (4)..(4)
<223> OTHER INFORMATION: Xaa is H, N, R, S, T, or Y
<220> FEATURE:
<221> NAME/KEY: misc_feature
<222> LOCATION: (5)..(5)
<223> OTHER INFORMATION: Xaa is E, H, K, R, S, or T
<220> FEATURE:
<221> NAME/KEY: misc_feature
<222> LOCATION: (6)..(6)
<223> OTHER INFORMATION: Xaa is D, F, L, S, V, or W
<220> FEATURE:
```

```
<221> NAME/KEY: misc_feature
<222> LOCATION: (8)..(8)
<223> OTHER INFORMATION: Xaa is L, P, W, or Y

<400> SEQUENCE: 26

Xaa Xaa Xaa Xaa Xaa Xaa Pro Xaa Thr
1               5

<210> SEQ ID NO 27
<211> LENGTH: 10
<212> TYPE: PRT
<213> ORGANISM: Artificial Sequence
<220> FEATURE:
<223> OTHER INFORMATION: 18F10 VH CDR1

<400> SEQUENCE: 27

Gly Phe Ser Leu Ser Thr Tyr Gly Ile Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: 13B5 VH CDR1

<400> SEQUENCE: 28

Gly Phe Ser Leu Thr Thr Ser Gly Leu Gly
1               5                   10

<210> SEQ ID NO 29
<211> LENGTH: 8
<212> TYPE: PRT
<213> ORGANISM: Artificial Sequence
<220> FEATURE:
<223> OTHER INFORMATION: 1B2 and 12E2 VH CDR1

<400> SEQUENCE: 29

Gly Phe Thr Phe Ser Asp Tyr Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: 21E9 VH CDR1

<400> SEQUENCE: 30

Gly Tyr Thr Phe Thr Ile Tyr Gly
1               5

<210> SEQ ID NO 31
<211> LENGTH: 8
<212> TYPE: PRT
<213> ORGANISM: Artificial Sequence
<220> FEATURE:
<223> OTHER INFORMATION: 2-80 VH CDR1

<400> SEQUENCE: 31

Gly Tyr Thr Phe Thr Asn Phe Gly
1               5

<210> SEQ ID NO 32
<211> LENGTH: 8
<212> TYPE: PRT
<213> ORGANISM: Artificial Sequence
```

-continued

```
<220> FEATURE:
<223> OTHER INFORMATION: 54E11 VH CDR1

<400> SEQUENCE: 32

Gly Tyr Thr Phe Thr Ser Tyr Gly
1               5

<210> SEQ ID NO 33
<211> LENGTH: 8
<212> TYPE: PRT
<213> ORGANISM: Artificial Sequence
<220> FEATURE:
<223> OTHER INFORMATION: 62-11 VH CDR1

<400> SEQUENCE: 33

Gly Tyr Thr Phe Thr Ser Tyr Trp
1               5

<210> SEQ ID NO 34
<211> LENGTH: 8
<212> TYPE: PRT
<213> ORGANISM: Artificial Sequence
<220> FEATURE:
<223> OTHER INFORMATION: 4A3 VH CDR1

<400> SEQUENCE: 34

Gly Tyr Thr Phe Thr Ile Tyr Trp
1               5

<210> SEQ ID NO 35
<211> LENGTH: 8
<212> TYPE: PRT
<213> ORGANISM: Artificial Sequence
<220> FEATURE:
<223> OTHER INFORMATION: 62-100 VH CDR1

<400> SEQUENCE: 35

Gly Tyr Thr Phe Thr Ser Tyr Trp
1               5

<210> SEQ ID NO 36
<211> LENGTH: 8
<212> TYPE: PRT
<213> ORGANISM: Artificial Sequence
<220> FEATURE:
<223> OTHER INFORMATION: 4A3 VH CDR2

<400> SEQUENCE: 36

Ile Asp Pro Ser Asp Ser Glu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: 62-11 VH CDR2

<400> SEQUENCE: 37

Ile Asp Pro Ser Asp Ser Glu Thr
1               5

<210> SEQ ID NO 38
<211> LENGTH: 8
<212> TYPE: PRT
<213> ORGANISM: Artificial Sequence
<220> FEATURE:
```

<223> OTHER INFORMATION: 62-100 VH CDR2

<400> SEQUENCE: 38

Ile Asp Pro Ser Asp Ser Glu Thr
1               5

<210> SEQ ID NO 39
<211> LENGTH: 8
<212> TYPE: PRT
<213> ORGANISM: Artificial Sequence
<220> FEATURE:
<223> OTHER INFORMATION: 21E9, 54E11, and 2-80 VH CDR2

<400> SEQUENCE: 39

Ile Asn Thr Tyr Thr Gly Glu Pro
1               5

<210> SEQ ID NO 40
<211> LENGTH: 8
<212> TYPE: PRT
<213> ORGANISM: Artificial Sequence
<220> FEATURE:
<223> OTHER INFORMATION: 1B2 VH CDR2

<400> SEQUENCE: 40

Ile Ser Asp Asp Gly Asn Tyr Thr
1               5

<210> SEQ ID NO 41
<211> LENGTH: 8
<212> TYPE: PRT
<213> ORGANISM: Artificial Sequence
<220> FEATURE:
<223> OTHER INFORMATION: 12E2 VH CDR2

<400> SEQUENCE: 41

Ile Ser Asn Gly Gly Gly Ser Thr
1               5

<210> SEQ ID NO 42
<211> LENGTH: 7
<212> TYPE: PRT
<213> ORGANISM: Artificial Sequence
<220> FEATURE:
<223> OTHER INFORMATION: 13B5 VH CDR2

<400> SEQUENCE: 42

Ile Trp Trp Asp Asp Asp Lys
1               5

<210> SEQ ID NO 43
<211> LENGTH: 7
<212> TYPE: PRT
<213> ORGANISM: Artificial Sequence
<220> FEATURE:
<223> OTHER INFORMATION: 18F10 VH CDR2

<400> SEQUENCE: 43

Ile Trp Trp Asn Asp Asn Lys
1               5

<210> SEQ ID NO 44
<211> LENGTH: 14
<212> TYPE: PRT
<213> ORGANISM: Artificial Sequence
<220> FEATURE:
<223> OTHER INFORMATION: 54E11 VH CDR3

<400> SEQUENCE: 44

Ala Arg Glu His Tyr Tyr Gly Ile Asn Pro Leu Leu Gly Cys
1               5                   10

<210> SEQ ID NO 45
<211> LENGTH: 11
<212> TYPE: PRT
<213> ORGANISM: Artificial Sequence
<220> FEATURE:
<223> OTHER INFORMATION: 1B2 VH CDR3

<400> SEQUENCE: 45

Ala Arg Gly Trp Leu Leu Pro Val Phe Ala Tyr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: 21E9 VH CDR3

<400> SEQUENCE: 46

Ala Arg Lys Gly Tyr Tyr Gly Ser Ser Gly Tyr Phe Asp Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: 2-80 VH CDR3

<400> SEQUENCE: 47

Ala Arg Arg Gly Asp Gly Leu Tyr Ser Met Asp Tyr
1               5                   10

<210> SEQ ID NO 48
<211> LENGTH: 8
<212> TYPE: PRT
<213> ORGANISM: Artificial Sequence
<220> FEATURE:
<223> OTHER INFORMATION: 18F10 VH CDR3

<400> SEQUENCE: 48

Ala Arg Thr Gly Tyr Phe Asp Val
1               5

<210> SEQ ID NO 49
<211> LENGTH: 9
<212> TYPE: PRT
<213> ORGANISM: Artificial Sequence
<220> FEATURE:
<223> OTHER INFORMATION: 62-11 and 62-100 VH CDR3

<400> SEQUENCE: 49

Ser Asn Gly Tyr Ser Ser Phe Ala Tyr
1               5

<210> SEQ ID NO 50
<211> LENGTH: 15
<212> TYPE: PRT
<213> ORGANISM: Artificial Sequence
<220> FEATURE:
<223> OTHER INFORMATION: 12E2 VH CDR3

-continued

```
<400> SEQUENCE: 50

Val Arg Pro Lys Arg Asp Phe Gln Tyr Leu Tyr Ala Met Asp Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: 13B5 VH CDR3

<400> SEQUENCE: 51

Val Arg Ser Leu Tyr Asp Tyr Asp Glu Gly Tyr Tyr Phe Asp Ser
1               5                   10                  15

<210> SEQ ID NO 52
<211> LENGTH: 8
<212> TYPE: PRT
<213> ORGANISM: Artificial Sequence
<220> FEATURE:
<223> OTHER INFORMATION: 4A3 VH CDR3

<400> SEQUENCE: 52

Ala Ser Ser Gly Thr Gly Ala Tyr
1               5

<210> SEQ ID NO 53
<211> LENGTH: 10
<212> TYPE: PRT
<213> ORGANISM: Artificial Sequence
<220> FEATURE:
<223> OTHER INFORMATION: 2-80 VL CDR1

<400> SEQUENCE: 53

Glu Ser Ile Asp Ser Tyr Gly Asn Ser Phe
1               5                   10

<210> SEQ ID NO 54
<211> LENGTH: 10
<212> TYPE: PRT
<213> ORGANISM: Artificial Sequence
<220> FEATURE:
<223> OTHER INFORMATION: 12E2 VL CDR1

<400> SEQUENCE: 54

Lys Ser Val Ser Thr Ser Gly Tyr Ser Tyr
1               5                   10

<210> SEQ ID NO 55
<211> LENGTH: 6
<212> TYPE: PRT
<213> ORGANISM: Artificial Sequence
<220> FEATURE:
<223> OTHER INFORMATION: 54E11 and 62-11 VL CDR1

<400> SEQUENCE: 55

Gln Gly Ile Ser Asn Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: 1B2 VL CDR1

<400> SEQUENCE: 56
```

```
Gln Ser Ile Gly Asn Asn
1               5
```

```
<210> SEQ ID NO 57
<211> LENGTH: 6
<212> TYPE: PRT
<213> ORGANISM: Artificial Sequence
<220> FEATURE:
<223> OTHER INFORMATION: 13B5 VL CDR1

<400> SEQUENCE: 57
```

```
Gln Ser Ile Ser Asp Tyr
1               5
```

```
<210> SEQ ID NO 58
<211> LENGTH: 11
<212> TYPE: PRT
<213> ORGANISM: Artificial Sequence
<220> FEATURE:
<223> OTHER INFORMATION: 18F10 VL CDR1

<400> SEQUENCE: 58
```

```
Gln Ser Leu Val His Ser Asn Gly Asn Thr Tyr
1               5                   10
```

```
<210> SEQ ID NO 59
<211> LENGTH: 6
<212> TYPE: PRT
<213> ORGANISM: Artificial Sequence
<220> FEATURE:
<223> OTHER INFORMATION: 21E9 VL CDR1

<400> SEQUENCE: 59
```

```
Gln Ser Val Ser Asn Asp
1               5
```

```
<210> SEQ ID NO 60
<211> LENGTH: 6
<212> TYPE: PRT
<213> ORGANISM: Artificial Sequence
<220> FEATURE:
<223> OTHER INFORMATION: 62-100 VL CDR1

<400> SEQUENCE: 60
```

```
Gln Ser Ile Ser Asn Asn
1               5
```

```
<210> SEQ ID NO 61
<211> LENGTH: 11
<212> TYPE: PRT
<213> ORGANISM: Artificial Sequence
<220> FEATURE:
<223> OTHER INFORMATION: 4A3 VL CDR1

<400> SEQUENCE: 61
```

```
Gln Ser Leu Leu Asp Ser Asp Gly Lys Thr Tyr
1               5                   10
```

```
<210> SEQ ID NO 62
<211> LENGTH: 3
<212> TYPE: PRT
<213> ORGANISM: Artificial Sequence
<220> FEATURE:
<223> OTHER INFORMATION: 54E11 and 62-11 VL CDR2

<400> SEQUENCE: 62
```

```
Asp Thr Ser
1

<210> SEQ ID NO 63
<211> LENGTH: 3
<212> TYPE: PRT
<213> ORGANISM: Artificial Sequence
<220> FEATURE:
<223> OTHER INFORMATION: 12E2 VL CDR2

<400> SEQUENCE: 63

Leu Ala Ser
1

<210> SEQ ID NO 64
<211> LENGTH: 3
<212> TYPE: PRT
<213> ORGANISM: Artificial Sequence
<220> FEATURE:
<223> OTHER INFORMATION: 2-80 VL CDR2

<400> SEQUENCE: 64

Arg Ala Ser
1

<210> SEQ ID NO 65
<211> LENGTH: 3
<212> TYPE: PRT
<213> ORGANISM: Artificial Sequence
<220> FEATURE:
<223> OTHER INFORMATION: 18F10 VL CDR2

<400> SEQUENCE: 65

Thr Val Ser
1

<210> SEQ ID NO 66
<211> LENGTH: 3
<212> TYPE: PRT
<213> ORGANISM: Artificial Sequence
<220> FEATURE:
<223> OTHER INFORMATION: 21E9, 13B5, and 62-100 VL CDR2

<400> SEQUENCE: 66

Tyr Ala Ser
1

<210> SEQ ID NO 67
<211> LENGTH: 3
<212> TYPE: PRT
<213> ORGANISM: Artificial Sequence
<220> FEATURE:
<223> OTHER INFORMATION: 1B2 VL CDR2

<400> SEQUENCE: 67

Tyr Thr Ser
1

<210> SEQ ID NO 68
<211> LENGTH: 3
<212> TYPE: PRT
<213> ORGANISM: Artificial Sequence
<220> FEATURE:
<223> OTHER INFORMATION: 4A3 VL CDR2

<400> SEQUENCE: 68

Leu Val Ser
```

-continued

1

<210> SEQ ID NO 69
<211> LENGTH: 9
<212> TYPE: PRT
<213> ORGANISM: Artificial Sequence
<220> FEATURE:
<223> OTHER INFORMATION: 12E2 VL CDR3

<400> SEQUENCE: 69

Gln His Ser Arg Glu Leu Pro Trp Thr
1               5

<210> SEQ ID NO 70
<211> LENGTH: 9
<212> TYPE: PRT
<213> ORGANISM: Artificial Sequence
<220> FEATURE:
<223> OTHER INFORMATION: 13B5 VL CDR3

<400> SEQUENCE: 70

Gln Asn Gly His Thr Phe Pro Pro Thr
1               5

<210> SEQ ID NO 71
<211> LENGTH: 9
<212> TYPE: PRT
<213> ORGANISM: Artificial Sequence
<220> FEATURE:
<223> OTHER INFORMATION: 21E9 VL CDR3

<400> SEQUENCE: 71

Gln Gln Asp Tyr Ser Ser Pro Trp Thr
1               5

<210> SEQ ID NO 72
<211> LENGTH: 9
<212> TYPE: PRT
<213> ORGANISM: Artificial Sequence
<220> FEATURE:
<223> OTHER INFORMATION: 2-80 VL CDR3

<400> SEQUENCE: 72

Gln Gln Ser Asn Glu Asp Pro Leu Thr
1               5

<210> SEQ ID NO 73
<211> LENGTH: 9
<212> TYPE: PRT
<213> ORGANISM: Artificial Sequence
<220> FEATURE:
<223> OTHER INFORMATION: 1B2 VL CDR3

<400> SEQUENCE: 73

Gln Gln Ser Asn Arg Trp Pro Trp Thr
1               5

<210> SEQ ID NO 74
<211> LENGTH: 9
<212> TYPE: PRT
<213> ORGANISM: Artificial Sequence
<220> FEATURE:
<223> OTHER INFORMATION: 54E11 and 62-11 VL CDR3

<400> SEQUENCE: 74

Gln Gln Tyr Ser Lys Leu Pro Tyr Thr
1               5

```
<210> SEQ ID NO 75
<211> LENGTH: 9
<212> TYPE: PRT
<213> ORGANISM: Artificial Sequence
<220> FEATURE:
<223> OTHER INFORMATION: 18F10 VL CDR3

<400> SEQUENCE: 75

Ser Gln Ser Thr His Val Pro Tyr Thr
1               5

<210> SEQ ID NO 76
<211> LENGTH: 9
<212> TYPE: PRT
<213> ORGANISM: Artificial Sequence
<220> FEATURE:
<223> OTHER INFORMATION: 62-100 VL CDR3

<400> SEQUENCE: 76

Gln Gln Ser Asn Ser Trp Pro Leu Thr
1               5

<210> SEQ ID NO 77
<211> LENGTH: 9
<212> TYPE: PRT
<213> ORGANISM: Artificial Sequence
<220> FEATURE:
<223> OTHER INFORMATION: 4A3 VL CDR3

<400> SEQUENCE: 77

Trp Gln Gly Thr His Phe Pro Tyr Thr
1               5

<210> SEQ ID NO 78
<211> LENGTH: 22
<212> TYPE: PRT
<213> ORGANISM: Artificial Sequence
<220> FEATURE:
<223> OTHER INFORMATION: Leader Sequence

<400> SEQUENCE: 78

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 79
<211> LENGTH: 16
<212> TYPE: PRT
<213> ORGANISM: Artificial Sequence
<220> FEATURE:
<223> OTHER INFORMATION: Flexible Linker

<400> SEQUENCE: 79

Ser Gly Gly Gly Gly Ser Gly Gly Gly Ser Gly Gly Gly Gly Ser
1               5                   10                  15

<210> SEQ ID NO 80
<211> LENGTH: 229
<212> TYPE: PRT
<213> ORGANISM: Artificial Sequence
<220> FEATURE:
<223> OTHER INFORMATION: IgG4 hinge-CH2-CH3 region spacer

<400> SEQUENCE: 80
```

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

```
<210> SEQ ID NO 81
<211> LENGTH: 25
<212> TYPE: PRT
<213> ORGANISM: Artificial Sequence
<220> FEATURE:
<223> OTHER INFORMATION: CD8 transmembrane region

<400> SEQUENCE: 81

Asp Ile Tyr Ile Trp Ala Pro Leu Ala Gly Thr Cys Gly Val Leu Leu
1               5                   10                  15

Leu Ser Leu Val Ile Thr Leu Tyr Cys
            20                  25
```

```
<210> SEQ ID NO 82
<211> LENGTH: 42
<212> TYPE: PRT
<213> ORGANISM: Artificial Sequence
<220> FEATURE:
<223> OTHER INFORMATION: 4-1BB co-signaling region

<400> SEQUENCE: 82

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

-continued

```
<210> SEQ ID NO 83
<211> LENGTH: 112
<212> TYPE: PRT
<213> ORGANISM: Artificial Sequence
<220> FEATURE:
<223> OTHER INFORMATION: CD3 zeta signaling region

<400> SEQUENCE: 83

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 84
<211> LENGTH: 671
<212> TYPE: PRT
<213> ORGANISM: Artificial Sequence
<220> FEATURE:
<223> OTHER INFORMATION: 1B2_CAR

<400> SEQUENCE: 84

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Val
                20                  25                  30

Leu Val Lys Pro Gly Gly Ser Leu Lys Leu Ser Cys Ala Ala Ser Gly
            35                  40                  45

Phe Thr Phe Ser Asp Tyr Tyr Met Tyr Trp Val Arg Gln Thr Pro Glu
        50                  55                  60

Lys Arg Leu Glu Trp Val Ala Thr Ile Ser Asp Asp Gly Asn Tyr Thr
65                  70                  75                  80

Asn Tyr Pro Asp Ser Val Lys Gly Arg Phe Thr Ile Ser Arg Asp Asn
                85                  90                  95

Ala Lys Asn Asn Leu Tyr Leu Gln Met Ser Ser Leu Lys Ser Glu Asp
                100                 105                 110

Thr Ala Met Tyr Tyr Cys Ala Arg Gly Trp Leu Leu Pro Val Phe Ala
            115                 120                 125

Tyr Trp Gly Gln Gly Thr Leu Val Thr Val Ser Ala Ser Gly Gly Gly
        130                 135                 140

Gly Ser Gly Gly Gly Gly Ser Gly Gly Gly Gly Ser Asp Ile Val Leu
145                 150                 155                 160

Thr Gln Ser Pro Ala Thr Leu Ser Val Thr Pro Gly Asp Ser Val Ser
                165                 170                 175

Leu Ser Cys Arg Ala Ser Gln Ser Ile Gly Asn Asn Leu His Trp Tyr
                180                 185                 190

Gln Gln Lys Ser His Glu Ser Pro Arg Leu Leu Ile Lys Tyr Thr Ser
```

-continued

```
                195                 200                 205

Gln Ser Ile Ser Gly Ile Pro Ser Arg Phe Ser Gly Ser Gly Ser Gly
    210                 215                 220

Thr Asp Phe Thr Leu Asn Ile Asn Ser Val Glu Thr Glu Asp Phe Gly
225                 230                 235                 240

Val Tyr Phe Cys Gln Gln Ser Asn Arg Trp Pro Trp Thr Phe Gly Gly
                245                 250                 255

Gly Thr Lys Leu Glu Ile Lys Glu Ser Lys Tyr Gly Pro Pro Cys Pro
                260                 265                 270

Pro Cys Pro Ala Pro Glu Phe Leu Gly Gly Pro Ser Val Phe Leu Phe
                275                 280                 285

Pro Pro Lys Pro Lys Asp Thr Leu Met Ile Ser Arg Thr Pro Glu Val
    290                 295                 300

Thr Cys Val Val Val Asp Val Ser Gln Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Tyr Arg Val Val Ser Val Leu Thr
                340                 345                 350

Val Leu His Gln Asp Trp Leu Asn Gly Lys Glu Tyr Lys Cys Lys Val
                355                 360                 365

Ser Asn Lys Gly Leu Pro Ser Ser Ile Glu Lys Thr Ile Ser Lys Ala
    370                 375                 380

Lys Gly Gln Pro Arg Glu Pro Gln Val Tyr Thr Leu Pro Pro Ser Gln
385                 390                 395                 400

Glu Glu Met Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
                420                 425                 430

Glu Asn Asn Tyr Lys Thr Thr Pro Pro Val Leu Asp Ser Asp Gly Ser
    435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Asp Ile Tyr Ile
                485                 490                 495

Trp Ala Pro Leu Ala Gly Thr Cys Gly Val Leu Leu Leu Ser Leu Val
                500                 505                 510

Ile Thr Leu Tyr Cys Lys Arg Gly Arg Lys Lys Leu Leu Tyr Ile Phe
                515                 520                 525

Lys Gln Pro Phe Met Arg Pro Val Gln Thr Thr Gln Glu Glu Asp Gly
    530                 535                 540

Cys Ser Cys Arg Phe Pro Glu Glu Glu Glu Gly Gly Cys Glu Leu Arg
545                 550                 555                 560

Val Lys Phe Ser Arg Ser Ala Asp Ala Pro Ala Tyr Lys Gln Gly Gln
                565                 570                 575

Asn Gln Leu Tyr Asn Glu Leu Asn Leu Gly Arg Arg Glu Glu Tyr Asp
                580                 585                 590

Val Leu Asp Lys Arg Arg Gly Arg Asp Pro Glu Met Gly Gly Lys Pro
                595                 600                 605

Arg Arg Lys Asn Pro Gln Glu Gly Leu Tyr Asn Glu Leu Gln Lys Asp
    610                 615                 620
```

-continued

Lys Met Ala Glu Ala Tyr Ser Glu Ile Gly Met Lys Gly Glu Arg Arg
625                 630                 635                 640

Arg Gly Lys Gly His Asp Gly Leu Tyr Gln Gly Leu Ser Thr Ala Thr
                    645                 650                 655

Lys Asp Thr Tyr Asp Ala Leu His Met Gln Ala Leu Pro Pro Arg
            660                 665                 670

<210> SEQ ID NO 85
<211> LENGTH: 676
<212> TYPE: PRT
<213> ORGANISM: Artificial Sequence
<220> FEATURE:
<223> OTHER INFORMATION: 2-80_CAR

<400> SEQUENCE: 85

Met Leu Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
                20                  25                  30

Leu Lys Lys Pro Gly Glu Thr Val Lys Ile Ser Cys Lys Ala Ser Gly
            35                  40                  45

Tyr Thr Phe Thr Asn Phe Gly Met Asn Trp Val Lys Gln Ala Pro Gly
        50                  55                  60

Lys Gly Leu Lys Trp Met Gly Trp Ile Asn Thr Tyr Thr Gly Glu Pro
65                  70                  75                  80

Thr Tyr Ala Asp Asp Phe Lys Gly Arg Phe Ala Phe Ser Leu Glu Thr
                85                  90                  95

Ser Ala Ser Thr Ala Ser Leu Gln Ile Asn Asn Leu Lys Asn Glu Asp
            100                 105                 110

Thr Ala Thr Tyr Phe Cys Ala Arg Arg Gly Asp Gly Leu Tyr Ser Met
            115                 120                 125

Asp Tyr Trp Gly Gln Gly Thr Ser Val Thr Val Ser Ser Ser Gly Gly
        130                 135                 140

Gly Gly Ser Gly Gly Gly Gly Ser Gly Gly Gly Gly Ser Asp Ile Val
145                 150                 155                 160

Leu Thr Gln Ser Pro Ala Ser Leu Ala Val Ser Leu Gly Gln Arg Ala
                165                 170                 175

Thr Ile Ser Cys Arg Ala Ser Glu Ser Ile Asp Ser Tyr Gly Asn Ser
            180                 185                 190

Phe Met Tyr Trp Tyr Gln Gln Lys Pro Gly Gln Pro Pro Lys Leu Leu
            195                 200                 205

Ile Tyr Arg Ala Ser Asn Leu Glu Ser Gly Ile Pro Ala Arg Phe Ser
        210                 215                 220

Gly Ser Gly Ser Arg Thr Asp Phe Thr Leu Thr Ile Asn Pro Val Glu
225                 230                 235                 240

Ala Asp Asp Val Ala Thr Tyr Tyr Cys Gln Gln Ser Asn Glu Asp Pro
                245                 250                 255

Leu Thr Phe Gly Ala Gly Thr Lys Leu Glu Leu Lys Glu Ser Lys Tyr
            260                 265                 270

Gly Pro Pro Cys Pro Pro Cys Pro Ala Pro Glu Phe Leu Gly Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser Gln Glu Asp
305                 310                 315                 320

-continued

```
Pro Glu Val Gln Phe Asn Trp Tyr Val Asp Gly Val Glu Val His Asn
            325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Gly Leu Pro Ser Ser Ile Glu Lys
        370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
            405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Arg Leu Thr Val Asp Lys
        450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
            485                 490                 495

Lys Asp Ile Tyr Ile Trp Ala Pro Leu Ala Gly Thr Cys Gly Val Leu
            500                 505                 510

Leu Leu Ser Leu Val Ile Thr Leu Tyr Cys Lys Arg Gly Arg Lys Lys
            515                 520                 525

Leu Leu Tyr Ile Phe Lys Gln Pro Phe Met Arg Pro Val Gln Thr Thr
            530                 535                 540

Gln Glu Glu Asp Gly Cys Ser Cys Arg Phe Pro Glu Glu Glu Glu Gly
545                 550                 555                 560

Gly Cys Glu Leu Arg Val Lys Phe Ser Arg Ser Ala Asp Ala Pro Ala
            565                 570                 575

Tyr Lys Gln Gly Gln Asn Gln Leu Tyr Asn Glu Leu Asn Leu Gly Arg
            580                 585                 590

Arg Glu Glu Tyr Asp Val Leu Asp Lys Arg Arg Gly Arg Asp Pro Glu
            595                 600                 605

Met Gly Gly Lys Pro Arg Arg Lys Asn Pro Gln Glu Gly Leu Tyr Asn
            610                 615                 620

Glu Leu Gln Lys Asp Lys Met Ala Glu Ala Tyr Ser Glu Ile Gly Met
625                 630                 635                 640

Lys Gly Glu Arg Arg Arg Gly Lys Gly His Asp Gly Leu Tyr Gln Gly
            645                 650                 655

Leu Ser Thr Ala Thr Lys Asp Thr Tyr Asp Ala Leu His Met Gln Ala
            660                 665                 670

Leu Pro Pro Arg
            675
```

```
<210> SEQ ID NO 86
<211> LENGTH: 679
<212> TYPE: PRT
<213> ORGANISM: Artificial Sequence
<220> FEATURE:
<223> OTHER INFORMATION: 12E2_CAR

<400> SEQUENCE: 86
```

```
Met Leu Leu Leu Val Thr Ser Leu Leu Leu Cys Glu Leu Pro His Pro
1               5                   10                  15

Ala Phe Leu Leu Ile Pro Glu Val Lys Leu Val Glu Ser Gly Gly Gly
            20                  25                  30

Leu Val Gln Pro Gly Gly Ser Leu Lys Leu Ser Cys Ala Thr Ser Gly
        35                  40                  45

Phe Thr Phe Ser Asp Tyr Tyr Met Phe Trp Val Arg Gln Thr Pro Glu
    50                  55                  60

Lys Lys Leu Glu Trp Val Ala Tyr Ile Ser Asn Gly Gly Gly Ser Thr
65                  70                  75                  80

Tyr Tyr Pro Asp Thr Val Lys Gly Arg Phe Thr Ile Ser Arg Asp Asn
                85                  90                  95

Asp Lys Asn Thr Leu Tyr Leu Gln Met Ser Arg Leu Lys Ser Asp Asp
            100                 105                 110

Thr Ala Leu Tyr Tyr Cys Val Arg Pro Lys Arg Asp Phe Gln Tyr Leu
        115                 120                 125

Tyr Ala Met Asp Tyr Trp Gly Gln Gly Thr Ser Val Thr Val Ser Ser
    130                 135                 140

Ser Gly Gly Gly Gly Ser Gly Gly Gly Gly Ser Gly Gly Gly Gly Ser
145                 150                 155                 160

Asp Ile Val Leu Thr Gln Ser Pro Ala Ser Leu Ala Val Ser Leu Gly
            165                 170                 175

Gln Arg Ala Thr Ile Ser Cys Arg Ala Ser Lys Ser Val Ser Thr Ser
            180                 185                 190

Gly Tyr Ser Tyr Met His Trp Tyr Gln Gln Lys Pro Gly Gln Ser Pro
        195                 200                 205

Lys Leu Leu Ile Tyr Leu Ala Ser Asn Leu Glu Ser Gly Val Pro Ala
    210                 215                 220

Arg Phe Ser Gly Ser Gly Ser Gly Thr Asp Phe Thr Leu Asn Ile His
225                 230                 235                 240

Pro Val Glu Asp Glu Asp Ala Ala Thr Tyr Tyr Cys Gln His Ser Arg
            245                 250                 255

Glu Leu Pro Trp Thr Phe Gly Gly Gly Thr Lys Leu Glu Ile Lys Glu
            260                 265                 270

Ser Lys Tyr Gly Pro Pro Cys Pro Pro Cys Pro Ala Pro Glu Phe Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

Gln Glu Asp Pro Glu Val Gln Phe Asn Trp Tyr Val Asp Gly Val Glu
            325                 330                 335

Val His Asn Ala Lys Thr Lys Pro Arg Glu Glu Gln Phe Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Gly Leu Pro Ser Ser
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
                405                 410                 415
```

-continued

```
Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Arg Leu Thr
            450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Leu Gly Lys Asp Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
            515                 520                 525

Arg Lys Lys Leu Leu Tyr Ile Phe Lys Gln Pro Phe Met Arg Pro Val
            530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
                565                 570                 575

Ala Pro Ala Tyr Lys Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
            595                 600                 605

Asp Pro Glu Met Gly Gly Lys Pro Arg Arg Lys Asn Pro Gln Glu Gly
            610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
            675
```

```
<210> SEQ ID NO 87
<211> LENGTH: 676
<212> TYPE: PRT
<213> ORGANISM: Artificial Sequence
<220> FEATURE:
<223> OTHER INFORMATION: 13B5_CAR

<400> SEQUENCE: 87

Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Gly
            20                  25                  30

Ile Leu Lys Pro Ser Gln Thr Leu Ser Leu Thr Cys Ser Phe Ser Gly
            35                  40                  45

Phe Ser Leu Thr Thr Ser Gly Leu Gly Val Gly Trp Ile Arg Gln Pro
            50                  55                  60

Ser Gly Lys Gly Leu Glu Trp Leu Ala His Ile Trp Trp Asp Asp Asp
65                  70                  75                  80

Lys Tyr Phe Asn Pro Ser Leu Arg Asn Gln Leu Thr Ile Ser Lys Asp
                85                  90                  95
```

-continued

```
Thr Ser Arg Asn Gln Val Phe Leu Glu Ile Thr Ser Val Thr Thr Ala
            100                 105                 110

Asp Thr Ala Thr Tyr Tyr Cys Val Arg Ser Leu Tyr Asp Tyr Asp Glu
            115                 120                 125

Gly Tyr Tyr Phe Asp Ser Trp Gly Gln Gly Thr Thr Leu Thr Val Ser
    130                 135                 140

Ser Ser Gly Gly Gly Gly Ser Gly Gly Gly Gly Ser Gly Gly Gly Gly
145                 150                 155                 160

Ser Glu Ile Val Met Ile Gln Ser Pro Ala Thr Leu Ser Val Asn Pro
                165                 170                 175

Gly Asp Arg Val Ser Leu Ser Cys Arg Ala Ser Gln Ser Ile Ser Asp
            180                 185                 190

Tyr Leu His Trp Tyr Gln Gln Lys Ser His Glu Ser Pro Arg Leu Leu
            195                 200                 205

Ile Lys Tyr Ala Ser Gln Ser Ile Ser Gly Ile Pro Ser Arg Phe Ser
    210                 215                 220

Gly Ser Gly Ser Gly Ser Asp Phe Thr Leu Ser Ile Asn Ser Val Glu
225                 230                 235                 240

Pro Glu Asp Val Gly Val Tyr Tyr Cys Gln Asn Gly His Thr Phe Pro
                245                 250                 255

Pro Thr Phe Gly Gly Gly Thr Lys Leu Glu Ile Lys Glu Ser Lys Tyr
            260                 265                 270

Gly Pro Pro Cys Pro Pro Cys Pro Ala Pro Glu Phe Leu Gly Gly Pro
            275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser Gln Glu Asp
305                 310                 315                 320

Pro Glu Val Gln Phe Asn Trp Tyr Val Asp Gly Val Glu Val His Asn
                325                 330                 335

Ala Lys Thr Lys Pro Arg Glu Glu Gln Phe Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Gly Leu Pro Ser Ser Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Gln Glu Glu Met Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Arg Leu Thr Val Asp Lys
    450                 455                 460

Ser Arg Trp Gln Glu Gly Asn Val Phe Ser Cys Ser Val Met His Glu
465                 470                 475                 480

Ala Leu His Asn His Tyr Thr Gln Lys Ser Leu Ser Leu Ser Leu Gly
                485                 490                 495

Lys Asp Ile Tyr Ile Trp Ala Pro Leu Ala Gly Thr Cys Gly Val Leu
            500                 505                 510

Leu Leu Ser Leu Val Ile Thr Leu Tyr Cys Lys Arg Gly Arg Lys Lys
```

-continued

```
               515                    520                    525
Leu Leu Tyr Ile Phe Lys Gln Pro Phe Met Arg Pro Val Gln Thr Thr
       530                    535                    540

Gln Glu Glu Asp Gly Cys Ser Cys Arg Phe Pro Glu Glu Glu Glu Gly
545                    550                    555                    560

Gly Cys Glu Leu Arg Val Lys Phe Ser Arg Ser Ala Asp Ala Pro Ala
                   565                    570                    575

Tyr Lys Gln Gly Gln Asn Gln Leu Tyr Asn Glu Leu Asn Leu Gly Arg
                   580                    585                    590

Arg Glu Glu Tyr Asp Val Leu Asp Lys Arg Arg Gly Arg Asp Pro Glu
               595                    600                    605

Met Gly Gly Lys Pro Arg Arg Lys Asn Pro Gln Glu Gly Leu Tyr Asn
           610                    615                    620

Glu Leu Gln Lys Asp Lys Met Ala Glu Ala Tyr Ser Glu Ile Gly Met
625                    630                    635                    640

Lys Gly Glu Arg Arg Arg Gly Lys Gly His Asp Gly Leu Tyr Gln Gly
                   645                    650                    655

Leu Ser Thr Ala Thr Lys Asp Thr Tyr Asp Ala Leu His Met Gln Ala
                   660                    665                    670

Leu Pro Pro Arg
           675

<210> SEQ ID NO 88
<211> LENGTH: 674
<212> TYPE: PRT
<213> ORGANISM: Artificial Sequence
<220> FEATURE:
<223> OTHER INFORMATION: 18F10_CAR

<400> SEQUENCE: 88

Met Leu Leu Leu Val Thr Ser Leu Leu Leu Cys Glu Leu Pro His Pro
1                   5                    10                    15

Ala Phe Leu Leu Ile Pro Gln Val Thr Leu Lys Glu Ser Gly Pro Gly
               20                    25                    30

Ile Leu Gln Pro Ser Gln Thr Leu Ser Leu Thr Cys Ser Phe Ser Gly
           35                    40                    45

Phe Ser Leu Ser Thr Tyr Gly Ile Gly Ile Gly Trp Ile Arg Gln Pro
       50                    55                    60

Ser Gly Lys Gly Leu Glu Trp Leu Ala His Ile Trp Trp Asn Asp Asn
65                    70                    75                    80

Lys Asn Tyr Asn Thr Ala Leu Lys Ser Arg Leu Thr Ile Ser Lys Asp
                   85                    90                    95

Pro Ser Asn Asn Gln Val Phe Leu Lys Ile Ala Ser Val Asp Thr Ala
               100                    105                    110

Asp Thr Ala Thr Tyr Phe Cys Ala Arg Thr Gly Tyr Phe Asp Val Trp
           115                    120                    125

Gly Ala Gly Thr Thr Val Thr Val Ser Ser Gly Gly Gly Gly Ser
       130                    135                    140

Gly Gly Gly Gly Ser Gly Gly Gly Ser Asp Val Val Leu Thr Gln
145                    150                    155                    160

Thr Pro Leu Ser Leu Pro Val Ser Leu Gly Asp Gln Val Ser Ile Ser
                   165                    170                    175

Cys Ser Ser Ser Gln Ser Leu Val His Ser Asn Gly Asn Thr Tyr Ile
               180                    185                    190

His Trp Tyr Leu Gln Lys Pro Gly Gln Ser Pro Lys Leu Leu Ile Tyr
```

-continued

```
            195             200             205
Thr Val Ser Asn Arg Phe Ser Gly Val Pro Asp Arg Phe Ser Gly Ser
    210             215             220

Gly Ser Gly Thr Asp Phe Thr Leu Lys Ile Ser Arg Val Glu Ala Glu
225             230             235             240

Asp Leu Gly Leu Tyr Phe Cys Ser Gln Ser Thr His Val Pro Tyr Thr
                245             250             255

Phe Gly Gly Gly Thr Lys Leu Glu Ile Lys Glu Ser Lys Tyr Gly Pro
                260             265             270

Pro Cys Pro Pro Cys Pro Ala Pro Glu Phe Leu Gly Gly Pro Ser Val
                275             280             285

Phe Leu Phe Pro Pro Lys Pro Lys Asp Thr Leu Met Ile Ser Arg Thr
    290             295             300

Pro Glu Val Thr Cys Val Val Val Asp Val Ser Gln Glu Asp Pro Glu
305             310             315             320

Val Gln Phe Asn Trp Tyr Val Asp Gly Val Glu Val His Asn Ala Lys
                325             330             335

Thr Lys Pro Arg Glu Glu Gln Phe Asn Ser Thr Tyr Arg Val Val Ser
                340             345             350

Val Leu Thr Val Leu His Gln Asp Trp Leu Asn Gly Lys Glu Tyr Lys
                355             360             365

Cys Lys Val Ser Asn Lys Gly Leu Pro Ser Ser Ile Glu Lys Thr Ile
    370             375             380

Ser Lys Ala Lys Gly Gln Pro Arg Glu Pro Gln Val Tyr Thr Leu Pro
385             390             395             400

Pro Ser Gln Glu Glu Met Thr Lys Asn Gln Val Ser Leu Thr Cys Leu
                405             410             415

Val Lys Gly Phe Tyr Pro Ser Asp Ile Ala Val Glu Trp Glu Ser Asn
                420             425             430

Gly Gln Pro Glu Asn Asn Tyr Lys Thr Thr Pro Pro Val Leu Asp Ser
                435             440             445

Asp Gly Ser Phe Phe Leu Tyr Ser Arg Leu Thr Val Asp Lys Ser Arg
    450             455             460

Trp Gln Glu Gly Asn Val Phe Ser Cys Ser Val Met His Glu Ala Leu
465             470             475             480

His Asn His Tyr Thr Gln Lys Ser Leu Ser Leu Ser Leu Gly Lys Asp
                485             490             495

Ile Tyr Ile Trp Ala Pro Leu Ala Gly Thr Cys Gly Val Leu Leu Leu
                500             505             510

Ser Leu Val Ile Thr Leu Tyr Cys Lys Arg Gly Arg Lys Lys Leu Leu
                515             520             525

Tyr Ile Phe Lys Gln Pro Phe Met Arg Pro Val Gln Thr Thr Gln Glu
    530             535             540

Glu Asp Gly Cys Ser Cys Arg Phe Pro Glu Glu Glu Glu Gly Gly Cys
545             550             555             560

Glu Leu Arg Val Lys Phe Ser Arg Ser Ala Asp Ala Pro Ala Tyr Lys
                565             570             575

Gln Gly Gln Asn Gln Leu Tyr Asn Glu Leu Asn Leu Gly Arg Arg Glu
                580             585             590

Glu Tyr Asp Val Leu Asp Lys Arg Arg Gly Arg Asp Pro Glu Met Gly
                595             600             605

Gly Lys Pro Arg Arg Lys Asn Pro Gln Glu Gly Leu Tyr Asn Glu Leu
    610             615             620
```

-continued

```
Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
                660                 665                 670

Pro Arg

<210> SEQ ID NO 89
<211> LENGTH: 674
<212> TYPE: PRT
<213> ORGANISM: Artificial Sequence
<220> FEATURE:
<223> OTHER INFORMATION: 21E9_CAR

<400> SEQUENCE: 89

Met Leu Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
                20                  25                  30

Leu Lys Lys Pro Gly Glu Thr Val Lys Ile Ser Cys Lys Ala Ser Gly
            35                  40                  45

Tyr Thr Phe Thr Ile Tyr Gly Met Asn Trp Val Lys Gln Ala Pro Gly
        50                  55                  60

Lys Gly Leu Lys Trp Met Gly Trp Ile Asn Thr Tyr Thr Gly Glu Pro
65                  70                  75                  80

Thr Tyr Ala Asp Asp Phe Arg Gly Arg Phe Ala Phe Ser Leu Glu Thr
                85                  90                  95

Ser Ala Ser Thr Ala Tyr Leu Gln Ile Asn Asn Leu Lys Asn Glu Asp
                100                 105                 110

Thr Ala Thr Tyr Phe Cys Ala Arg Lys Gly Tyr Tyr Gly Ser Ser Gly
            115                 120                 125

Tyr Phe Asp Tyr Trp Gly Gln Gly Thr Thr Leu Thr Val Ser Ser Ser
        130                 135                 140

Gly Gly Gly Gly Ser Gly Gly Gly Gly Ser Gly Gly Gly Gly Ser Ser
145                 150                 155                 160

Ile Val Met Thr Gln Thr Pro Lys Phe Leu Leu Val Ser Ala Gly Asp
                165                 170                 175

Arg Val Thr Ile Thr Cys Lys Ala Ser Gln Ser Val Ser Asn Asp Val
            180                 185                 190

Ser Trp Tyr Gln Gln Lys Pro Gly Gln Ser Pro Lys Leu Leu Ile Tyr
        195                 200                 205

Tyr Ala Ser Asn Arg Tyr Thr Gly Val Pro Asp Arg Phe Thr Gly Ser
        210                 215                 220

Gly Tyr Gly Thr Asp Phe Thr Phe Thr Ile Ser Thr Val Gln Ala Glu
225                 230                 235                 240

Asp Leu Ala Val Tyr Phe Cys Gln Gln Asp Tyr Ser Ser Pro Trp Thr
                245                 250                 255

Phe Gly Gly Gly Thr Lys Leu Glu Ile Lys Glu Ser Lys Tyr Gly Pro
                260                 265                 270

Pro Cys Pro Pro Cys Pro Ala Pro Glu Phe Leu Gly Gly Pro Ser Val
            275                 280                 285

Phe Leu Phe Pro Pro Lys Pro Lys Asp Thr Leu Met Ile Ser Arg Thr
        290                 295                 300
```

-continued

```
Pro Glu Val Thr Cys Val Val Val Asp Val Ser Gln Glu Asp Pro Glu
305             310             315             320

Val Gln Phe Asn Trp Tyr Val Asp Gly Val Glu Val His Asn Ala Lys
                325             330             335

Thr Lys Pro Arg Glu Glu Gln Phe Asn Ser Thr Tyr Arg Val Val Ser
            340             345             350

Val Leu Thr Val Leu His Gln Asp Trp Leu Asn Gly Lys Glu Tyr Lys
            355             360             365

Cys Lys Val Ser Asn Lys Gly Leu Pro Ser Ser Ile Glu Lys Thr Ile
    370             375             380

Ser Lys Ala Lys Gly Gln Pro Arg Glu Pro Gln Val Tyr Thr Leu Pro
385             390             395             400

Pro Ser Gln Glu Glu Met Thr Lys Asn Gln Val Ser Leu Thr Cys Leu
                405             410             415

Val Lys Gly Phe Tyr Pro Ser Asp Ile Ala Val Glu Trp Glu Ser Asn
            420             425             430

Gly Gln Pro Glu Asn Asn Tyr Lys Thr Thr Pro Pro Val Leu Asp Ser
            435             440             445

Asp Gly Ser Phe Phe Leu Tyr Ser Arg Leu Thr Val Asp Lys Ser Arg
    450             455             460

Trp Gln Glu Gly Asn Val Phe Ser Cys Ser Val Met His Glu Ala Leu
465             470             475             480

His Asn His Tyr Thr Gln Lys Ser Leu Ser Leu Ser Leu Gly Lys Asp
                485             490             495

Ile Tyr Ile Trp Ala Pro Leu Ala Gly Thr Cys Gly Val Leu Leu Leu
            500             505             510

Ser Leu Val Ile Thr Leu Tyr Cys Lys Arg Gly Arg Lys Lys Leu Leu
            515             520             525

Tyr Ile Phe Lys Gln Pro Phe Met Arg Pro Val Gln Thr Thr Gln Glu
    530             535             540

Glu Asp Gly Cys Ser Cys Arg Phe Pro Glu Glu Glu Glu Gly Gly Cys
545             550             555             560

Glu Leu Arg Val Lys Phe Ser Arg Ser Ala Asp Ala Pro Ala Tyr Lys
                565             570             575

Gln Gly Gln Asn Gln Leu Tyr Asn Glu Leu Asn Leu Gly Arg Arg Glu
            580             585             590

Glu Tyr Asp Val Leu Asp Lys Arg Arg Gly Arg Asp Pro Glu Met Gly
            595             600             605

Gly Lys Pro Arg Arg Lys Asn Pro Gln Glu Gly Leu Tyr Asn Glu Leu
    610             615             620

Gln Lys Asp Lys Met Ala Glu Ala Tyr Ser Glu Ile Gly Met Lys Gly
625             630             635             640

Glu Arg Arg Arg Gly Lys Gly His Asp Gly Leu Tyr Gln Gly Leu Ser
                645             650             655

Thr Ala Thr Lys Asp Thr Tyr Asp Ala Leu His Met Gln Ala Leu Pro
            660             665             670

Pro Arg
```

```
<210> SEQ ID NO 90
<211> LENGTH: 674
<212> TYPE: PRT
<213> ORGANISM: Artificial Sequence
<220> FEATURE:
<223> OTHER INFORMATION: 21F6_54E11_CAR
```

US 12,624,083 B2

93

94

-continued

<400> SEQUENCE: 90

Met Leu Leu Leu Val Thr Ser Leu Leu Leu Cys Glu Leu Pro His Pro
1               5                   10                  15

Ala Phe Leu Leu Ile Pro Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Ser Tyr Gly Met Asn Trp Val Lys Gln Ala Pro Gly
    50                  55                  60

Lys Gly Leu Lys Trp Met Gly Trp Ile Asn Thr Tyr Thr Gly Glu Pro
65                  70                  75                  80

Thr Tyr Ala Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Thr Ala Thr Tyr Phe Cys Ala Arg Glu His Tyr Tyr Gly Ile Asn Pro
            115                 120                 125

Leu Leu Gly Cys Trp Gly Gln Gly Thr Thr Leu Thr Val Ser Ser Ser
    130                 135                 140

Gly Gly Gly Gly Ser Gly Gly Gly Ser Gly Gly Gly Ser Asp
145                 150                 155                 160

Ile Gln Met Thr Gln Thr Thr Ser Ser Leu Ser Ala Ser Leu Gly Asp
                165                 170                 175

Arg Val Thr Ile Ser Cys Ser Ala Ser Gln Gly Ile Ser Asn Tyr Leu
            180                 185                 190

Asn Trp Tyr Gln Gln Lys Pro Asp Gly Thr Val Lys Leu Leu Ile Tyr
            195                 200                 205

Asp Thr Ser Ser Leu His Ser Gly Val Pro Ser Arg Phe Ser Gly Ser
    210                 215                 220

Gly Ser Gly Thr Asp Tyr Ser Leu Thr Ile Ser Asn Leu Glu Pro Glu
225                 230                 235                 240

Asp Ile Ala Thr Tyr Tyr Cys Gln Gln Tyr Ser Lys Leu Pro Tyr Thr
                245                 250                 255

Phe Gly Gly Gly Thr Lys Leu Glu Ile Lys Glu Ser Lys Tyr Gly Pro
            260                 265                 270

Pro Cys Pro Pro Cys Pro Ala Pro Glu Phe Leu Gly Gly Pro Ser Val
            275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Asn Ser Thr Tyr Arg Val Val Ser
            340                 345                 350

Val Leu Thr Val Leu His Gln Asp Trp Leu Asn Gly Lys Glu Tyr Lys
            355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

-continued

```
Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
            435                 440                 445

Asp Gly Ser Phe Phe Leu Tyr Ser Arg Leu Thr Val Asp Lys Ser Arg
        450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Asp
                485                 490                 495

Ile Tyr Ile Trp Ala Pro Leu Ala Gly Thr Cys Gly Val Leu Leu Leu
            500                 505                 510

Ser Leu Val Ile Thr Leu Tyr Cys Lys Arg Gly Arg Lys Lys Leu Leu
            515                 520                 525

Tyr Ile Phe Lys Gln Pro Phe Met Arg Pro Val Gln Thr Thr Gln Glu
            530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Lys
                565                 570                 575

Gln Gly Gln Asn Gln Leu Tyr Asn Glu Leu Asn Leu Gly Arg Arg Glu
            580                 585                 590

Glu Tyr Asp Val Leu Asp Lys Arg Arg Gly Arg Asp Pro Glu Met Gly
            595                 600                 605

Gly Lys Pro Arg Arg Lys Asn Pro Gln Glu Gly Leu Tyr Asn Glu Leu
            610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
                645                 650                 655

Thr Ala Thr Lys Asp Thr Tyr Asp Ala Leu His Met Gln Ala Leu Pro
                660                 665                 670

Pro Arg
```

```
<210> SEQ ID NO 91
<211> LENGTH: 669
<212> TYPE: PRT
<213> ORGANISM: Artificial Sequence
<220> FEATURE:
<223> OTHER INFORMATION: 62-11_CAR

<400> SEQUENCE: 91
```

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Pro Gly Ala Glu
            20                  25                  30

Leu Val Arg Pro Gly Ala Ser Val Lys Leu Ser Cys Lys Ala Ser Gly
            35                  40                  45

Tyr Thr Phe Thr Ser Tyr Trp Met Asn Trp Val Lys Gln Arg Pro Gly
        50                  55                  60

Gln Gly Leu Glu Trp Ile Gly Met Ile Asp Pro Ser Asp Ser Glu Thr
65                  70                  75                  80

His Tyr Asn Gln Met Phe Lys Asp Lys Ala Thr Leu Thr Val Asp Lys
                85                  90                  95
```

Ser Ser Ser Thr Ala Tyr Met Gln Leu Ser Ser Leu Thr Ser Glu Asp
                100                 105                 110

Ser Ala Val Tyr Tyr Cys Ser Asn Gly Tyr Ser Ser Phe Ala Tyr Trp
            115                 120                 125

Gly Gln Gly Thr Leu Val Thr Val Ser Ser Ser Gly Gly Gly Gly Ser
    130                 135                 140

Gly Gly Gly Gly Ser Gly Gly Gly Ser Asp Ile Gln Met Thr Gln
145                 150                 155                 160

Thr Thr Ser Ser Leu Ser Ala Ser Leu Gly Asp Arg Val Thr Ile Ser
                165                 170                 175

Cys Ser Ala Ser Gln Gly Ile Ser Asn Tyr Leu Asn Trp Tyr Gln Gln
            180                 185                 190

Lys Pro Asp Gly Thr Val Lys Leu Leu Ile Tyr Asp Thr Ser Ser Leu
        195                 200                 205

His Ser Gly Val Pro Ser Arg Phe Ser Gly Ser Gly Ser Gly Thr Asp
    210                 215                 220

Tyr Ser Leu Thr Ile Ser Asn Leu Glu Pro Glu Asp Ile Ala Thr Tyr
225                 230                 235                 240

Tyr Cys Gln Gln Tyr Ser Lys Leu Pro Tyr Thr Phe Gly Gly Gly Thr
            245                 250                 255

Lys Leu Glu Ile Lys Glu Ser Lys Tyr Gly Pro Pro Cys Pro Pro Cys
            260                 265                 270

Pro Ala Pro Glu Phe Leu Gly Gly Pro Ser Val Phe Leu Phe Pro Pro
        275                 280                 285

Lys Pro Lys Asp Thr Leu Met Ile Ser Arg Thr Pro Glu Val Thr Cys
        290                 295                 300

Val Val Val Asp Val Ser Gln Glu Asp Pro Glu Val Gln Phe Asn Trp
305                 310                 315                 320

Tyr Val Asp Gly Val Glu Val His Asn Ala Lys Thr Lys Pro Arg Glu
            325                 330                 335

Glu Gln Phe Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Gly Leu Pro Ser Ser Ile Glu Lys Thr Ile Ser Lys Ala Lys Gly
    370                 375                 380

Gln Pro Arg Glu Pro Gln Val Tyr Thr Leu Pro Pro Ser Gln Glu Glu
385                 390                 395                 400

Met Thr Lys Asn Gln Val Ser Leu Thr Cys Leu Val Lys Gly Phe Tyr
            405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
            435                 440                 445

Leu Tyr Ser Arg Leu Thr Val Asp Lys Ser Arg Trp Gln Glu Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Leu Gly Lys Asp Ile Tyr Ile Trp Ala
            485                 490                 495

Pro Leu Ala Gly Thr Cys Gly Val Leu Leu Leu Ser Leu Val Ile Thr
            500                 505                 510

Leu Tyr Cys Lys Arg Gly Arg Lys Lys Leu Leu Tyr Ile Phe Lys Gln

-continued

```
            515              520              525
Pro Phe Met Arg Pro Val Gln Thr Thr Gln Glu Glu Asp Gly Cys Ser
    530              535              540

Cys Arg Phe Pro Glu Glu Glu Glu Gly Gly Cys Glu Leu Arg Val Lys
545              550              555              560

Phe Ser Arg Ser Ala Asp Ala Pro Ala Tyr Lys Gln Gly Gln Asn Gln
            565              570              575

Leu Tyr Asn Glu Leu Asn Leu Gly Arg Arg Glu Glu Tyr Asp Val Leu
            580              585              590

Asp Lys Arg Arg Gly Arg Asp Pro Glu Met Gly Gly Lys Pro Arg Arg
        595              600              605

Lys Asn Pro Gln Glu Gly Leu Tyr Asn Glu Leu Gln Lys Asp Lys Met
    610              615              620

Ala Glu Ala Tyr Ser Glu Ile Gly Met Lys Gly Glu Arg Arg Arg Gly
625              630              635              640

Lys Gly His Asp Gly Leu Tyr Gln Gly Leu Ser Thr Ala Thr Lys Asp
            645              650              655

Thr Tyr Asp Ala Leu His Met Gln Ala Leu Pro Pro Arg
            660              665
```

CHIMERIC ANTIGEN RECEPTORS AGAINST HUMAN CYTOMEGALOVIRUS

CROSS-REFERENCE TO RELATED APPLICATIONS

This application claims the benefit of U.S. Patent Application No. 62/914,408, filed Oct. 11, 2019, which is herein incorporated by reference in its entirety.

ACKNOWLEDGEMENT OF GOVERNMENT SUPPORT

This invention was made with Government support under Grant Number AI103960, awarded by the National Institutes of Health. The Government has certain rights in the invention.

REFERENCE TO A SEQUENCE LISTING SUBMITTED VIA EFS-WEB

The content of the ASCII text file of the sequence listing named "20201012_034044_209WO1_ST25" which is 85.9 kb in size was created on Oct. 7, 2020 and electronically submitted via EFS-Web herewith the application is incorporated herein by reference in its entirety.

BACKGROUND OF THE INVENTION

1. Field of the Invention Compositions and methods for treating cytomegalovirus infections.

2. Description of the Related Art

Human cytomegalovirus (CMV) infection is widespread, ranging from about 60% of adults in the US to nearly 100% in other parts of the world. In most healthy persons, infection is lifelong but immunologically contained and asymptomatic. Some perinatally infected persons, and persons who are significantly immunosuppressed (due to AIDS or iatrogenic/ therapeutic immunosuppression for conditions such as bone marrow or organ transplantation) can develop disseminated infection with significant morbidity and mortality due to end organ damage.

The major arm of immunity controlling CMV infection in healthy hosts is cellular immunity, particularly CD8+ T lymphocytes (C8TLs). Autologous immunotherapy using expanded CMV-specific C8TLs has provided proof-of-concept that C8TLs can treat CMV in immunocompromised hosts, but this approach is not generally applicable due to various technical limitations. On the other hand, gene therapy with a chimeric antigen receptor (CAR) targeted against CMV could be readily applied to generate CMV-specific C8TLs in patients, analogous to the growing use of CAR T-cell gene therapy for various cancers.

To date only one CMV-specific CAR has been reported in the literature, and it has not been advanced to clinical trials to our knowledge.

SUMMARY OF THE INVENTION

"CMV-specific CARs": In some embodiments, the present invention is directed to a cytomegalovirus specific chimeric antigen receptor (CMV-specific CAR), which comprises a single chain antibody sequence or fragment thereof having SEQ ID NO: 21, SEQ ID NO: 22, SEQ ID NO: 23, SEQ ID NO: 24, SEQ ID NO: 25, and SEQ ID NO: 26 as follows: G-X1-X2-X3-X4-X5-X6-X7-X8-X9 Formula H1 (SEQ ID NO: 21), wherein, X1 is F or Y, X2 is S or T, X3 is L or F, X4 is S or T, X5 is D, I, N, S, or T, X6 is F, Y, or S, X7 is G, Y, or W, X8 is present or absent and if present X8 is L or I, and, X9 is present or absent and if present X9 is G; I-X10-X11-X12-X13-X14-X15-X16 Formula H2 (SEQ ID NO: 22), wherein, X10 is D, N, S, or W, X11 is D, N, P, T, or W, X12 is D, G, N, Y, or S, X13 is D, G, or T, X14 is D, G, N, or S, X15 is E, K, S, or Y, and, X16 is present or absent and if present X16 is P or T; X17-X18-X19-X20-X21-X22-X23-X24-X25-X26-X27-X28-X29-X30-X31 Formula H3 (SEQ ID NO: 23), wherein, X17 is A, S, or V, X18 is R, N, or S, X19 is E, G, K, P, R, or S, X20 is G, H, K, L, Y, or W, X21 is D, L, R, S, or Y, X22 is D, F, G, L, S, or Y, X23 is A, D, F, G, L, P, or Y, X24 is A, D, I, Q, S, V, or Y, X25 is present or absent and if present X25 is E, F, N, S, or Y, X26 is present or absent and if present X26 is A, G, M, L, or P is, X27 present or absent and if present X27 is D, L, or Y, X28 is present or absent and if present X28 is A, F, L, or Y, X29 is present or absent and if present X29 is D, F, G, or M, X30 is present or absent and if present X30 is C, D, or Y, and, X31 is present or absent and if present X31 is S or Y; X32-X33-X34-X35-X36-X37-X38-X39-X40-X41-X42 Formula L1 (SEQ ID NO: 24), wherein, X32 is E, K, or Q, X33 is G or S, X34 is I, L, or V, X35 is D, G, S, or V, X36 is D, H, N, S, or T, X37 is D, N, S, or Y, X38 is present or absent and if present X38 is D, G, or N, X39 is present or absent and if present X39 is G, N, or Y, X40 is present or absent and if present X40 is K, N, or S, X41 is present or absent and if present X41 is F, Y, or T, and, X42 is present or absent and if present X42 is Y; X43-X44-S Formula L2 (SEQ ID NO: 25), wherein, X43 is D, L, R, T, or Y, and, X44 is A, T, or V; X45-X46-X47-X48-X49-X50-P-X51-T Formula L3 (SEQ ID NO: 26), wherein, X45 is S, Q, or W, X46 is H, N, or Q, X47 is D, G, S, or Y, X48 is H, N, R, S, T, or Y, X49 is E, H, K, R, S, or T, X50 is D, F, L, S, V, or W, and, X51 is L, P, W, or Y. In some embodiments, a) Formula H1 (SEQ ID NO: 21) is GFSLSTYGIG (SEQ ID NO: 27), GFSLTTSGLG (SEQ ID NO: 28), GFTFSDYY (SEQ ID NO: 29), GYTFTIYG (SEQ ID NO: 30), GYTFTNFG (SEQ ID NO: 31), GYTFTSYG (SEQ ID NO: 32), GYTFTSYW (SEQ ID NO: 33), GYTFTIYW (SEQ ID NO: 34), or GYTFTSYW (SEQ ID NO: 35); b) Formula H2 (SEQ ID NO: 22) is IDPSDSET (SEQ ID NO: 36), IDPSD-SET (SEQ ID NO: 37), IDPSDSET (SEQ ID NO: 38), INTYTGEP (SEQ ID NO: 39), ISDDGNYT (SEQ ID NO: 40), ISNGGGST (SEQ ID NO: 41), IWWDDDK (SEQ ID NO: 42), or IWWNDNK (SEQ ID NO: 43); c) Formula H3 (SEQ ID NO: 23) is AREHYYGINPLLGC (SEQ ID NO: 44), ARGWLLPVFAY (SEQ ID NO: 45), ARKGYYGSSGYFDY (SEQ ID NO: 46), ARRGDG-LYSMDY (SEQ ID NO: 47), ARTGYFDV (SEQ ID NO: 48), SNGYSSFAY (SEQ ID NO: 49), VRPKRDFQY-LYAMDY (SEQ ID NO: 50), VRSLYDYDEGYYFDS (SEQ ID NO: 51), or ASSGTGAY (SEQ ID NO: 52); d) Formula L1 (SEQ ID NO: 24) is ESIDSYGNSF (SEQ ID NO: 53), KSVSTSGYSY (SEQ ID NO: 54), QGISNY (SEQ ID NO: 55), QSIGNN (SEQ ID NO: 56), QSISDY (SEQ ID NO: 57), QSLVHSNGNTY (SEQ ID NO: 58), QSVSND (SEQ ID NO: 59), QSISNN (SEQ ID NO: 60), or QSLL-DSDGKTY (SEQ ID NO: 61); e) Formula L2 (SEQ ID NO: 25) is DTS (SEQ ID NO: 62), LAS (SEQ ID NO: 63), RAS (SEQ ID NO: 64), TVS (SEQ ID NO: 65), YAS (SEQ ID NO: 66), YTS (SEQ ID NO: 67), or LVS (SEQ ID NO: 68); and/or f) Formula L3 (SEQ ID NO: 26) is QHSRELPWT (SEQ ID NO: 69), QNGHTFPPT (SEQ ID NO: 70), QQD-YSSPWT (SEQ ID NO: 71), QQSNEDPLT (SEQ ID NO:

72), QQSNRWPWT (SEQ ID NO: 73), QQYSKLPYT (SEQ ID NO: 74), SQSTHVPYT (SEQ ID NO: 75), QQSN-SWPLT (SEQ ID NO: 76), or WQGTHFPYT (SEQ ID NO: 77). In some embodiments, Formula H2 (SEQ ID NO: 22) is INTYTGEP (SEQ ID NO: 39) and Formula L2 (SEQ ID NO: 25) is YAS (SEQ ID NO: 66). In some embodiments, the single chain antibody or fragment thereof comprises SEQ ID NO: 30 with 0, 1, 2, or 3 amino acid substitutions, additions, or deletions, SEQ ID NO: 39 with 0, 1, 2, or 3 amino acid substitutions, additions, or deletions, SEQ ID NO: 46 with 0, 1, 2, or 3 amino acid substitutions, additions, or deletions, SEQ ID NO: 59 with 0, 1, 2, or 3 amino acid substitutions, additions, or deletions, SEQ ID NO: 66 with 0, 1, or 2 amino acid substitutions, additions, or deletions, and SEQ ID NO: 71 with 0, 1, 2, or 3 amino acid substitutions, additions, or deletions. In some embodiments, the single chain antibody or fragment thereof comprises SEQ ID NO: 30, SEQ ID NO: 39, SEQ ID NO: 46, SEQ ID NO: 59, SEQ ID NO: 66, and SEQ ID NO: 71. In some embodiments, the single chain antibody or fragment thereof comprises or consists of a VH chain and a VL chain selected from those set forth in Table 1. In some embodiments, the single chain antibody or fragment thereof comprises or consists of SEQ ID NO: 11 and SEQ ID NO: 12. In some embodiments, the CMV-specific CAR comprises or consists of SEQ ID NO: 84, SEQ ID NO: 85, SEQ ID NO: 86, SEQ ID NO: 87, SEQ ID NO: 88, SEQ ID NO: 89, SEQ ID NO: 90, or SEQ ID NO: 91, preferably SEQ ID NO: 89.

In some embodiments, the present invention is directed to a nucleic acid molecule that encodes a CMV-specific CAR as described herein, such as those described in the section entitled "CMV-specific CARs" above.

In some embodiments, the present invention is directed to an expression vector comprising a nucleic acid molecule that encodes a CMV-specific CAR as described herein, such as those described in the section entitled "CMV-specific CARs" above.

In some embodiments, the present invention is directed to a host cell or a progeny cell thereof comprising one or more expression vectors as described herein. In some embodiments, the host cell or the progeny cell is a CD8+ T lymphocyte, hematopoietic stem cell, or a hematopoietic progenitor cell. In some embodiments, the host cell or the progeny cell expresses one or more chimeric antigen receptors encoded by the one or more expression vectors.

In some embodiments, the present invention is directed to a method of treating, reducing, or inhibiting an infection by a cytomegalovirus in a subject, which comprises administering to the subject (a) an expression vector that encodes a CMV-specific CAR as described herein, such as those described in the section entitled "CMV-specific CARs" above, or (b) one or more cells that are transduced with the expression vector.

In some embodiments, the present invention is directed to a method of treating, reducing, or inhibiting an infection by a cytomegalovirus in a subject, which comprises administering to the subject (a) an expression vector that encodes a CMV-specific CAR as described herein, such as those described in the section entitled "CMV-specific CARs" above, or (b) one or more cells that are transduced with the expression vector.

In some embodiments, the present invention is directed to a method of treating, reducing, or inhibiting an infection by a cytomegalovirus in a subject, which comprises transplanting one or more cells that express one or more CMV-specific CARs as described herein, such as those described in the section entitled "CMV-specific CARs" above to the subject.

In some embodiments, the present invention is directed to a method of treating, reducing, or inhibiting an infection by a cytomegalovirus in a subject, which comprises transplanting one or more host cells or progeny cells thereof as described herein in the subject.

In some embodiments, the present invention is directed to a method of killing cells infected with a cytomegalovirus, which comprises contacting the infected cells with one or more cells (a) that express one or more CMV-specific CARs as described herein, such as those described in the section entitled "CMV-specific CARs" above, or (b) comprise an expression vector that encodes the one or more CMV-specific CARs.

In some embodiments, the present invention is directed to a method of reducing replication of a cytomegalovirus in a cell or a subject, which comprises contacting the cell with or administering to the subject one or more cells (a) that express one or more CMV-specific CARs as described herein, such as those described in the section entitled "CMV-specific CARs" above, or (b) comprise an expression vector that encodes the one or more CMV-specific CARs.

In some embodiments, the present invention is directed to (a) the use of one or more CMV-specific CARs as described herein, such as those described in the section entitled "CMV-specific CARs" above, (b) the use of one or more nucleic acid molecules that encode a CMV-specific CAR as described herein, such as those described in the section entitled "CMV-specific CARs" above, (c) the use of one or more expression vectors which comprise a nucleic acid molecule that encodes a CMV-specific CAR as described herein, such as those described in the section entitled "CMV-specific CARs" above, and/or (d) the use of one or more host cells or progeny thereof which comprises one or more expression vectors as described herein.

In some embodiments, the present invention is directed to (a) the use of one or more CMV-specific CARs as described herein, such as those described in the section entitled "CMV-specific CARs" above in the manufacture of a medicament for the treatment of a cytomegalovirus infection, (b) the use of one or more nucleic acid molecules that encode a CMV-specific CAR as described herein, such as those described in the section entitled "CMV-specific CARs" above in the manufacture of a medicament for the treatment of a cytomegalovirus infection, (c) the use of one or more expression vectors which comprise a nucleic acid molecule that encodes a CMV-specific CAR as described herein, such as those described in the section entitled "CMV-specific CARs" above in the manufacture of a medicament for the treatment of a cytomegalovirus infection, and/or (d) the use of one or more host cells or progeny thereof which comprises one or more expression vectors as described herein in the manufacture of a medicament for the treatment of a cytomegalovirus infection.

In some embodiments, the present invention is directed to (a) the use of one or more CMV-specific CARs as described herein, such as those described in the section entitled "CMV-specific CARs" above for the treatment of a cytomegalovirus infection, (b) the use of one or more nucleic acid molecules that encode a CMV-specific CAR as described herein, such as those described in the section entitled "CMV-specific CARs" above for the treatment of a cytomegalovirus infection, (c) the use of one or more expression vectors which comprise a nucleic acid molecule that encodes a CMV-specific CAR as described herein, such as those described in the section entitled "CMV-specific CARs" above for the treatment of a cytomegalovirus infection, and/or (d) the use of one or more host cells or progeny thereof which comprises one or more expression vectors as described herein for the treatment of a cytomegalovirus infection.

In some embodiments, the present invention is directed to (a) one or more CMV-specific CARs as described herein, such as those described in the section entitled "CMV-specific CARs" above, (b) one or more nucleic acid molecules that encode a CMV-specific CAR as described herein, such as those described in the section entitled "CMV-specific CARs" above, (c) one or more expression vectors which comprise a nucleic acid molecule that encodes a CMV-specific CAR as described herein, such as those described in the section entitled "CMV-specific CARs" above, and/or (d) one or more host cells or progeny thereof which comprises one or more expression vectors as described herein, for the treatment of a cytomegalovirus infection.

In some embodiments, the subject is human. In some embodiments, the subject has an immunodeficiency. In some embodiments the cytomegalovirus is a human cytomegalovirus.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description explain the principles of the invention.

DESCRIPTION OF THE DRAWINGS

This invention is further understood by reference to the drawings wherein:

FIG. 3: Schematic of an exemplary CAR construct.

FIG. 8: Representative dot plots are shown for production of both intracellular IFN-γ and TNF-α by untransduced (top row) or CAR-transduced (bottom row) C8TLs exposed to uninfected (left column) or acutely CMV TR-infected (right column) ARPE-19 cells.

FIG. 9: Representative histograms are shown for cell surface expression of CD107a on untransduced (top) or CAR-transduced (bottom) C8TLs exposed to uninfected (left histogram) or CMV TR-infected (right histogram) ARPE-19 cells.

FIG. 10: The net percentages of untransduced or CAR-transduced C8TLs producing both intracellular IFN-γ and TNF-α in response to CMV-infected target cells (after subtraction of the response to uninfected target cells) are plotted.

FIG. 11: The net percentages of untransduced or CAR-transduced C8TLs expressing cell surface CD107a after exposure to acutely CMV-infected ARPE-19 cells are plotted. Similar results were seen with CMV TB40/E-infected ARPE-19 cells (not shown). These results are representative of three experiments with three different C8TL donors; the other four CARs demonstrated minimal activity in two other experiments (not shown).

DETAILED DESCRIPTION OF THE INVENTION

Figure 1:
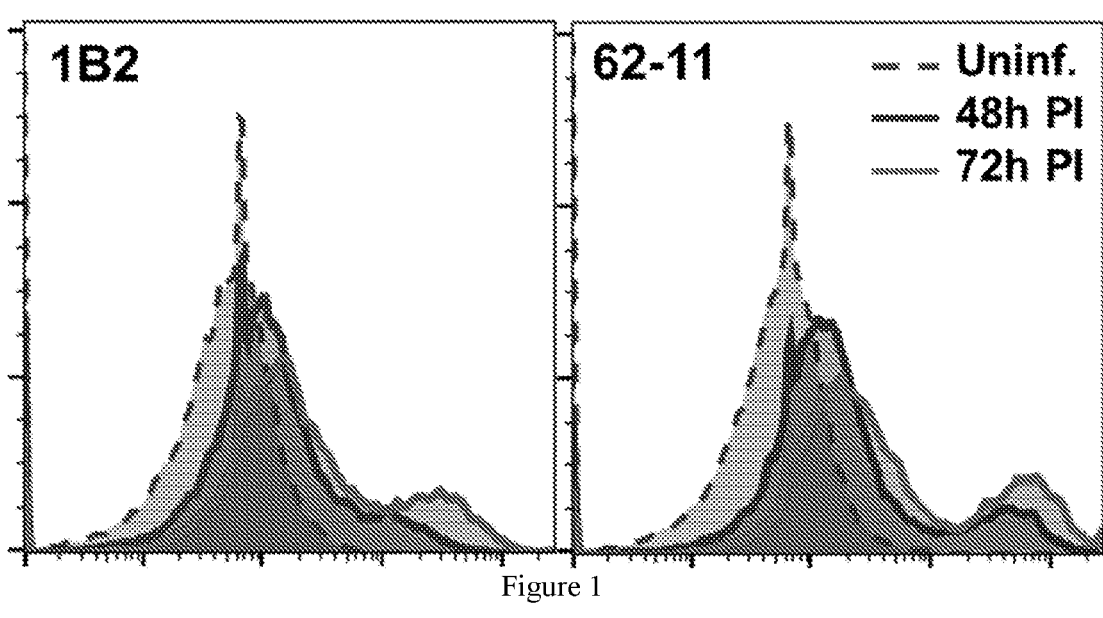
FIG. 1: NAb recognition of CMV-infected EpC. EpC were infected with CMV TB40/E (5 MOI). Cells were fixed and immune-stained with 1B2 (PC-specific) or 62-11 (gH-specific) NAb at 48 hours (middle curves) and 72 hours (right curves) post infection (PI). Controls were uninfected EpC (left curves).

CMV entry into fibroblasts (FB) and epithelial/endothelial cells (EpC/EnC) occurs by alternate routes of entry that are blocked by neutralizing antibodies (NAbs) of various potencies and cell type specificities. CMV infection of FB depends on the major essential envelope glycoprotein complexes (gC) gM/gN, gB, and gH/gL/gO. In contrast to FB entry, CMV infection of EpC/EnC requires an additional complex formed by gH/gL, UL128, UL130, and UL131A (PC). NAb targeting the major gCs block both CMV entry routes; however, NAb recognizing predominantly conformational epitopes formed by two or more of the UL128/UL130/UL131A (UL128/130/131A) subunits of the PC are unable to prevent FB entry, although they are able to interfere with EpC/EnC infection that dramatically exceeds that of NAb targeting the major gC. Both gH and PC-specific antibodies recognize gC expressed on the surface of CMV-infected cells (FIG. 1).

As disclosed herein, engineered cells expressing chimeric antigen receptors (CARs) specific against cytomegalovirus (CMV) exhibit activity against CMV-infected cells and suppress CMV replication. Specifically, primary CD8+ T lymphocytes (primary C8TLs) were transduced with CAR constructs encoding CARs specific against CMV (CMV-specific CARs). As used herein, "C8TLs" include naïve CD8+ T lymphocytes and cytotoxic T cells.

The exemplary CMV-specific CARs comprise a single chain antibody (SCA) or fragment thereof specific against a CMV antigen, a CH2-CH3 hinge region (e.g., from a human IgG4 antibody, a transmembrane domain (e.g., a CD8 transmembrane domain), and a CD3ζ intracellular domain with or without a costimulatory domain (e.g., from 4-1BB or CD28). See FIG. 2.

SCA sequences were derived from the gH and PC-specific NAbs disclosed in US20180230200; Lehmann et al. (2019) J Virol 93(17): e00931-19; Chiuppesi, et al. (2015) J Virol 89(23): 11884-98; and Wussow, et al. (2014) PLOS Pathog 10(11):e1004524, which are herein incorporated by reference in their entirety.

The amino acid sequences of the VH and VL chains (with the CDR sequences underlined) of the antibodies used to construct the SCA sequences of the exemplary CMV-specific CARs are provided in Table 1:

TABLE 1

| MAb Clone | SEQ ID NO: | Sequence |
|---|---|---|
| 1B2-VH | 1 | EVQLVESGGVLVKPGGSLKLSCAASGFTFSDYYMYWVRQTPEKRLE WVATISDDGNYTNYPDSVKGRFTISRDNAKNNLYLQMSSLKSEDTA MYYCARGWLLPVFAYWGQGTLVTVSA |
| 1B2-VL | 2 | DIVITQSPATLSVTPGDSVSLSCRASQSIGNNLHWYQQKSHESPRL LIKYTSQSISGIPSRFSGSGSGTDFTENINSVETEDFGVYFCQQSN RWPWTFGGGTKLEIK |
| 54E11-VH (21F6-VH) | 3 | QIQLVQSGPELKKPGETVKISCKASGYTFTSYGMNWVKQAPGKGLK WMGWINTYTGEPTYADDFKGRFAFSLETSASTAYLQINNLKNEDTA TYFCAREHYYGINPLLGCWGQGTTLTVSS |
| 54E11-VL (21F6-VL) | 4 | DIQMTQTTSSLSASLGDRVTISCSASQGISNYLNWYQQKPDGTVKL LIYDTSSLHSGVPSRFSGSGSGTDYSITISNLEPEDIATYYCQQYS KIPYTFGGGTKLEIK |
| 12E2-VH | 5 | EVKLVESGGGLVQPGGSLKLSCATSGFTFSDYYMFWVRQTPEKKLE WVAYISNGGGSTYYPDTVKGRFTISRDNDKNTLYLQMSRLKSDDTA LYYCVRPKRDFQYLYAMDYWGQGTSVTVSS |
| 12E2-VL | 6 | DIVITQSPASLAVSIGQRATISCRASKSVSTSGYSYMHWYQQKPGQ SPKLLIYLASNLESGVPARFSGSGSGTDETLNIHPVEDEDAATYYC QHSRELPWTFGGGTKLEIK |
| 13B5-VH | 7 | QVTLKESGPGILKPSQTLSLTCSFSGFSLTTSGLGVGWIRQPSGKG LEWLAHIWWDDDKYFNPSLRNQLTISKDTSRNQVFLEITSVTTADT ATYYCVRSLYDYDEGYYFDSWGQGTTLTVSS |
| 13B5-VL | 8 | EIVMIQSPATLSVNPGDRVSLSCRASQSISDYLHWYQQKSHESPRL LIKYASQSISGIPSRFSGSGSGSDFTLSINSVEPEDVGVYYCQNGH TFPPTFGGGTKLEIK |
| 18F10-VH | 9 | QVTLKESGPGILQPSQTLSLTCSFSGFSLSTYGIGIGWIRQPSGKG LEWLAHIWWNDNKNYNTALKSRLTISKDPSNNQVFLKIASVDTADT ATYFCARTGYFDVWGAGTTVTVSS |
| 18F10-VL | 10 | DVVLTQTPLSLPVSLGDQVSISCSSSQSLVHSNGNTYIHWYLQKPG QSPKLLIYTVSNRFSGVPDRFSGSGSGTDFTLKISRVEAEDLGLYF CSQSTHVPYTFGGGTKLEIK |
| 21E9-VH | 11 | QIQLVQSGPELKKPGETVKISCKASGYTFTIYGMNWVKQAPGKGLK WMGWINTYTGEPTYADDFRGRFAFSLETSASTAYLQINNLKNEDTA TYFCARKGYYGSSGYFDYWGQGTTLTVSS |
| 21E9-VL | 12 | SIVMTQTPKFLLVSAGDRVTITCKASQSVSNDVSWYQQKPGQSPKL LIYYASNRYTGVPDRFTGSGYGTDFTFTISTVQAEDLAVYFCQQDY SSPWTFGGGTKLEIK |

TABLE 1-continued

| MAb Clone | SEQ ID NO: | Sequence |
|---|---|---|
| 62-11-VH | 13 | QVQLQQPGAELVRPGASVKLSCKASGYTFTSYWMNWVKQRPGQGLE WIGMIDPSDSETHYNQMFKDKATLTVDKSSSTAYMQLSSLTSEDSA VYYCSNGYSSFAYWGQGTLVTVSV |
| 62-11-VL | 14 | D(V/I)QMTQTTSSLSASEGDRVTISCSASQGISNYLNWYQQKPDG TVKLLIYDTSSLHSGVPSRFSGSGSGTDYSLTISNLEPEDIATYYC QQYSKLPYTFGGGTKLEIK |
| 2-80-VH | 15 | QIQLVQSGPELKKPGETVKISCKASGYTFTNFGMNWVKQAPGKGLK WMGWINTYTGEPTYADDFKGRFAFSLETSASTASLQINNLKNEDTA TYFCARRGDGLYSMDYWGQGTSVTVSS |
| 2-80-VL | 16 | DIVLTQSPASLAVSLGQRATISCRASESIDSYGNSFMYWYQQKPGQ PPKLLIYRASNLESGIPARFSGSGSRTDFTLTINPVEADDVATYYC QQSNEDPLTFGAGTKLELK |
| 4A3-VH | 17 | QVQLQQPGPELVRPGASVKLSCKASGYTFTIYWMNWVKQRPGQGLE WIGMIDPSDSETHYNQMFKDKATLTVDKSSSTAYMQLSSLTSEDSA VYYCASSGTGAYWGQGTLLTVSA |
| 4A3-VL | 18 | DVVMTQTPLTLSVTIGQPASISCKSSQSLLDSDGKTYLNWLLQRPG QSPKRLIYLVSKLDSGVPDRFTGSGSGTDFTLKISRLEAEDLGVYY CWQGTHFPYTFGGGTKLEIK |
| 62-100-VH | 19 | QVQLQQPGAELVRPGASVKLSCKASGYTFTSYWMNWVKQRPGQGLE WIGMIDPSDSETHYNQMFKDKATLTVDKSSSTAYMQLSSLTSEDSA VYYCSNGYSSFAYWGQGTLVTVSV |
| 62-100-VL | 20 | DIVLTQSPATLSVTPGDSVSLSCRASQSISNNLHWYQQKSHESPRL LIKYASQSISGIPSRFSGSGSGTDFTLSINSVETEDFGKYVCQQSN SWPLTFGSGTKLEIK |

CAR constructs encoding CMV-specific CARs with the SCA sequences were produced. As used herein, a "CAR construct" refers to an expression vector designed to be capable of expression of a given CAR construct, such as a CMV-specific CAR, in a cell when provided therein. The CAR constructs were inserted into lentiviral vectors to deliver these CAR gene sequences to cells. FIG. 3 schematically shows an exemplary CAR construct.

Figure 4:
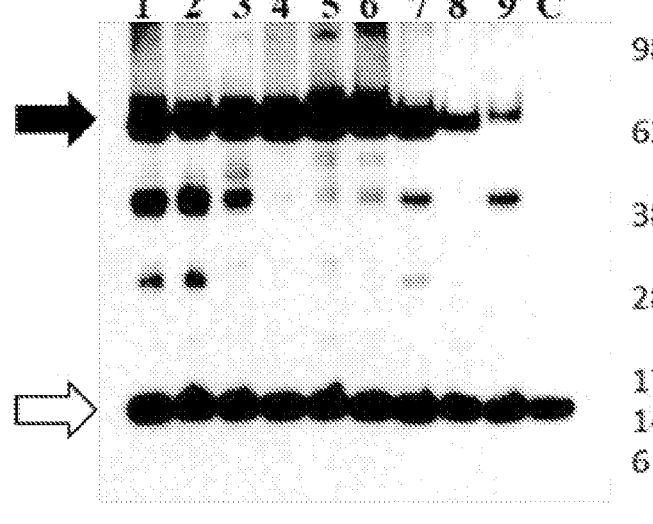
FIG. 4: CAR expression in transduced primary C8TLs by Western blot analysis. Primary C8TLs were transduced with lentiviral vectors delivering genes for the indicated CARs. Lysates were then assessed by Western blot staining for CD3ζ. The closed arrow indicates the approximate size of the CAR molecule containing CD3ζ, and the open arrow indicates the approximate size of native (unmodified) CD3ζ. Note that 21F6 and 54E11 CARs are identical duplicates.
Figure 5A:
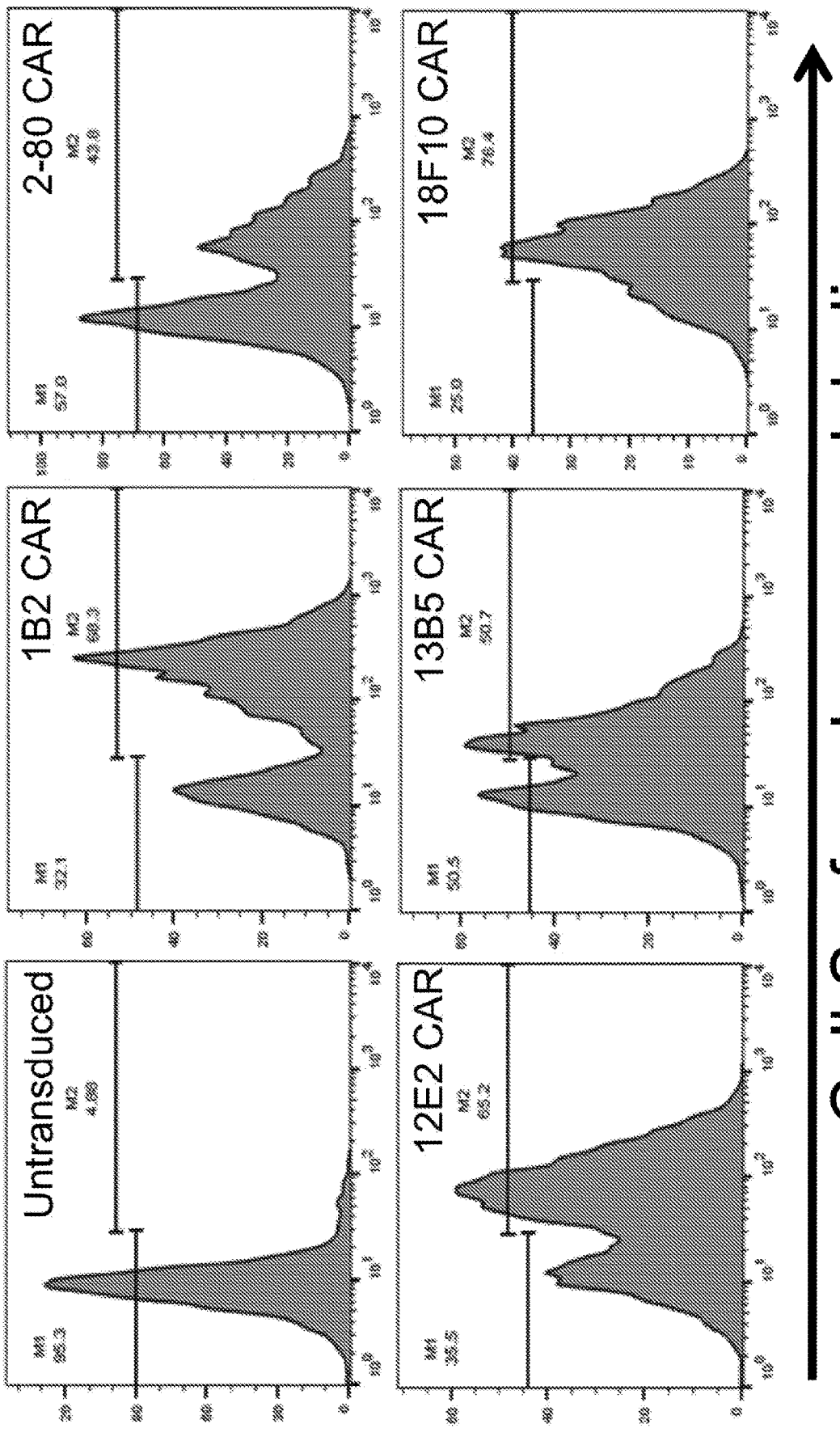
FIG. 5A: CAR expression in transduced primary C8TLs by flow cytometry. Primary C8TLs were transduced with lentiviral vectors delivering genes for the indicated CARs. The cells were then stained for cell surface human antibody expression and analyzed by flow cytometry.
Figure 5A:
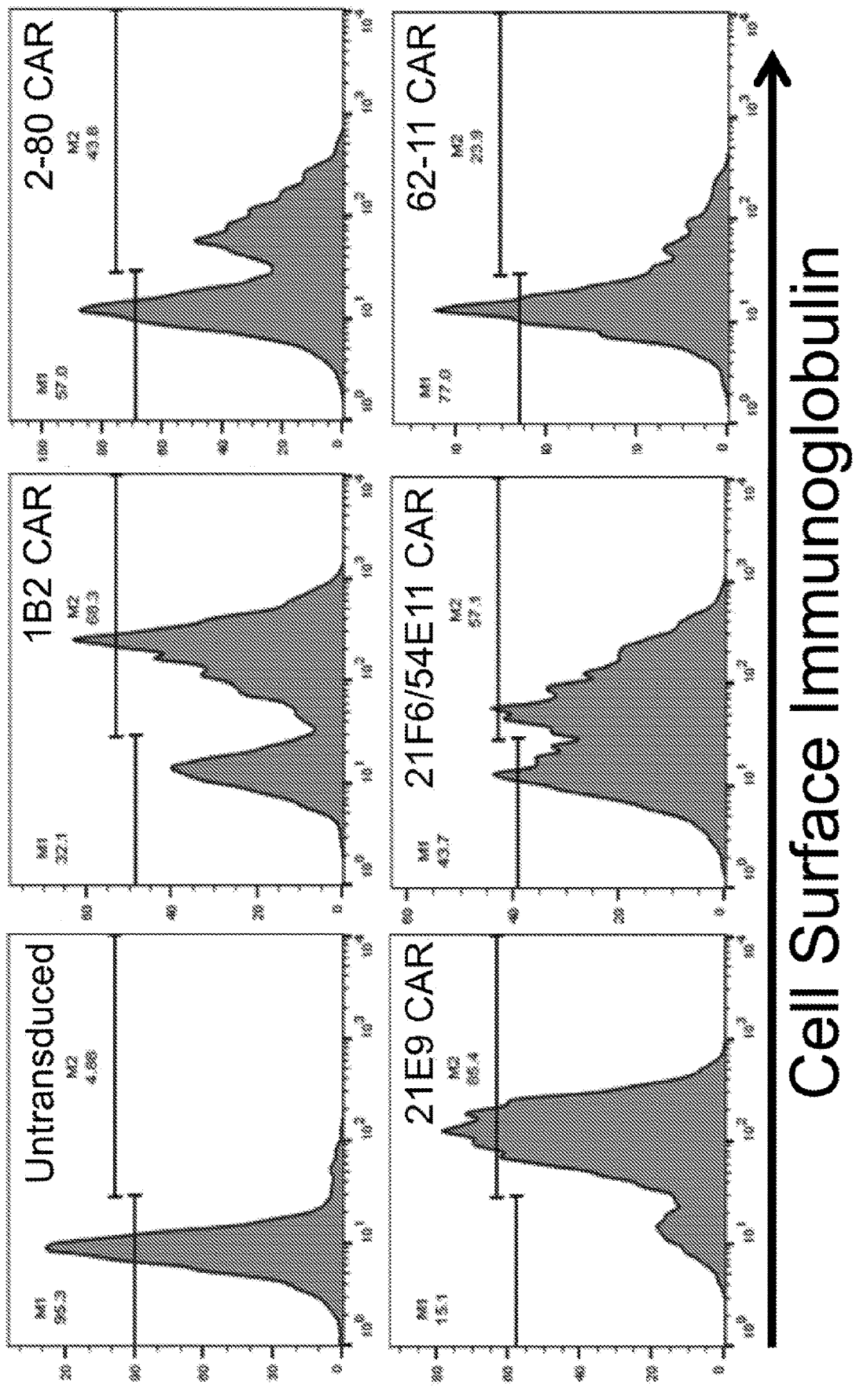

When vectors comprising the CAR constructs were transduced into purified primary C8TLs, expression of the CMV-specific CARs was detected by both Western blot via staining for the CD3ζ component (FIG. 4), and flow cytometry assessing for cell-surface expressed CMV-specific CARs by staining for the SCA sequence, since T cells do not normally have cell surface antibody expression (FIG. 5A & B). These results show that CMV-specific CARs were successfully expressed in primary C8TLs.

Figure 6:
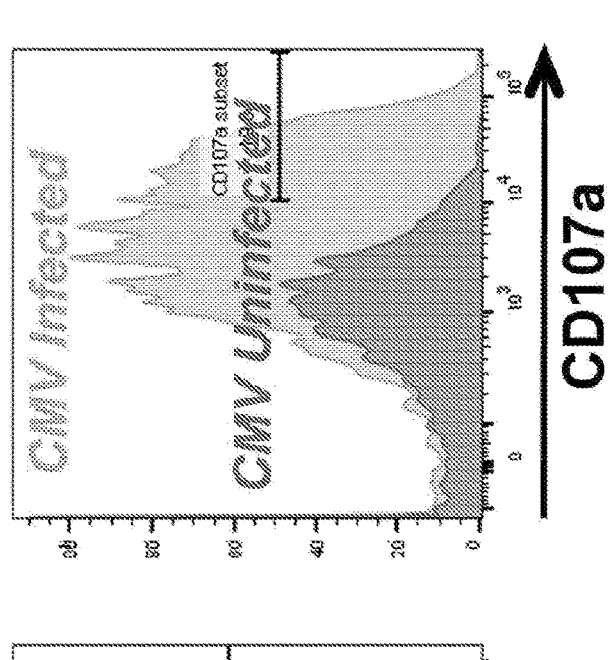
FIG. 6: Recognition of CMV-infected target cells by CAR-transduced C8TLs. 21E9 CAR-transduced primary C8TLs were exposed to CMV-infected or -uninfected target cells and assessed by intracellular IFN-γ/TNF-α and cell surface CD107a staining by flow cytometry.
Figure 6:
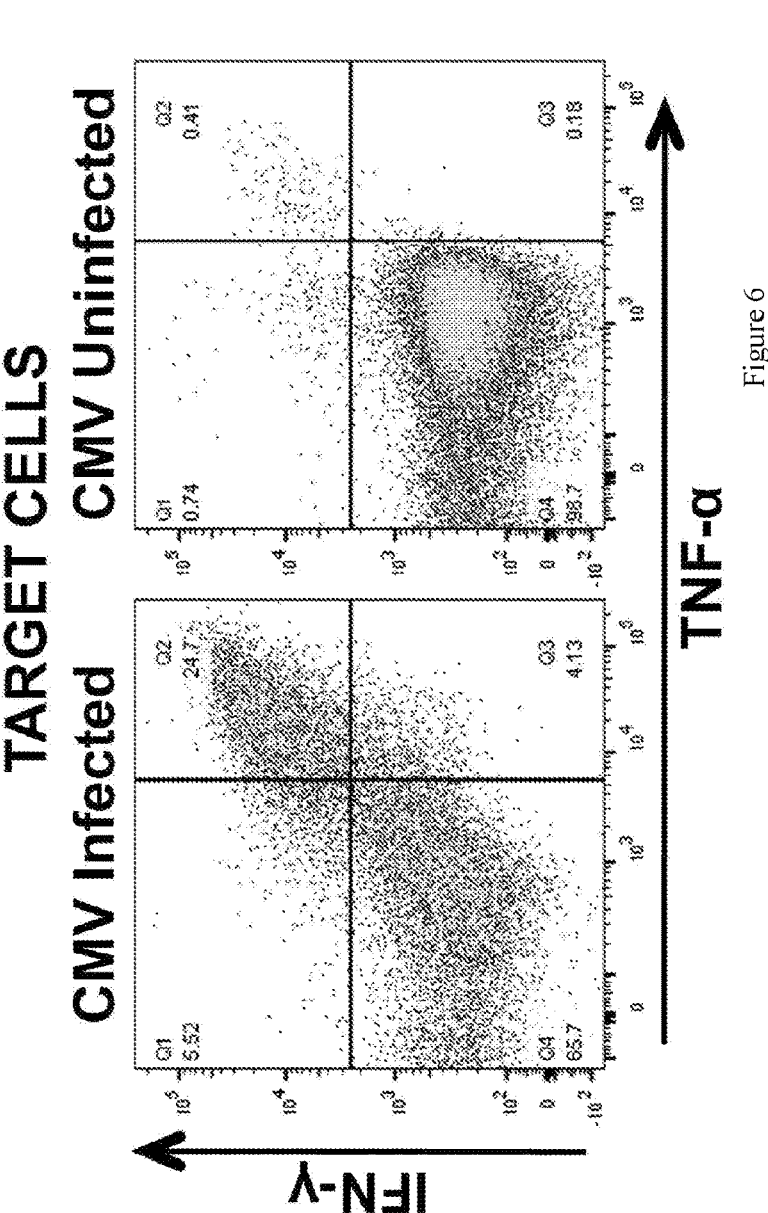
Figure 7:
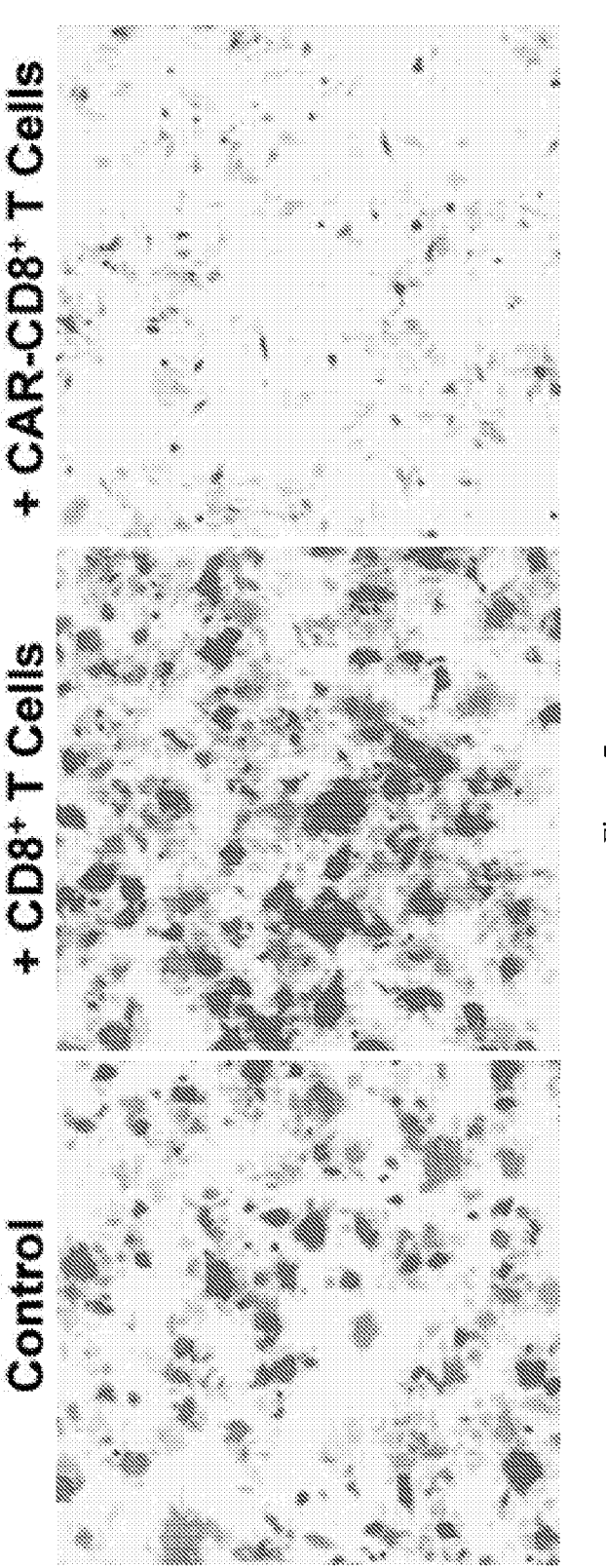
FIG. 7: Suppression/clearance of CMV by CAR-transduced primary C8TLs. Acutely CMV-infected cells (with a GFP-expressing strain of CMV) were cocultured with no cells, untransduced primary C8TLs, or C8TLs expressing the CAR were added after 4 days of infection. Imaging was done 3 days later. For better reproducibility in black and white, the color of the original figure was inverted.

Functional testing of enriched primary C8TLs transduced with CMV-specific CARs confirmed their ability to recognize CMV-infected cells and mediate antiviral activity. When C8TLs transduced with CMV-specific CARs were exposed to CMV-infected cells, the C8TLs released effector cytokines and expressed a marker of cytolytic activity in a CMV-specific manner (FIG. 6), thereby indicating that the CMV-specific CAR functionally directed their recognition of CMV-infected cells. When added to cells infected with a GFP-expressing strain of CMV, the transduced primary C8TLs markedly reduced the concentration of infected cells (FIG. 7), further confirming specific recognition and triggering of antiviral activity by the CMV-specific CARs.

Therefore, in some embodiments, the present invention is directed to a CAR construct encoding a CMV-specific CAR, which comprises a single chain antibody sequence or fragment thereof having SEQ ID NO: 21, SEQ ID NO: 22, SEQ ID NO: 23, SEQ ID NO: 24, SEQ ID NO: 25, and SEQ ID NO: 26 as follows:

Formula H1
(SEQ ID NO: 21)
G-X1-X2-X3-X4-X5-X6-X7-X8-X9 wherein, X1 is F or Y, X2 is S or T, X3 is L or F, X4 is S or T, X5 is D, I, N, S, or T, X6 is F, Y, or S, X7 is G, Y, or W, X8 is present or absent and if present, X8 is L or I, and X9 is present or absent and if present, X9 is G.

Formula H2
(SEQ ID NO: 22)
I-X10-X11-X12-X13-X14-X15-X16 wherein X10 is D, N, S, or W, X11 is D, N, P, T, or W, X12 is D, G, N, Y, or S, X13 is D, G, or T, X14 is D, G, N, or S, X15 is E, K, S, or Y, and X16 is present or absent and if present X16 is P or T.

Formula H3
(SEQ ID NO: 23)
X17-X18-X19-X20-X21-X22-X23-X24-X25-X26-X27-X28-
X29-X30-X31 wherein X17 is A, S, or V, X18 is R, N, or S, X19 is E, G, K, P, R, or S, X20 is G, H, K, L, Y, or W, X21 is D, L, R, S, or Y X22 is D, F, G, L, S, or Y X23 is A, D, F, G, L, P, or Y, X24 is A, D, I, Q, S, V, or Y, X25 is present or absent and if present, X25 is E, F, N, S, or Y, X26 is present or absent and if present, X26 is A, G, M, L, or P is, X27 present or absent and if present, X27 is D, L, or Y, X28 is present or absent and if present, X28 is A, F, L, or Y, X29 is present or absent and if present, X29 is D, F, G, or M, X30 is present or absent and if present, X30 is C, D, or Y, and X31 is present or absent and if present, X31 is S or Y.

Formula L1

(SEQ ID NO: 24)

X32-X33-X34-X35-X36-X37-X38-X39-X40-X41-X42 wherein X32 is E, K, or Q, X33 is G or S X34 is I, L, or V, X35 is D, G, S, or V, X36 is D, H, N, S, or T, X37 is D, N, S, or Y, X38 is present or absent and if present X38 is D, G, or N, X39 is present or absent and if present X39 is G, N, or Y, X40 is present or absent and if present X40 is K, N, or S, X41 is present or absent and if present X41 is F, Y, or T, and X42 is present or absent and if present X42 is Y.

Formula L2

(SEQ ID NO: 25)

X43-X44-S wherein X43 is D, L, R, T, or Y, and X44 is A, T, or V.

Formula L3

(SEQ ID NO: 26)

X45-X46-X47-X48-X49-X50-P-X51-T wherein X45 is S, Q, or W, X46 is H, N, or Q, X47 is D, G, S, or Y, X48 is H, N, R, S, T, or Y, X49 is E, H, K, R, S, or T, X50 is D, F, L, S, V, or W, and X51 is L, P, W, or Y.

In some embodiments, SEQ ID NO: 21 is GFSLSTYGIG (SEQ ID NO: 27), GFSLTTSGLG (SEQ ID NO: 28), GFTFSDYY (SEQ ID NO: 29), GYTFTIYG (SEQ ID NO: 30), GYTFTNFG (SEQ ID NO: 31), GYTFTSYG (SEQ ID NO: 32), GYTFTSYW (SEQ ID NO: 33), GYTFTIYW (SEQ ID NO: 34), or GYTFTSYW (SEQ ID NO: 35), preferably SEQ ID NO: 30.

In some embodiments, SEQ ID NO: 22 is IDPSDSET (SEQ ID NO: 36), IDPSDSET (SEQ ID NO: 37), IDPSD-SET (SEQ ID NO: 38), INTYTGEP (SEQ ID NO: 39), ISDDGNYT (SEQ ID NO: 40), ISNGGGST (SEQ ID NO: 41), IWWDDDK (SEQ ID NO: 42), or IWWNDNK (SEQ ID NO: 43), preferably SEQ ID NO: 39.

In some embodiments, SEQ ID NO: 23 is AREHYYGIN-PLLGC (SEQ ID NO: 44), ARGWLLPVFAY (SEQ ID NO: 45), ARKGYYGSSGYFDY (SEQ ID NO: 46), ARRGDG-LYSMDY (SEQ ID NO: 47), ARTGYFDV (SEQ ID NO: 48), SNGYSSFAY (SEQ ID NO: 49), VRPKRDFQY-LYAMDY (SEQ ID NO: 50), VRSLYDYDEGYYFDS (SEQ ID NO: 51), or ASSGTGAY (SEQ ID NO: 52), preferably SEQ ID NO: 46.

In some embodiments, SEQ ID NO: 24 is ESIDSYGNSF (SEQ ID NO: 53), KSVSTSGYSY (SEQ ID NO: 54), QGISNY (SEQ ID NO: 55), QSIGNN (SEQ ID NO: 56), QSISDY (SEQ ID NO: 57), QSLVHSNGNTY (SEQ ID NO: 58), QSVSND (SEQ ID NO: 59), QSISNN (SEQ ID NO: 60), or QSLLDSDGKTY (SEQ ID NO: 61), preferably SEQ ID NO: 59.

In some embodiments, SEQ ID NO: 25 is DTS (SEQ ID NO: 62), LAS (SEQ ID NO: 63), RAS (SEQ ID NO: 64), TVS (SEQ ID NO: 65), YAS (SEQ ID NO: 66), YTS (SEQ ID NO: 67), or LVS (SEQ ID NO: 68), preferably SEQ ID NO: 66.

In some embodiments, SEQ ID NO: 26 is QHSRELPWT (SEQ ID NO: 69), QNGHTFPPT (SEQ ID NO: 70), QQD-YSSPWT (SEQ ID NO: 71), QQSNEDPLT (SEQ ID NO: 72), QQSNRWPWT (SEQ ID NO: 73), QQYSKLPYT (SEQ ID NO: 74), SQSTHVPYT (SEQ ID NO: 75), QQSN-SWPLT (SEQ ID NO: 76), or WQGTHFPYT (SEQ ID NO: 77), preferably SEQ ID NO: 67.

In some embodiments, the VH sequence of the SCA comprises SEQ ID NOs: 30, 39, and 46.

In some embodiments, the VL sequence of the SCA comprises SEQ ID NOs: 59, 66, and 71.

In some embodiments, the SCA has a VH sequence comprising SEQ ID NOs: 30, 39, and 46, and a VL sequence comprising SEQ ID NOs: 59, 66, and 71.

In some embodiments, the VH sequence of the SCA is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, or SEQ ID NO: 19, preferably SEQ ID NO: 11.

In some embodiments, the VL sequence of the SCA is SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, or SEQ ID NO: 20, preferably SEQ ID NO: 12.

In some embodiments, the SCA has a VH sequence comprising SEQ ID NO: 11, and a VL sequence comprising SEQ ID NO: 12.

In some embodiments, the Leader Sequence has 90, 91, 92, 93, 94, 95, 96, 97, 99, or 100% sequence identity to MLLLVTSLLLCELPHPAFLLIP (SEQ ID NO: 78).

In some embodiments, the Flexible Linker has 90, 91, 92, 93, 94, 95, 96, 97, 99, or 100% sequence identity to SGGGGSGGGGSGGGGS (SEQ ID NO: 79).

In some embodiments, the IgG4 hinge-CH2-CH3 region spacer has 90, 91, 92, 93, 94, 95, 96, 97, 99, or 100% sequence identity to (SEQ ID NO: 80)

ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

In some embodiments, the CD8 transmembrane region has 90, 91, 92, 93, 94, 95, 96, 97, 99, or 100% sequence identity to DIYIWAPLAGTCGVLLLSL VITLYC (SEQ ID NO: 81).

In some embodiments, the 4-1BB co-signaling region has 90, 91, 92, 93, 94, 95, 96, 97, 99, or 100% sequence identity to (SEQ ID NO: 82)

KRGRKKLLYIFKQPFMRPVQTTQEEDGCSCRFPEEEEGGCEL.

In some embodiments, the CD3ζ signaling region has 90, 91, 92, 93, 94, 95, 96, 97, 99, or 100% sequence identity to (SEQ ID NO: 83)

RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

The sequences of the CMV-specific CARs exemplified herein are:

1B2 CAR:

(SEQ ID NO: 84)

MLLLVTSLLLCELPHPAFLLIPEVQLVESGGGVLVKPGGSLKLSCAASGFT

FSDYYMYWVRQTPEKRLEWVATISDDGNYTNYPDSVKGRFTISRDNAKNN

LYLQMSSLKSEDTAMYYCARGWLLPVFAYWGQGTLVTVSASGGGGSGGGG

SGGGGSDIVLTQSPATLSVTPGDSVSLSCRASQSIGNNLHWYQQKSHESP

RLLIKYTSQSISGIPSRFSGSGSGTDFTLNINSVETEDFGVYFCQQSNRW

PWTFGGGTKLEIKESKYGPPCPPCPAPEFLGGPSVFLFPPKPKDTLMISR

TPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLGKDIYIWAPL

AGTCGVLLLSLVITLYCKRGRKKLLYIFKQPFMRPVQTTQEEDGCSCRFP

EEEEGGCELRVKFSRSADAPAYKQGQNQLYNELNLGRREEYDVLDKRRGR

DPEMGGKPRRKNPQEGLYNELQKDKMAEAYSEIGMKGERRRGKGHDGLYQ

GLSTATKDTYDALHMQALPPR 2-80 CAR:

(SEQ ID NO: 85)

MLLLVTSLLLCELPHPAFLLIPQIQLVQSGPELKKPGETVKISCKASGYT

FTNFGMNWVKQAPGKGLKWMGWINTYTGEPTYADDFKGRFAFSLETSAST

ASLQINNLKNEDTATYFCARRGDGLYSMDYWGQGTSVTVSSSGGGGSGGGG

GSGGGGSDIVLTQSPASLAVSLGQRATISCRASESIDSYGNSFMYWYQQK

PGQPPKLLIYRASNLESGIPARFSGSGSRTDFTLTINPVEADDVATYYCQ

QSNEDPLTFGAGTKLELKESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKDIY

IWAPLAGTCGVLLLSLVITLYCKRGRKKLLYIFKQPFMRPVQTTQEEDGC

SCRFPEEEEGGCELRVKFSRSADAPAYKQGQNQLYNELNLGRREEYDVLD

KRRGRDPEMGGKPRRKNPQEGLYNELQKDKMAEAYSEIGMKGERRRGKGH

DGLYQGLSTATKDTYDALHMQALPPR

12E2 CAR:

(SEQ ID NO: 86)

MLLLVTSLLLCELPHPAFLLIPEVKLVESGGGLVQPGGSLKLSCATSGFT

FSDYYMFWVRQTPEKKLEWVAYISNGGGSTYYPDTVKGRFTISRDNDKNT

LYLQMSRLKSDDTALYYCVRPKRDFQYLYAMDYWGQGTSVTVSSSGGGGS

GGGGSGGGGSDIVLTQSPASLAVSLGQRATISCRASKSVSTSGYSYMHWY

QQKPGQSPKLLIYLASNLESGVPARFSGSGSGTDFTLNIHPVEDEDAATY

YCQHSRELPWTFGGGTKLEIKESKYGPPCPPCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

DIYIWAPLAGTCGVLLLSLVITLYCKRGRKKLLYIFKQPFMRPVQTTQEE

DGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRG

KGHDGLYQGLSTATKDTYDALHMQALPPR

13B5 CAR:

(SEQ ID NO: 87)

MLLLVTSLLLCELPHPAFLLIPQVTLKESGPGILKPSQTLSLTCSFSGFS

LTTSGLGVGWIRQPSGKGLEWLAHIWWDDDKYFNPSLRNQLTISKDTSRN

QVFLEITSVTTADTATYYCVRSLYDYDEGYYFDSWGQGTTLTVSSSGGGG

SGGGGSGGGGSEIVMIQSPATLSVNPGDRVSLSCRASQSISDYLHWYQQK

SHESPRLLIKYASQSISGIPSRFSGSGSGSDFTLSINSVEPEDVGVYYCO

NGHTFPPTFGGGTKLEIKESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKDIY

IWAPLAGTCGVLLLSLVITLYCKRGRKKLLYIFKQPFMRPVQTTQEEDGC

SCRFPEEEEGGCELRVKFSRSADAPAYKQGQNQLYNELNLGRREEYDVLD

KRRGRDPEMGGKPRRKNPQEGLYNELQKDKMAEAYSEIGMKGERRRGKGH

DGLYQGLSTATKDTYDALHMQALPPR

18F10 CAR:

(SEQ ID NO: 88)

MLLLVTSLLLCELPHPAFLLIPQVTLKESGPGILQPSQTLSLTCSFSGFS

LSTYGIGIGWIRQPSGKGLEWLAHIWWNDNKNYNTALKSRLTISKDPSNN

QVFLKIASVDTADTATYFCARTGYFDVWGAGTTVTVSSSGGGGSGGGGSG

GGGSDVVLTQTPLSLPVSLGDQVSISCSSSQSLVHSNGNTYIHWYLQKPG

QSPKLLIYTVSNRFSGVPDRFSGSGSGTDFTLKISRVEAEDLGLYFCSQS

THVPYTFGGGTKLEIKESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKDIYIW

APLAGTCGVLLLSLVITLYCKRGRKKLLYIFKQPFMRPVQTTQEEDGCSC

RFPEEEEGGCELRVKFSRSADAPAYKQGQNQLYNELNLGRREEYDVLDKR

RGRDPEMGGKPRRKNPQEGLYNELQKDKMAEAYSEIGMKGERRRGKGHDG

LYQGLSTATKDTYDALHMQALPPR

21E9 CAR:

(SEQ ID NO: 89)

MLLLVTSLLLCELPHPAFLLIPQIQLVQSGPELKKPGETVKISCKASGYT

FTIYGMNWVKQAPGKGLKWMGWINTYTGEPTYADDFRGRFAFSLETSAST

AYLQINNLKNEDTATYFCARKGYYGSSGYFDYWGQGTTLTVSSSGGGGSG

-continued

```
GGGSGGGGSSIVMTQTPKFLLVSAGDRVTITCKASQSVSNDVSWYQQKPG

QSPKLLIYYASNRYTGVPDRFTGSGYGTDFTFTISTVQAEDLAVYFCQQD

YSSPWTFGGGTKLEIKESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKDIYIW

APLAGTCGVLLLSLVITLYCKRGRKKLLYIFKQPFMRPVQTTQEEDGCSC

RFPEEEEGGCELRVKFSRSADAPAYKQGQNQLYNELNLGRREEYDVLDKR

RGRDPEMGGKPRRKNPQEGLYNELQKDKMAEAYSEIGMKGERRRGKGHDG

LYQGLSTATKDTYDALHMQALPPR
```

21F6_54E11 (21F6) CAR:

(SEQ ID NO: 90)
```
MLLLVTSLLLCELPHPAFLLIPQIQLVQSGPELKKPGETVKISCKASGYT

FTSYGMNWVKQAPGKGLKWMGWINTYTGEPTYADDFKGRFAFSLETSAST

AYLQINNLKNEDTATYFCAREHYYGINPLLGCWGQGTTLTVSSSGGGGSG

GGGSGGGGSDIQMTQTTSSLSASLGDRVTISCSASQGISNYLNWYQQKPD

GTVKLLIYDTSSLHSGVPSRFSGSGSGTDYSLTISNLEPEDIATYYCQQY

SKLPYTFGGGTKLEIKESKYGPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGKDIYIW

APLAGTCGVLLLSLVITLYCKRGRKKLLYIFKQPFMRPVQTTQEEDGCSC

RFPEEEEGGCELRVKFSRSADAPAYKQGQNQLYNELNLGRREEYDVLDKR

RGRDPEMGGKPRRKNPQEGLYNELQKDKMAEAYSEIGMKGERRRGKGHDG

LYQGLSTATKDTYDALHMQALPPR
```

62-11 CAR:

(SEQ ID NO: 91)
```
MLLLVTSLLLCELPHPAFLLIPQVQLQQPGAELVRPGASVKLSCKASGYT

FTSYWMNWVKQRPGQGLEWIGMIDPSDSETHYNQMFKDKATLTVDKSSST

AYMQLSSLTSEDSAVYYCSNGYSSFAYWGQGTLVTVSSSGGGGSGGGGSG

GGGSDIQMTQTTSSLSASLGDRVTISCSASQGISNYLNWYQQKPDGTVKL

LIYDTSSLHSGVPSRFSGSGSGTDYSLTISNLEPEDIATYYCQQYSKLPY

TFGGGTKLEIKESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGKDIYIWAPLAG

TCGVLLLSLVITLYCKRGRKKLLYIFKQPFMRPVQTTQEEDGCSCRFPEE

EEGGCELRVKFSRSADAPAYKQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPR
```

Therefore, in some embodiments, the CMV-specific CAR comprises SEQ ID NO: 84, SEQ ID NO: 85, SEQ ID NO: 86, SEQ ID NO: 87, SEQ ID NO: 88, SEQ ID NO: 89, SEQ ID NO: 90, or SEQ ID NO: 91, preferably the CMV-specific CAR comprises SEQ ID NO: 89.

In some embodiments, C8TLs transduced with CMV-specific CARs may be administered to subjects. In some embodiments, stem cells, such as hematopoietic stem and progenitor cells (HSPCs), may be transduced with CAR constructs encoding CMV-specific CARs and engrafted in subjects to be treated. As used herein, "HSPC-based CAR cells" refer to a cell engineered to express a CAR by transducing a HSPC with a CAR construct and progeny thereof. As used herein, "HSPC" refers to a hematopoietic stem cell (HSC) and/or a hematopoietic progenitor cell (HPC).

As used herein, a given percentage of "sequence identity" refers to the percentage of nucleotides or amino acid residues that are the same between sequences, when compared and optimally aligned for maximum correspondence over a given comparison window, as measured by visual inspection or by a sequence comparison algorithm in the art, such as the BLAST algorithm, which is described in Altschul et al., (1990) J Mol Biol 215:403-410. Software for performing BLAST (e.g., BLASTP and BLASTN) analyses is publicly available through the National Center for Biotechnology Information (ncbi.nlm.nih.gov). The comparison window can exist over a given portion, e.g., a functional domain, or an arbitrarily selection a given number of contiguous nucleotides or amino acid residues of one or both sequences. Alternatively, the comparison window can exist over the full length of the sequences being compared. For purposes herein, where a given comparison window (e.g., over 80% of the given sequence) is not provided, the recited sequence identity is over 100% of the given sequence. Additionally, for the percentages of sequence identity of the proteins provided herein, the percentages are determined using BLASTP 2.8.0+, scoring matrix BLOSUM62, and the default parameters available at blast.ncbi.nlm.nih.gov/ Blast.cgi. See also Altschul, et al., (1997) Nucleic Acids Res 25:3389-3402; and Altschul, et al., (2005) FEBS J 272: 5101-5109.

Optimal alignment of sequences for comparison can be conducted, e.g., by the local homology algorithm of Smith & Waterman, Adv Appl Math 2:482 (1981), by the homology alignment algorithm of Needleman & Wunsch, J Mol Biol 48:443 (1970), by the search for similarity method of Pearson & Lipman, PNAS USA 85:2444 (1988), by computerized implementations of these algorithms (GAP, BEST-FIT, FASTA, and TFASTA in the Wisconsin Genetics Software Package, Genetics Computer Group, 575 Science Dr., Madison, WI), or by visual inspection.

As used herein, the terms "protein", "polypeptide" and "peptide" are used interchangeably to refer to two or more amino acids linked together. Groups or strings of amino acid abbreviations are used to represent peptides. Except when specifically indicated, peptides are indicated with the N-terminus on the left and the sequence is written from the N-terminus to the C-terminus.

As used herein, "antibody" refers to naturally occurring and synthetic immunoglobulin molecules and immunologically active portions thereof (i.e., molecules that contain an antigen binding site that specifically bind the molecule to which antibody is directed against). As such, the term antibody encompasses not only whole antibody molecules, but also antibody multimers and antibody fragments as well as variants (including derivatives) of antibodies, antibody multimers and antibody fragments. Examples of molecules which are described by the term "antibody" herein include: single chain Fvs (scFvs), Fab fragments, Fab' fragments, F(ab')$_2$, disulfide linked Fvs (sdFvs), Fvs, and fragments comprising or alternatively consisting of, either a VL or a VH domain.

In some embodiments, the antibodies are monoclonal antibodies. In some embodiments, the monoclonal antibodies are obtained from rabbit-based hybridomas. As used herein, a compound (e.g., receptor or antibody) "specifically binds" a given target (e.g., ligand) if it reacts or associates more frequently, more rapidly, with greater duration, and/or with greater binding affinity with the given target than it does with a given alternative, and/or indiscriminate binding that gives rise to non-specific binding and/or background binding. As used herein, "non-specific binding" and "background binding" refer to an interaction that is not dependent on the presence of a specific structure.

As used herein, "binding affinity" refers to the propensity of a compound to associate with (or alternatively dissociate from) a given target and may be expressed in terms of its dissociation constant, Kd. In some embodiments, the antibodies have a Kd of $10^{-5}$ or less, $10^{-6}$ or less, preferably $10^{-7}$ or less, more preferably $10^{-8}$ or less, even more preferably $10^{-9}$ or less, and most preferably $10^{-10}$ or less, to their given target. Binding affinity can be determined using methods in the art, such as equilibrium dialysis, equilibrium binding, gel filtration, immunoassays, surface plasmon resonance, and spectroscopy using experimental conditions that exemplify the conditions under which the compound and the given target may come into contact and/or interact. Dissociation constants may be used determine the binding affinity of a compound for a given target relative to a specified alternative. Alternatively, methods in the art, e.g., immunoassays, in vivo or in vitro assays for functional activity, etc., may be used to determine the binding affinity of the compound for the given target relative to the specified alternative. Thus, in some embodiments, the binding affinity of the antibody for the given target is at least 1-fold or more, preferably at least 5-fold or more, more preferably at least 10-fold or more, and most preferably at least 100-fold or more than its binding affinity for the specified alternative.

The following examples are intended to illustrate but not to limit the invention.

EXAMPLES

Eight novel CMV-specific CARs were constructed using anti-CMV neutralizing antibody sequences that target the pentameric complex (PC) The CMV-specific CARs were transduced via lentiviral vector into primary C8TLs. Activity against CMV-infected target cells was assessed by release of cytokines (interferon-γ and tumor necrosis factor-α, upregulation of surface CD107a, proliferation, cytolysis of infected cells, and suppression of viral replication. While some CARs showed varying functional activity across these assays, one CMV-specific CAR based on antibody 21E9 was consistently superior in all measures. These results support development of a CMV-specific CAR for therapeutic use against CMV and potentially other applications harnessing CMV-driven immunotherapies.

Materials and Methods

Anti-CMV Antibody Sequences
The full variable region sequences of neutralizing antibodies against CMV were utilized to create single chain antibody genes synthesized as codon optimized genes coding for the heavy chain and light chain variable regions (Table 1) separated by a linker, additionally with an upstream leader sequence from granulocyte-macrophage colony-stimulating factor.

Cell Lines
The cell lines 293T and ARPE-19 were maintained Dulbecco's modified essential medium supplemented with L-glutamine (2 mM), penicillin (100 U/mL), streptomycin (100 U/mL), and heat-inactivated fetal bovine serum (10%) using methods in the art. Primary C8TLs from healthy donors were generated from whole peripheral blood mononuclear cells (PBMCs); in brief they were purified with the MACS Column Separation Kit by positive selection according to the manufacturer's protocol (Miltenyi, San Diego, CA) and stimulated for five days with an anti-CD3 antibody in the presence of irradiated feeder PBMC and 50 U/mL recombinant human interleukin-2 (NIH AIDS Reagent Repository), yielding >95% pure CD3$^+$/CD8$^+$ cells. Experiments were repeated using PBMCs from three healthy donors provided by the UCLA AIDS Institute Virology Core Facility as institutional review board exempt materials without any demographic information.

Chimeric Antigen Receptor Gene and Lentiviral Vector Construction
The lentiviral vector pCCLcMNDU3c-X2, gift of D. B. Kohn, was first modified to contain the sequence for the fixed regions (except the leader and single chain antibody sequences) of a previously reported human CAR, consisting of an IgG$_4$-based spacer (additionally containing a silent mutation creating a unique Apa I restriction site), CD8 transmembrane domain, co-signaling domain from 4-1BB (CD137), and signaling domain from the human CD3 complex ζ chain (CD247). Additionally, sequences for the P2A ribosomal skip sequence with a furin cleavage site followed by the heat stable antigen murine CD24 reporter (HSA) were inserted immediately downstream of the CAR sequences. This modified vector was digested with Hpa I and Apa I restriction enzymes, and PCR amplified products of the leader-single chain antibody sequences were inserted using the In-Fusion Cloning Kit (Takara, Mountain View, CA), followed by sequence confirmation of the final vectors. Lentiviral stocks were produced by co-transfection of HEK-293T cells with these constructs with Vesicular Stomatitis Virus envelope glycoprotein G protein and HIV-based packaging vectors, and stored in aliquots at −80° C. until use.

CAR Transduction of Primary C8TLs
Cells were transduced with the CAR delivery lentiviral vectors . Briefly,
polystyrene 24-well tissue culture plates were pre-coated with RetroNectin (Takara Bio, Mountain View, CA). Lentiviral vector at a concentration of ~50 ng p24 antigen in 100 μL volume was added and centrifuged at 2000 g for 2 hours. $10^6$ cells were then added for transduction, and maintained in RPMI 1640 supplemented with L-glutamine (2 mM), penicillin (100 U/mL), streptomycin (100 U/mL), heat-inactivated fetal bovine serum (10%), HEPES buffer (10 mM), and 50 U/mL recombinant human interleukin-2 (R10-50). These cells were maintained and enriched with periodic restimulations using a goat anti-human F(ab)2 antibody (catalog #109-006-006, Jackson ImmunoResearch Laboratories), to at least 70% purity before use in functional testing experiments.

Western Blot for CAR Expression
Transduced C8TLs were assessed for CAR expression by Western blot. Briefly, two million transduced cells were lysed and subjected to protein electrophoresis, followed by transfer onto a 0.45 μm polyvinylidene difluoride (PVDF) membrane (Millipore, Billerica, MA). The membrane was probed by using a mouse anti-human CD247 monoclonal antibody (#551033; BD Pharmingen, San Jose, CA) and the SuperSignal West Pico detection kit (Pierce, Rockford, IL), which yielded bands for both endogenous CD247 as well as higher molecular weight CD247-containing CAR proteins.

Flow Cytometric Analysis for Cell Surface CAR Expression

Detection of cell surface CAR expression on transduced cells was performed using methods in the art. In brief, cells were stained with fluorescein isothiocyanate (FITC)-conjugated goat anti-human F(ab)2 antibody (catalog #109-006-003, Jackson ImmunoResearch Laboratories, West Grove, PA) or isotype control antibody, fixed, and analyzed by flow cytometry (MACSQuantVYB, Miltenyi, Sunnyvale, CA) for analysis of cell surface CAR expression (FlowJo, Ashland, OR).

CMV Strains and Production of Viral Stocks

GFP-labeled TB40/E and TR strains of human cytomegalovirus (CMV) that express a GFP reporter under the SV40 promoter were derived from BAC DNA, gift of T. E. Shenk and E. A. Murphy. CMV stocks were generated following viral propagation in ARPE-19 cells (American Type Tissue Culture Collection) by ultracentrifugation procedures in the art and titrated on ARPE-19 cells by immunostaining using the IE1-specific monoclonal antibody p63-27, gift of William Britt, and the Vectastain ABC kit (Vector Laboratories) according to the manufacturer's instructions.

Flow Cytometric Analysis of Intracellular Cytokines and Cell Surface CD107a Expression by CAR-Transduced Primary C8TLs ARPE-19 cells were seeded in 24-well plates at $2\times10^5$ cells/well, and 24 hours later were infected with CMV using multiplicity of infection (MOI) of 3, with mock-infected cells as a negative control. Five days later, when the cells were uniformly infected as reflected by GFP expression, $10^6$ CAR-transduced primary C8TLs were added and incubated for an additional hour; stimulation with leukocyte activation cocktail (BD Biosciences, San Jose, CA) served as a positive control for activation. Brefeldin A and monensin (0.5 μl Golgi Plug and 0.5 μl Golgi Stop, BD Biosciences, San Jose, CA) and allophycocyanin (APC)-conjugated anti-CD107a antibody (catalog #328620, Biolegend, San Diego, CA) antibody were then added. After 5 hours of co-incubation, the CAR-transduced C8TLs were removed from each well for analysis. Surface staining was then performed with anti-human antibodies including anti-IgG F(ab)2 conjugated with fluorescein isothiocyanate (FITC) (catalog ##109-096-003, Jackson ImmunoResearch Laboratories), anti-CD8 conjugated with phycoerythrin (PE) (catalog #300908, Biolegend, San Diego, CA), followed by fixation and permeabilization (Cytofix/Cytoperm, BD Biosciences, San Jose, CA), followed by intracellular cytokine staining with anti-human antibodies including anti-interferon-γ conjugated with Alexa Fluor-647 (catalog #506507, Biolegend, San Diego, CA) and anti-tumor necrosis factor-α conjugated with Alexa Fluor-700 (catalog #502928, Biolegend, San Diego, CA). Cells were analyzed by FACSCelesta (BD Biosciences, San Jose, CA) using FlowJo software (BD Biosciences, San Jose, CA).

Flow Cytometric Analysis of Cell Proliferation

ARPE-19 cells were used as stimulating cells to test for CMV-mediated proliferation of CAR-transduced C8TLs, using methods in the art with the following modifications. In a 48-well plate, $10^5$ ARPE-19 cells were seeded one day before infection with HCMV TB40/E or TR at a MOI of 1.5 and cultured for 3 days to obtain >90% infection as seen by GFP fluorescence (or mock-infected as negative controls). CAR-transduced C8TLs were labeled with CellTrace Violet according to the manufacturer's directions (Thermo Fisher Scientific, Grand Island, NY), and $5\times10^5$ CAR-transduced cells with $3\times10^6$ irradiated feeder PBMC were added to each well and cultured in R10-50 for seven days with a medium exchange at three days. Anti-CD3 antibody stimulation served as a positive control. For analysis, $5\times10^6$ cells were harvested from each well and co-stained for CD8 and human F(ab), fixed with 1% paraformaldehyde, and analyzed by flow cytometry gated on the CD8$^+$ population (MACSQuant VYB, Miltenyi Biotech, Sunnyvale, CA and FlowJo software, BD Biosciences, San Jose, CA).

Chromium Release Assay of Cytolytic Activity Against CMV-Infected Cells by CAR-Transduced Primary C8TLs Killing of CMV-infected target cells by CAR-transduced primary C8TLs was tested in $^{51}$Cr release assays using methods in the art, with the following modifications. ARPE-19 cells were plated at $10^6$ per T25 tissue culture flask and infected the next day with CMV TB40/E or TR at a multiplicity of infection of 1.5 (or mock-infected as a negative control), then cultured for four days to achieve >90% infection by GFP expression. The cells were detached by incubation in 5 mM EDTA in phosphate buffered saline for 15 minutes at 37° C., then labeled with $^{51}$Cr for use in chromium release assays.

Assessment of Suppression of CMV Replication by CAR-Transduced Primary C8TLs.

Suppression of CMV replication was assessed. ARPE-19 cells were seeded into 96-well plates at $2\times10^4$ cells/well, and infected following day with CMV TB40/E or TR with an MOI of 1. After four days, $2\times10^5$ CAR-transduced (or control mock-transduced) primary C8TLs were added to each well and imaged after 8 hours of co-incubation using an Axio Observer Z1 inverted fluorescence microscope equipped with a linear motorized stage (Carl Zeiss, Pleasanton, CA).

RESULTS

Figure 2:
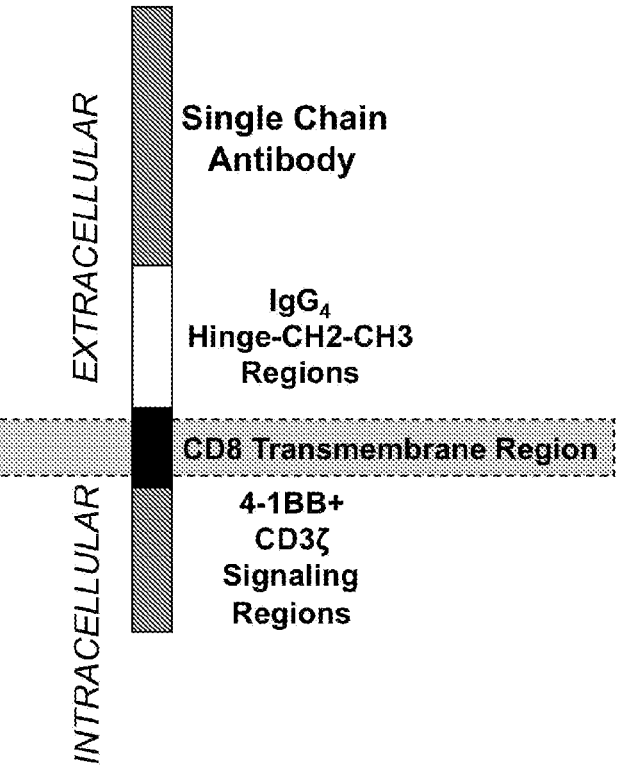
FIG. 2: Schematic of a typical CAR. A single chain antibody serves as the binding domain (gray, top portion), tethered by an immunoglobulin hinge-CH2-CH3 region spacer (white) to the CD8 transmembrane region (black), linked to a 4-1BB and CD3ζ co-signaling and signaling domains (gray, bottom portion).

Genetic Construction of Chimeric Antigen Receptors Based on Neutralizing Antibodies Against CMV The sequences of previously identified neutralizing monoclonal antibodies targeting different CMV PC proteins were utilized as targeting regions for chimeric antigen receptor design (Table 1). These included antibodies targeting epitopes in the gH subunit (21E9, 2-80, 18F10, 62-11), conformational epitopes in the UL128/130/131A subunits (1B2, 12E2, 21F6), and a linear epitope in UL128 (13B5), all of which had previously been confirmed to bind CMV-infected cells (not shown). Genes for single chain versions of these antibodies were incorporated into the backbone that we previously described for HIV-1-specific CARs, consisting of the single chain antibody targeting region, a spacer based on the IgG$_4$ constant region, the CD8 transmembrane domain, and cytoplasmic signaling domains from 4-1BB and CD3ζ (FIG. 2). These novel CAR genes were inserted into a lentiviral vector for transduction of primary C8TLs.

The Anti-CMV Antibody-Based CARs are Expressed by Transduced Primary C8TLs

Figure 5B:
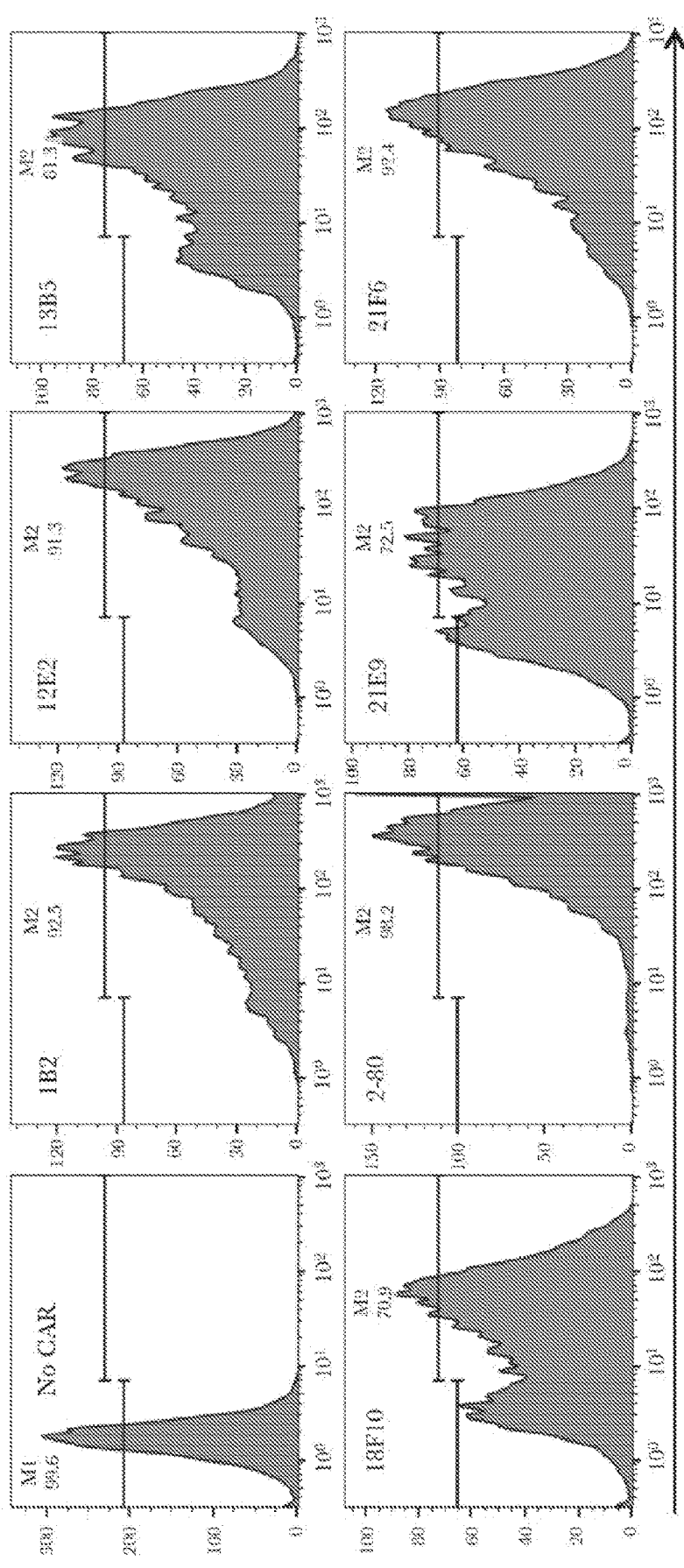
FIG. 5B: CAR expression in transduced primary C8TLs by flow cytometry. Primary C8TLs were transduced with lentiviral vectors delivering genes for the indicated CARs. The cells were then stained for cell surface human antibody expression and analyzed by flow cytometry. Not shown: 62-11.

Primary CD8$^+$ cells from healthy donors were transduced and tested for expression of the novel CARs. Western blot analysis for expression of CD3ζ demonstrated detection of CAR expression as a larger CD3ζ-expressing protein in addition to the native CD3ζ protein (FIG. 4). Cell surface expression of the CARs was further confirmed by staining for the immunoglobulin domain (not present on native T cells) on the surface of the transduced cells and detection by flow cytometry (FIG. 5B). Both modes of detection revealed that all eight novel CARs were expressed by primary C8TLs.

CAR-Transduced Primary C8TLs are Specifically Triggered to Release Cytokines and Upregulate Cell Surface CD107a by CMV-Infected Target Cells

Figure 8:
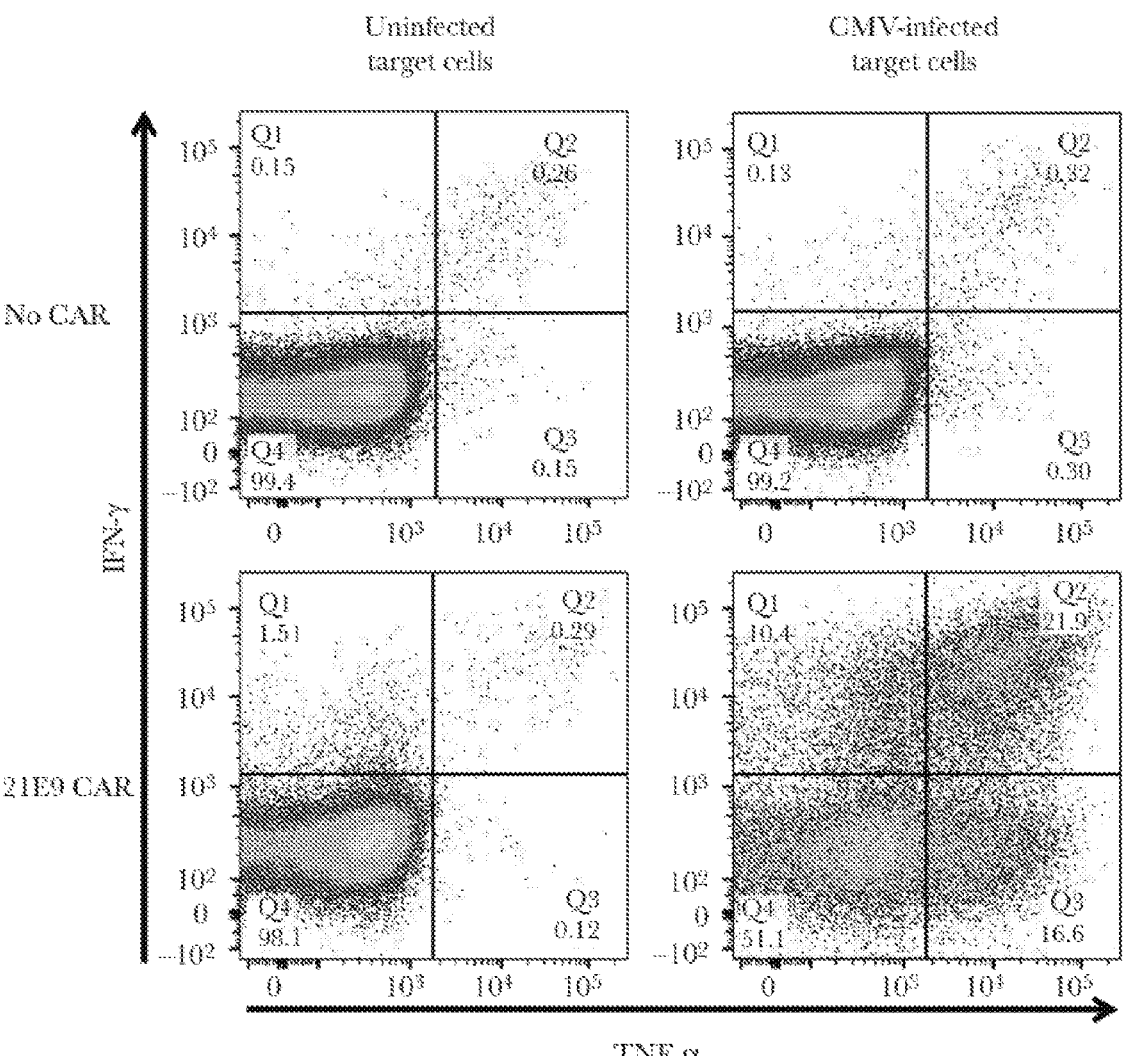
FIG. 8 to FIG. 11: Intracellular cytokine and cell surface CD107a expression by CAR-transduced primary C8TLs upon exposure to CMV-infected cells.
Figure 9:
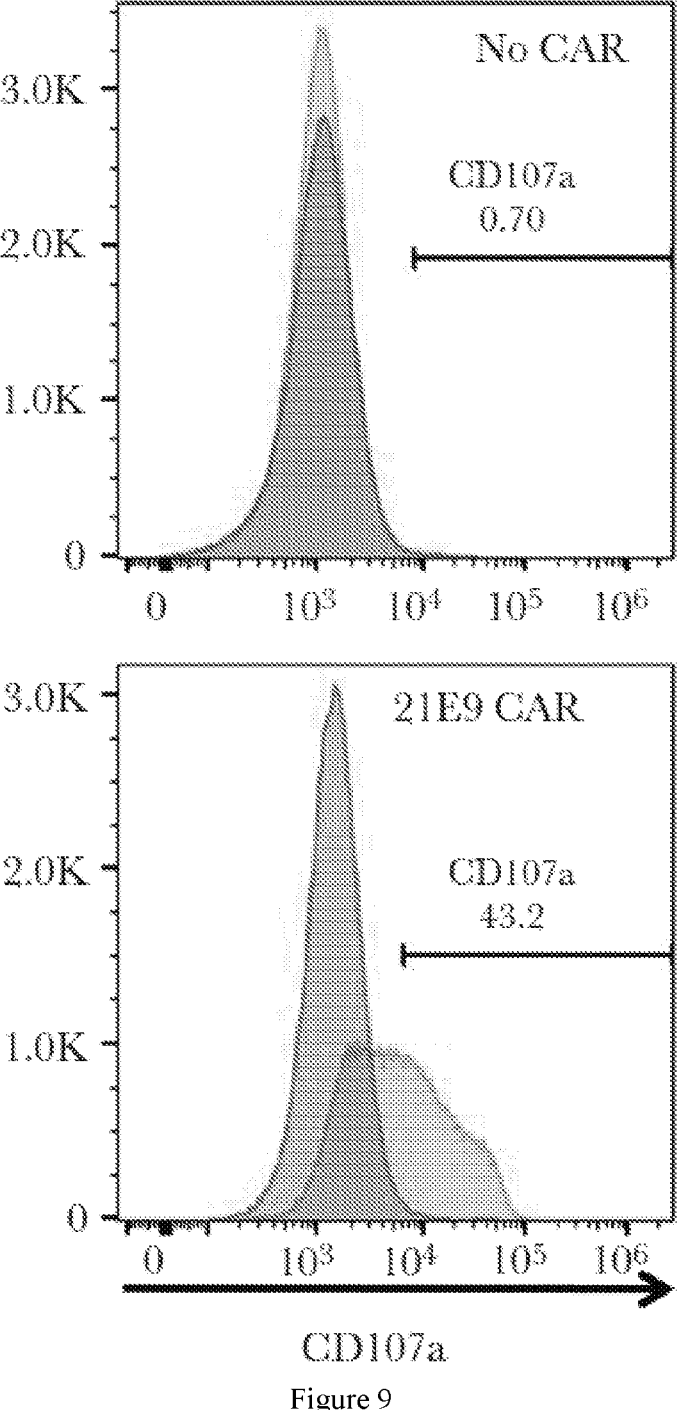
Figure 10:
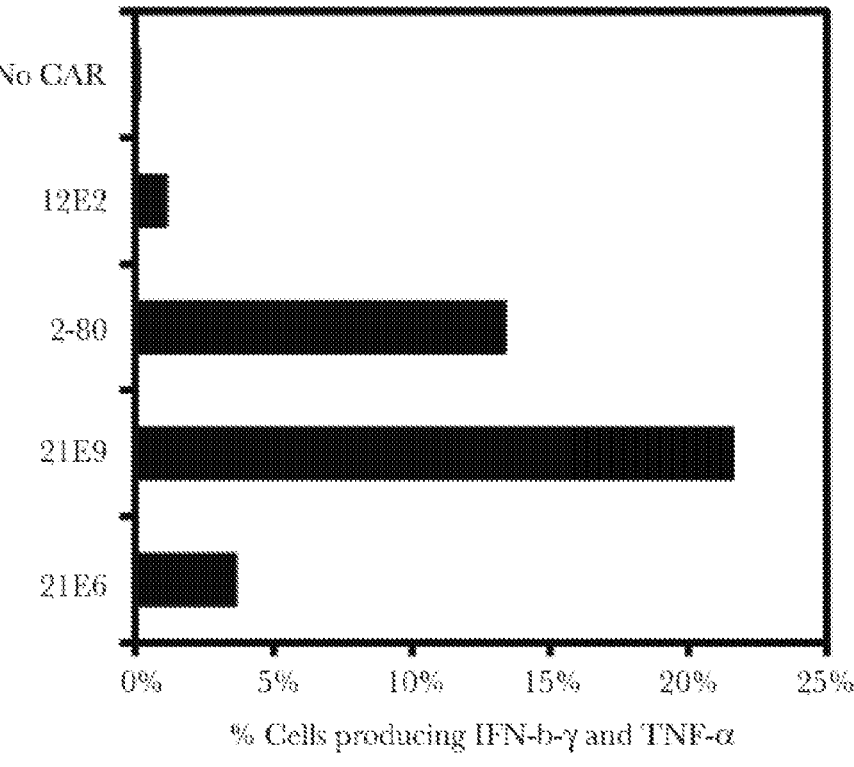
Figure 11:
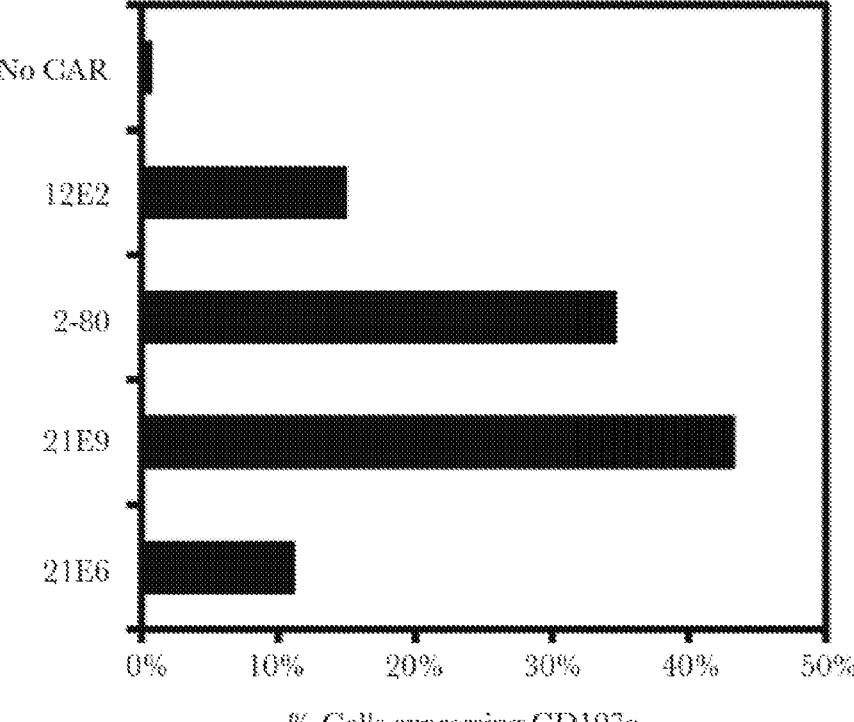

To test whether the CARs recognize their target proteins on the surface of CMV-infected cells, CAR-transduced primary C8TLs were exposed to acutely CMV TR-infected ARPE-19 cells and assessed for specific production of IFN-γ and TNF-α. Non-transduced C8TLs demonstrated minimal cytokine production in response to the ARPE-19 cells regardless of CMV infection. In contrast, at least two CARS, 21E9 and 2-80 (both targeting gH) showed specific cytokine release in response to CMV-infected but not CMV-uninfected cells (FIG. 8 and FIG. 10). Simultaneous evaluation for cell surface expression of the degranulation marker CD107a correlated to cytokine release (FIG. 9 and FIG. 11), again demonstrating that CARs 21E9 and 2-80, and to a lesser extent 12E2 and 21F6 (targeting the UL128/130/131A subunit), mediated CMV-specific cell triggering. Further studies focused on these four CARs. Similar results were seen with target ARPE-19 cells infected with CMV TB40/E infected cells (not shown).

CAR-Transduced Primary C8TLs Proliferate in Response to CMV-Infected Target Cells

Figure 12:
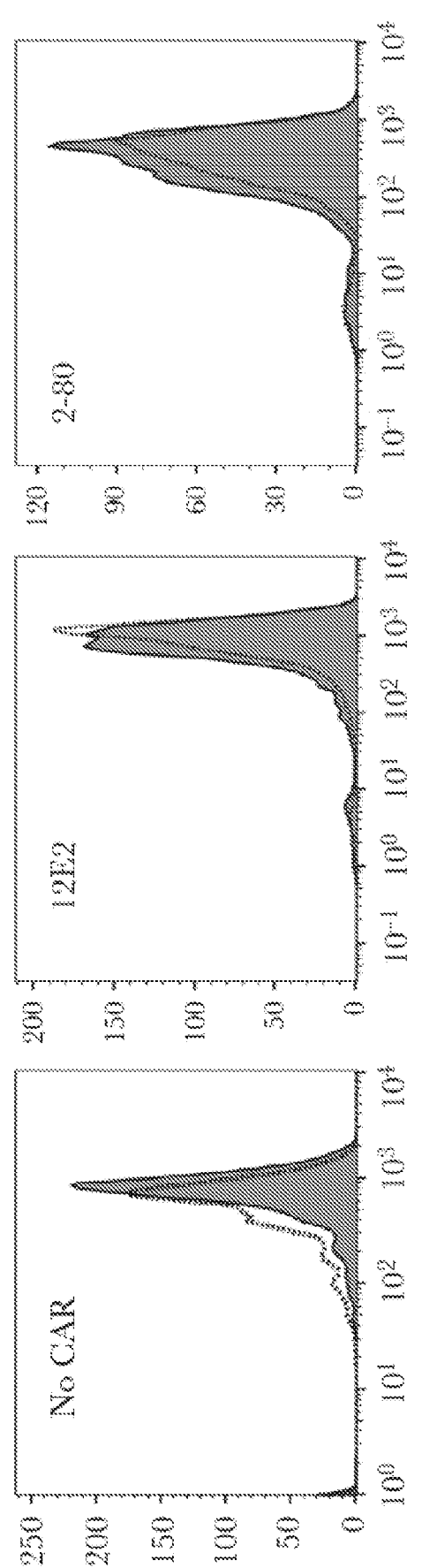
FIG. 12: Proliferation of CAR-transduced primary C8TLs upon exposure to CMV-infected cells. Primary C8TLs transduced with the indicated CAR were labeled with CellTrace Violet dye and co-cultured for 6 days with uninfected (open gray histograms) or CMV TB40/E-infected (filled black histograms) ARPE-19 cells and analyzed by flow cytometry for dye expression after seven days. These results are representative of two independent experiments with two different C8TL donors, each performed in biological duplicates.
Figure 12:
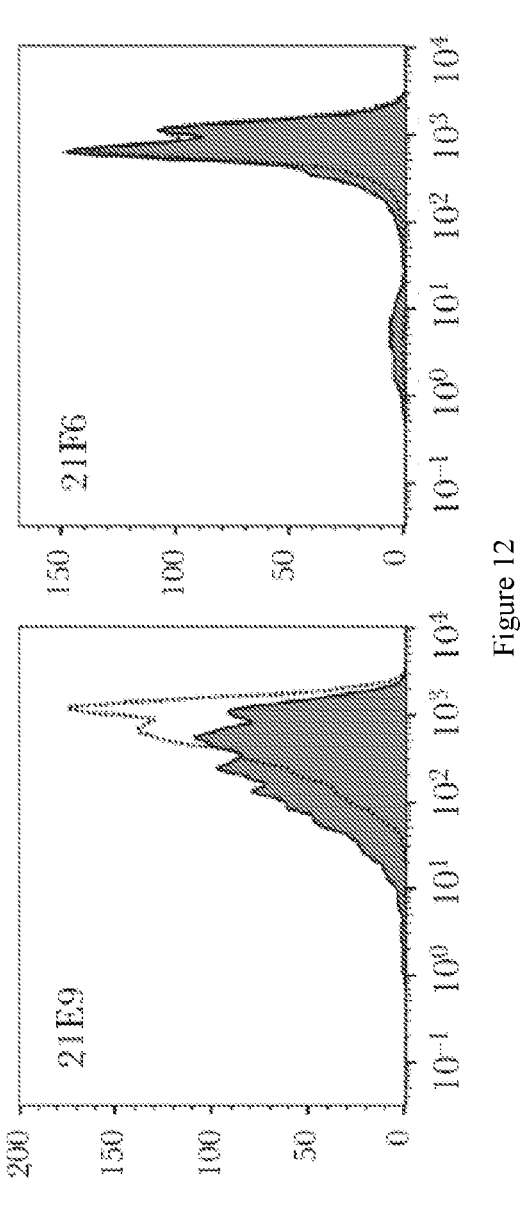

Further evaluating the function of CAR-transduced primary C8TLs, the proliferation of these cells in response to CMV-infected cells was tested (FIG. 12). The 21E9 CAR mediated modest proliferation when exposed to CMV-infected, but did not exhibit proliferation in response to uninfected cells. The other three CARs (2-80, 12E2, 21F6) mediated no appreciable proliferation. Thus at least one CAR conferred CMV-specific proliferation of transduced C8TLs.

CAR-Transduced primary C8TLs Mediate Modest Cytolysis of CMV-Infected Target Cells

Figure 13:
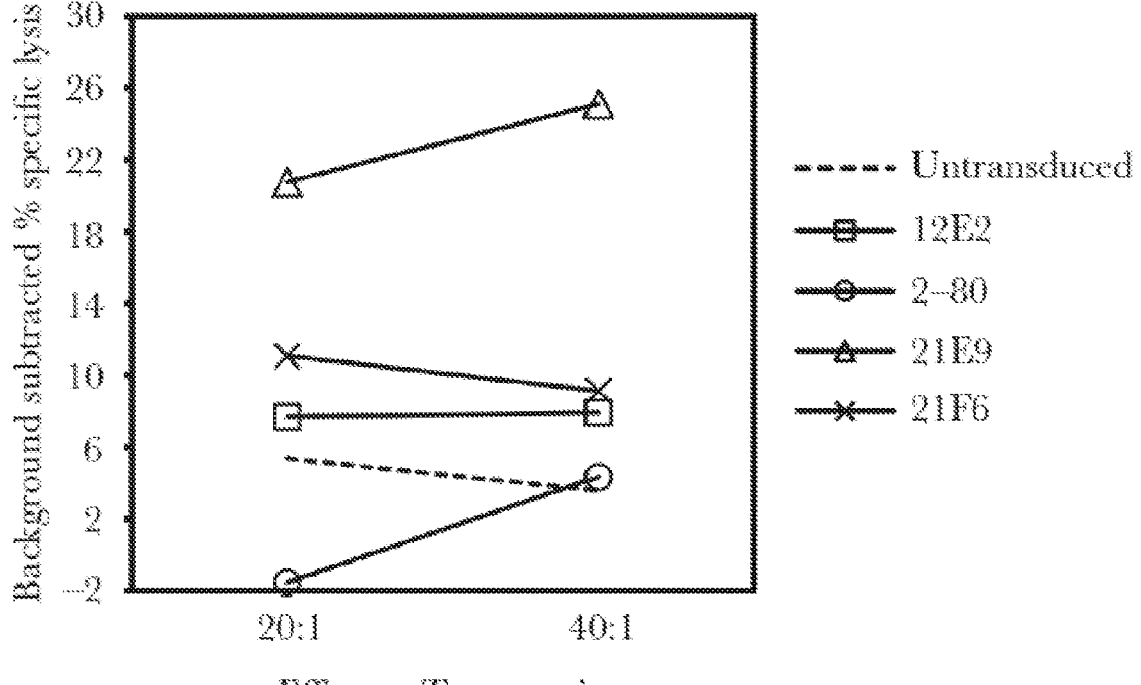
FIG. 13: Killing of CMV-infected target cells by CAR-transduced primary C8TLs. Background specific lysis of uninfected cells (<6%, except for 2-80 that had background levels of 20% and 32% at effector to target ratios of 20:1 and 40:1 respectively) was subtracted from specific lysis of CMV TB40/E-infected cells. In three independent experiments with three different C8TL donors, only 21E9 exhibited consistent targeted killing of CMV-infected cells.

CMV-infected cells are intrinsically resistant to C8TL cytolysis. The capacity of CAR-redirected primary C8TLs to mediate CMV-specific cytolysis was tested by $^{51}$chromium release assays (FIG. 13). The only CAR that mediated consistent specific killing of CMV-infected target cells in multiple experiments was 21E9, which mediated cytolysis at modest levels using high effector:target ratios. The other CARs yielded lower and inconsistent levels of killing across multiple experiments.

CAR-Transduced Primary C8TLs Suppress CMV Replication

Figure 14:
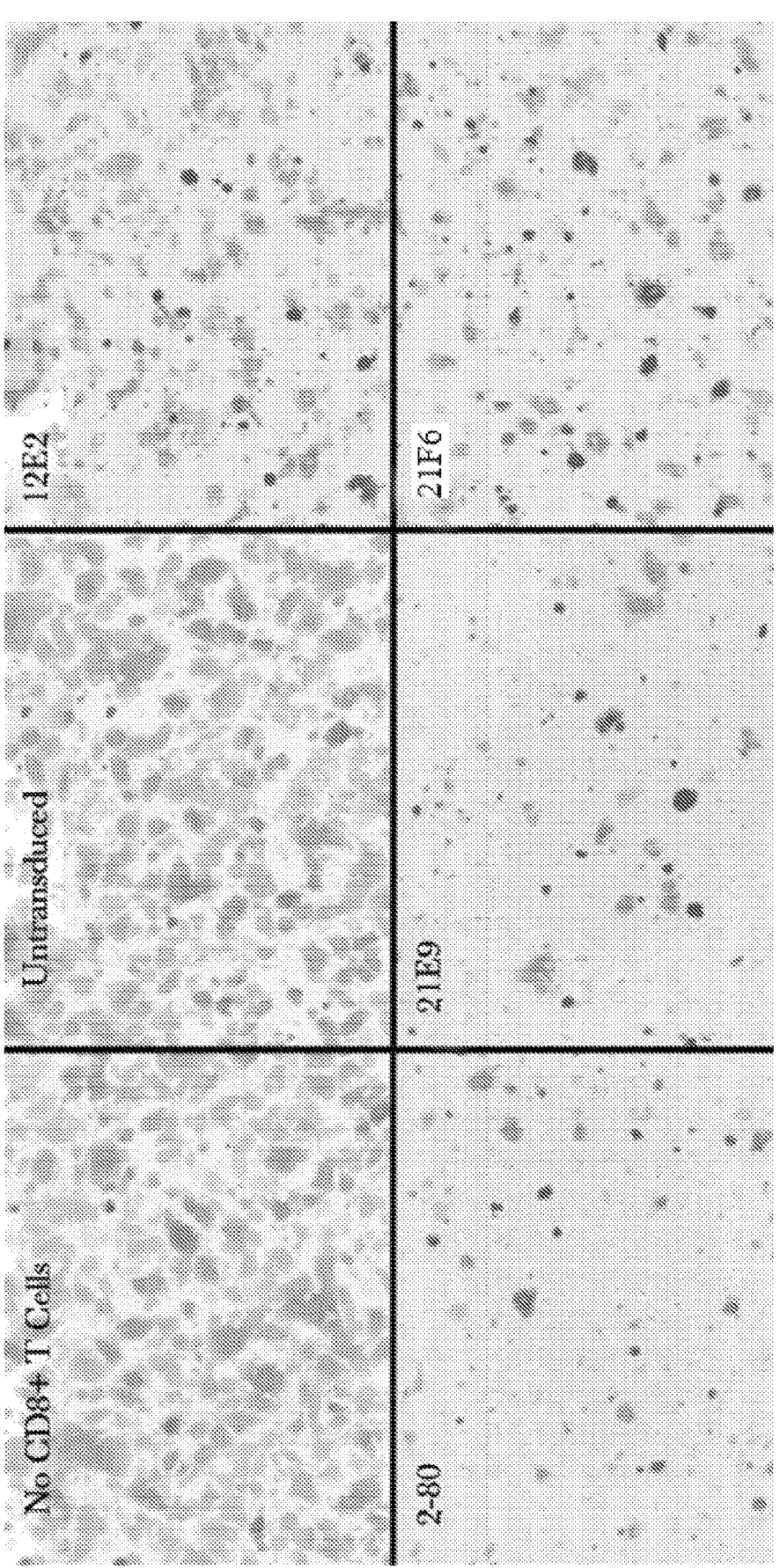
FIG. 14: Suppression of CMV replication in cell culture by CAR-transduced primary C8TLs. ARPE-19 cells were acutely infected with CMV TR (GFP-expressing) for four days, and then co-cultured with no cells, untransduced primary C8TLs, or CAR-transduced C8TLs (at a ratio of 10 C8TLs per target cell), followed by imaging eight hours later. Similar results were obtained with CMV strain TB40/E (not shown). These results are representative of three independent experiments with three different C8TL donors. For better reproducibility in black and white, the color of the original figure was inverted.

The antiviral activity of CAR-transduced C8TLs was evaluated by co-culture with acutely CMV-infected ARPE-19 cells using GFP-expressing CMV TR (FIG. 14). The four tested CARs all exhibited quantifiable antiviral activity with reduction of the concentration of fluorescent CMV-infected cells, even after a short incubation period of 8 hours. Across multiple experiments, CAR 21E9 mediated the most consistently potent antiviral activity. Similar results were seen with CMV TB40/E-infected ARPE-19 cells (not shown).

DISCUSSION

To date, only one CMV-specific CAR has been reported in detail. That CAR targets CMV glycoprotein B (gB), and C8TL transfected with CAR-encoding RNA were shown to be CMV-specific by responding to infected cells by releasing IFN-γ and TNF-α and modestly upregulating surface CD107a. Although cells transfected with the prior art CAR killed target cells expressing recombinant gB, it was subsequently shown that they do not kill CMV-infected cells, presumably due to viral escape mechanisms against cytolysis.

Here, eight candidate CMV-specific CARs targeting other viral proteins on infected cells were designed and screened. These antibodies were previously generated in mice using a Modified Vaccinia Ankara Virus (MVA) vector expressing PC-sequences derived from TB40/E and found to bind the PC with high affinity. All the exemplified CMV-specific CARs exhibited functional activity. However, at least one of the CMV-specific CARs (based on the gH-specific antibody 21E9) was consistently active by multiple functional tests against cells infected with both CMV TB40/E and TR strains, which belong to two different gH genotypes.

While all the CMV-specific CARs exhibited adequate levels of expression on transduced cells, they varied in function. The 21E9-based CAR exhibited consistently superior activity in all functional tests, while the 2-80-based CAR showed activity in most assays, although it seemed to confer nonspecific background activity. The other CMV-specific CARs targeting other PC subunits demonstrated minimal activity overall. Whether this indicates that gH is a superior target for CARs than other PC proteins is unclear. 21E9 and 2-80 antibodies have about 10-fold less binding affinity than the other antibodies, but because the other two gH-specific antibodies 62-11 and 18F10 with similar affinity yielded poorly active CARs, affinity itself is probably not the major determinant of CAR activity. Target protein expression could be a factor; gH appears to be more abundant on CMV-infected cells than UL128, UL130, and UL131A. Another potential element is that the gH-specific antibodies utilized here recognize gH in multiple contexts including monomeric gH, gH bound to gL, and gH associated with the PC, perhaps allowing a broader target for binding and recognition. Finally, it is notable that 21E9 and 2-80 target a site on gH that is distinct from other gH-specific antibodies, suggesting that this epitope region may be more accessible to antibody in the context of a CMV-specific CAR.

The data herein shows modest but reproducible CAR-mediated C8TL killing of CMV-infected cells at levels approaching those observed by Rauser et al, who demonstrated cytolysis of infected cells by endogenous CMV-specific C8TLs. Overall, the role of infected cell killing for in vivo efficacy of CMV-specific CARs may not be critical, since adoptive transfer of native CMV-specific C8TLs has clearly demonstrated their antiviral effects, suggesting that targeted non-cytolytic mechanisms may be sufficient.

Beyond direct utility for anti-CMV therapy, a CMV-specific CAR may have other applications by harnessing the pathogenesis of chronic CMV infection. In normal immunocompetent hosts, this virus establishes a chronic lifelong infection that is mostly latent, but with frequent low level subclinical reactivations that stimulate relatively high levels of persistently circulating functional anti-CMV T cells. In this regard, CMV serves analogously to an endogenous vaccine that boosts and maintains cellular immunity against itself. A strategy being considered for cancer immunotherapy has been to harness this process by transducing CMV-specific T cells isolated from peripheral blood with an anti-CD19 CAR, thereby coupling the anti-tumor response to the anti-CMV response by creating bi-specific T cells recognizing both CMV and CD19. A functional anti-CMV CAR could achieve the same goal without the need to isolate CMV-specific T cells, via co-expression of the anti-CMV CAR with a T cell receptor or CAR targeting another virus or tumor.

Overall, the data herein indicate that CMV-specific CARs as disclosed herein, particularly the 21E9 CAR, are strong candidates for testing as immunotherapeutic intervention or prophylaxis for disseminated CMV infection and/or combination with T cell receptor or CAR gene immunotherapy for other diseases, given that the CMV-specific CARs exhibit CMV-targeted function in terms of triggering to release cytokines, proliferation, infected cell killing, and suppression of viral replication.

REFERENCES

The following references are herein incorporated by reference in their entirety with the exception that, should the scope and meaning of a term conflict with a definition explicitly set forth herein, the definition explicitly set forth herein controls:

Staras S A, Dollard S C, Radford K W, Flanders W D, Pass R F, Cannon M J. Seroprevalence of cytomegalovirus infection in the United States, 1988-1994. Clin Infect Dis 2006; 43:1143-51.

Majeed A, Latif A, Kapoor V, et al. Resistant Cytomegalovirus Infection in Solid-organ Transplantation: Single-center Experience, Literature Review of Risk Factors, and Proposed Preventive Strategies. Transplantation proceedings 2018; 50:3756-62.

El Helou G, Razonable R R. Letermovir for the prevention of cytomegalovirus infection and disease in transplant recipients: an evidence-based review. Infection and drug resistance 2019; 12:1481-91.

Riddell S R, Walter B A, Gilbert M J, Greenberg P D. Selective reconstitution of CD8+ cytotoxic T lymphocyte responses in immunodeficient bone marrow transplant recipients by the adoptive transfer of T cell clones. Bone marrow transplantation 1994; 14 Suppl 4:S78-84.

Riddell S R, Watanabe K S, Goodrich J M, Li C R, Agha M E, Greenberg P D. Restoration of viral immunity in immunodeficient humans by the adoptive transfer of T cell clones. Science 1992; 257:238-41.

Walter E A, Greenberg P D, Gilbert M J, et al. Reconstitution of cellular immunity against cytomegalovirus in recipients of allogeneic bone marrow by transfer of T-cell clones from the donor. N Engl J Med 1995; 333: 1038-44.

Proff J, Walterskirchen C, Brey C, et al. Cytomegalovirus-Infected Cells Resist T Cell Mediated Killing in an HLA-Recognition Independent Manner. Frontiers in microbiology 2016; 7:844.

Full F, Lehner M, Thonn V, et al. T cells engineered with a cytomegalovirus-specific chimeric immunoreceptor. J Virol 2010; 84:4083-8.

Hahn G, Revello M G, Patrone M, et al. Human cytomegalovirus UL131-128 genes are indispensable for virus growth in endothelial cells and virus transfer to leukocytes. J Virol 2004; 78:10023-33.

Wang D, Shenk T. Human cytomegalovirus virion protein complex required for epithelial and endothelial cell tropism. Proc Natl Acad Sci USA 2005; 102:18153-8.

Chiuppesi F, Wussow F, Johnson E, et al. Vaccine-Derived Neutralizing Antibodies to the Human Cytomegalovirus gH/gL Pentamer Potently Block Primary Cytotrophoblast Infection. J Virol 2015; 89:11884-98.

Diamond D J, Chiuppesi F, Wussow F. MVA-gh/gL-PC vaccine derived antibodies neutralizing human cytomegalovirus infectivity and methods thereof. United States: City of Hope National Medical Center, 2018. U.S. Pat. No. 10,487,139.

Bennett M S, Joseph A, Ng H L, Goldstein H, Yang O O. Fine-tuning of T-cell receptor avidity to increase HIV epitope variant recognition by cytotoxic T lymphocytes. Aids 2010; 24:2619-28.

Ali A, Kitchen S G, Chen I S, Ng H L, Zack J A, Yang O O. HIV-1-Specific Chimeric Antigen Receptors Based on Broadly Neutralizing Antibodies. J Virol 2016; 90:6999-7006.

Logan A C, Nightingale S J, Haas D L, Cho G J, Pepper K A, Kohn D B. Factors influencing the titer and infectivity of lentiviral vectors. Hum Gene Ther 2004; 15:976-88.

Yang S, Cohen C J, Peng P D, et al. Development of optimal bicistronic lentiviral vectors facilitates high-level TCR gene expression and robust tumor cell recognition. Gene Ther 2008; 15:1411-23.

Ali A, Jamieson B D, Yang O O. Half-genome human immunodeficiency virus type 1 constructs for rapid production of reporter viruses. J Virol Methods 2003; 110:137-42.

Murphy E, Yu D, Grimwood J, et al. Coding potential of laboratory and clinical strains of human cytomegalovirus. Proc Natl Acad Sci USA 2003; 100:14976-81.

O'Connor C M, Murphy E A. A myeloid progenitor cell line capable of supporting human cytomegalovirus latency and reactivation, resulting in infectious progeny. J Virol 2012; 86:9854-65.

Britt W J. Human cytomegalovirus: propagation, quantification, and storage. Current protocols in microbiology 2010; Chapter 14:Unit 14E 3.

Wussow F, Chiuppesi F, Martinez J, et al. Human cytomegalovirus vaccine based on the envelope gH/gL pentamer complex. PLOS Pathog 2014; 10:e1004524.

Andreoni M, Faircloth M, Vugler L, Britt W J. A rapid microneutralization assay for the measurement of neutralizing antibody reactive with human cytomegalovirus. J Virol Methods 1989; 23:157-67.

Yang O O, Kalams S A, Rosenzweig M, et al. Efficient lysis of human immunodeficiency virus type 1-infected cells by cytotoxic T lymphocytes. J Virol 1996; 70:5799-806.

Bennett M S, Ng H L, Dagarag M, Ali A, Yang O O. Epitope-dependent avidity thresholds for cytotoxic T-lymphocyte clearance of virus-infected cells. J Virol 2007; 81:4973-80.

Stripecke R, Gerasch L, Theobald S, et al. CAR T Cells Targeted with a High Affinity Scfv Against the HCMV Glycoprotein Gb As Adoptive T Cell Therapy after Hematopoietic Stem Cell Transplantation. Blood 2016; 128:5721.

Shedlock D J, Talbott K T, Wu S J, et al. Vaccination with synthetic constructs expressing cytomegalovirus immunogens is highly T cell immunogenic in mice. Human vaccines & immunotherapeutics 2012; 8:1668-81.

Buscher N, Paulus C, Nevels M, Tenzer S, Plachter B. The proteome of human cytomegalovirus virions and dense bodies is conserved across different strains. Medical microbiology and immunology 2015; 204:285-93.

Barrios Y, Knor S, Lantto J, Mach M, Ohlin M. Clonal repertoire diversification of a neutralizing cytomegalovirus glycoprotein B-specific antibody results in variants with diverse anti-viral properties. Mol Immunol 2007; 44:680-90.

Lantto J, Fletcher J M, Ohlin M. Binding characteristics determine the neutralizing potential of antibody fragments specific for antigenic domain 2 on glycoprotein B of human cytomegalovirus. Virology 2003; 305:201-9.

Lantto J, Lindroth Y, Ohlin M. Non-germ-line encoded residues are critical for effective antibody recognition of a poorly immunogenic neutralization epitope on glycoprotein B of human cytomegalovirus. Eur J Immunol 2002; 32:1659-69.

Tempest P R, White P, Buttle M, Carr F J, Harris W J. Identification of framework residues required to restore antigen binding during reshaping of a monoclonal antibody against the glycoprotein gB of human cytomegalovirus. International journal of biological macromolecules 1995; 17:37-42.

Ohlin M, Owman H, Rioux J D, Newkirk M M, Borrebaeck C A. Restricted variable region gene usage and possible rheumatoid factor relationship among human monoclonal antibodies specific for the AD-1 epitope on cytomegalovirus glycoprotein B. Mol Immunol 1994; 31:983-91.

Newkirk M M, Gram H, Heinrich G F, Ostberg L, Capra J D, Wasserman R L. Complete protein sequences of the variable regions of the cloned heavy and light chains of a human anti-cytomegalovirus antibody reveal a striking similarity to human monoclonal rheumatoid factors of the Wa idiotypic family. J Clin Invest 1988; 81:1511-8.

Gilbert M J, Riddell S R, Plachter B, Greenberg P D. Cytomegalovirus selectively blocks antigen processing and presentation of its immediate-early gene product. Nature 1996; 383:720-2.

Rauser G, Einsele H, Sinzger C, et al. Rapid generation of combined CMV-specific CD4+ and CD8+ T-cell lines for adoptive transfer into recipients of allogeneic stem cell transplants. Blood 2004; 103:3565-72.

Sylwester A W, Mitchell B L, Edgar J B, et al. Broadly targeted human cytomegalovirus-specific CD4+ and CD8+ T cells dominate the memory compartments of exposed subjects. J Exp Med 2005; 202:673-85.

Wang X, Wong C W, Urak R, et al. CMVpp65 Vaccine Enhances the Antitumor Efficacy of Adoptively Transferred CD19-Redirected CMV-Specific T Cells. Clinical cancer research: an official journal of the American Association for Cancer Research 2015; 21:2993-3002.

All scientific and technical terms used in this application have meanings commonly used in the art unless otherwise specified.

Except when specifically indicated, peptides are indicated with the N-terminus on the left and the sequences are written from the N-terminus to the C-terminus. Similarly, except when specifically indicated, nucleic acid sequences are indicated with the 5' end on the left and the sequences are written from 5' to 3'.

As used herein, the terms "subject", "patient", and "individual" are used interchangeably to refer to humans and non-human animals. The terms "non-human animal" and "animal" refer to all non-human vertebrates, e.g., non-human mammals and non-mammals, such as non-human primates, horses, sheep, dogs, cows, pigs, chickens, and other veterinary subjects and test animals. In some embodiments, the subject is a mammal. In some embodiments, the subject is a human.

As used herein, the term "diagnosing" refers to the physical and active step of informing, i.e., communicating verbally or by writing (on, e.g., paper or electronic media), another party, e.g., a patient, of the diagnosis. Similarly, "providing a prognosis" refers to the physical and active step of informing, i.e., communicating verbally or by writing (on, e.g., paper or electronic media), another party, e.g., a patient, of the prognosis.

The use of the singular can include the plural unless specifically stated otherwise. As used in the specification and the appended claims, the singular forms "a", "an", and "the" can include plural referents unless the context clearly dictates otherwise.

As used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

As used herein, the phrase "one or more of", e.g., "one or more of A, B, and/or C" means "one or more of A", "one or more of B", "one or more of C", "one or more of A and one or more of B", "one or more of B and one or more of C", "one or more of A and one or more of C" and "one or more of A, one or more of B, and one or more of C".

The phrase "comprises or consists of A" is used as a tool to avoid excess page and translation fees and means that in some embodiments the given thing at issue: comprises A or consists of A. For example, the sentence "In some embodiments, the composition comprises or consists of A" is to be interpreted as if written as the following two separate sentences: "In some embodiments, the composition comprises A. In some embodiments, the composition consists of A."

Similarly, a sentence reciting a string of alternates is to be interpreted as if a string of sentences were provided such that each given alternate was provided in a sentence by itself. For example, the sentence "In some embodiments, the composition comprises A, B, or C" is to be interpreted as if written as the following three separate sentences: "In some embodiments, the composition comprises A. In some embodiments, the composition comprises B. In some embodiments, the composition comprises C." As another example, the sentence "In some embodiments, the composition comprises at least A, B, or C" is to be interpreted as if written as the following three separate sentences: "In some embodiments, the composition comprises at least A. In some embodiments, the composition comprises at least B. In some embodiments, the composition comprises at least C."

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A cytomegalovirus specific chimeric antigen receptor (CMV-specific CAR), which comprises a single chain antibody (scFv) sequence having the following CDR sequences:

VH CDR1-SEQ ID NO: 30,
VH CDR2-SEQ ID NO: 39,
VH CDR3-SEQ ID NO: 46,
VL CDR1-SEQ ID NO: 59,
VL CDR2-SEQ ID NO: 66, and
VL CDR3-SEQ ID NO: 71.

2. The CMV-specific CAR according to claim 1, wherein the single chain antibody comprises SEQ ID NO: 11 and SEQ ID NO: 12.

3. An expression vector comprising a nucleic acid sequence encoding a CMV-specific CAR according to claim 1.

4. A host cell comprising one or more expression vectors according to claim 3.

5. The host cell according to claim 4, wherein the host cell is a CD8+ T lymphocyte, hematopoietic stem cell, or a hematopoietic progenitor cell.

6. A cell that is the progeny of the host cell of claim 4.

7. The cell according to claim 4, wherein the cell expresses one or more chimeric antigen receptors encoded by the one or more expression vectors.

8. A method of treating, reducing, or inhibiting an infection by a cytomegalovirus in a subject, which comprises transplanting one or more cells according to claim 4, in the subject.

9. The method according to claim 8, wherein the subject is human and/or the cytomegalovirus is a human cytomegalovirus.

10. The method according to claim 8, wherein the subject has an immunodeficiency.

11. A method of killing cells infected with a cytomegalovirus, which comprises contacting the infected cells with one or more cells (a) that express one or more CMV-specific CARs according to claim 1, or (b) comprise an expression vector that encodes the one or more CMV-specific CARs.

12. A method of reducing replication of a cytomegalovirus in a cell or a subject, which comprises contacting the cell with or administering to the subject one or more cells (a) that express one or more CMV-specific CARs according to claim 1, or (b) comprise an expression vector that encodes the one or more CMV-specific CARs.

13. A method of treating, reducing, or inhibiting an infection by a cytomegalovirus in a subject, which comprises administering to the subject (a) an expression vector that encodes the CMV-specific CAR according to claim 1, or (b) one or more cells that are transduced with the expression vector.

14. A method of treating, reducing, or inhibiting an infection by a cytomegalovirus in a subject, which comprises transplanting one or more cells that express one or more CMV-specific CARs according to claim 1 to the subject.

15. A cytomegalovirus specific chimeric antigen receptor (CMV-specific CAR), which comprises or consists of SEQ ID NO: 89.

16. A method of treating, reducing, or inhibiting an infection by a cytomegalovirus in a subject, which comprises administering to the subject (a) an expression vector that encodes the CMV-specific CAR according to claim 15, or (b) one or more cells that are transduced with the expression vector.

17. The method according to claim 16, wherein the subject is human and/or the cytomegalovirus is a human cytomegalovirus.

* * * * *